United States Patent
Mun et al.

(10) Patent No.: US 10,840,457 B2
(45) Date of Patent: Nov. 17, 2020

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Soung Yun Mun, Cheonan-si (KR); Yeon Hee Choi, Cheonan-si (KR); Sun-Hee Lee, Hwaseong-si (KR); Seul-gi Kim, Daejeon (KR); Seungwon Yeo, Daejeon (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 289 days.

(21) Appl. No.: 15/762,164

(22) PCT Filed: Sep. 2, 2016

(86) PCT No.: PCT/KR2016/009822
§ 371 (c)(1),
(2) Date: Mar. 22, 2018

(87) PCT Pub. No.: WO2017/052099
PCT Pub. Date: Mar. 30, 2017

(65) Prior Publication Data
US 2018/0269405 A1 Sep. 20, 2018

(30) Foreign Application Priority Data
Sep. 22, 2015 (KR) .................. 10-2015-0134077

(51) Int. Cl.
*H01L 51/00* (2006.01)
*C07D 491/048* (2006.01)
(Continued)

(52) U.S. Cl.
CPC ........ *H01L 51/0071* (2013.01); *C07D 209/56* (2013.01); *C07D 209/82* (2013.01);
(Continued)

(58) Field of Classification Search
None
See application file for complete search history.

(56) References Cited

U.S. PATENT DOCUMENTS

2014/0034915 A1* 2/2014 Lee .................. H01L 51/0074
257/40
2014/0117331 A1 5/2014 Kim et al.
(Continued)

FOREIGN PATENT DOCUMENTS

CN 103804333 A 5/2014
CN 104513246 A 4/2015
(Continued)

OTHER PUBLICATIONS

Machine translation of KR-20140120090, translation generated Mar. 2020, 60 pages (Year: 2020).*
(Continued)

*Primary Examiner* — Robert S Loewe
(74) *Attorney, Agent, or Firm* — Vorys, Sater, Seymour & Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and an electronic device comprising the same. The driving voltage of an organic electronic device can be lowered, and the luminous efficiency and life time of an organic electronic device can be improved by comprising the compound represented by the Formula 1 in the organic material layer.

13 Claims, 1 Drawing Sheet

(51) Int. Cl.

| | | |
|---|---|---|
| *C07D 495/04* | (2006.01) | |
| *C09K 11/06* | (2006.01) | |
| *C07D 209/82* | (2006.01) | |
| *C07D 403/04* | (2006.01) | |
| *C07D 519/00* | (2006.01) | |
| *C07D 209/56* | (2006.01) | |
| *H01L 51/50* | (2006.01) | |
| *H01L 51/56* | (2006.01) | |

(52) U.S. Cl.
CPC ....... *C07D 403/04* (2013.01); *C07D 491/048* (2013.01); *C07D 495/04* (2013.01); *C07D 519/00* (2013.01); *C09K 11/06* (2013.01); *H01L 51/0052* (2013.01); *H01L 51/0054* (2013.01); *H01L 51/0061* (2013.01); *H01L 51/0067* (2013.01); *H01L 51/0072* (2013.01); *H01L 51/0074* (2013.01); *C09K 2211/1007* (2013.01); *C09K 2211/1011* (2013.01); *C09K 2211/1018* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/1088* (2013.01); *H01L 51/001* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/56* (2013.01); *H01L 2251/558* (2013.01)

(56) References Cited

U.S. PATENT DOCUMENTS

2016/0225992 A1* 8/2016 Ito .................. C09B 23/148
2017/0162797 A1* 6/2017 Lee .................. C07D 403/04

FOREIGN PATENT DOCUMENTS

| | | | | |
|---|---|---|---|---|
| CN | 104513247 A | | 4/2015 | |
| KR | 10-2014-0120090 A | | 10/2014 | |
| KR | 20140120090 A | * | 10/2014 | ............. C09K 11/06 |
| KR | 10-2015-0106043 A | | 9/2015 | |
| WO | WO-2016006959 A1 | * | 1/2016 | ........... C07D 405/04 |

OTHER PUBLICATIONS

Chinese Office Action dated Mar. 24, 2020 for corresponding Chinese Patent Application No. 201680055160.3, six pages.

* cited by examiner

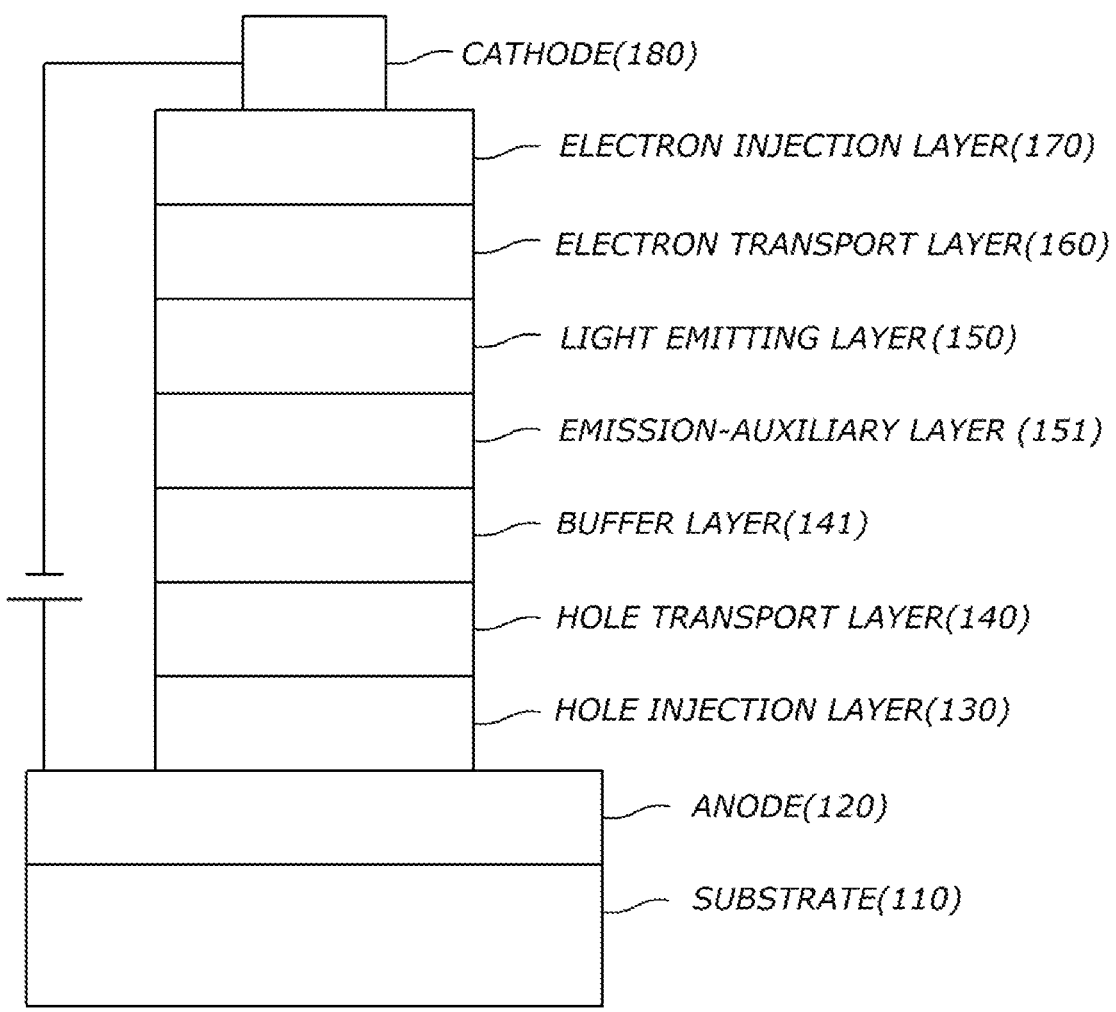

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0134077, filed on Sep. 22, 2015, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compound for organic electric element, organic electric element comprising the same, and an electronic device thereof.

Background Art

Polycyclic compounds containing heteroatoms differ largely in their properties depending on the structure of each compound. Therefore, they have been applied to various layers of OLEDs as a material of organic light emitting diodes (OLEDs). In particular, band gap (HOMO, LUMO), electrical properties, chemical properties, physical properties and the like are different depending on the number and the fused position of ring, and the types and the arrangement of heteroatoms, and thus polycyclic compounds have been developed to be applied to the various layers of OLED. For example, U.S. Patent Application Publication No. 2008/0145708 A1 (published on Jun. 19, 2008) discloses the embodiment in which polycyclic compound is applied to a hole transport layer or a phosphorescent host of OLED, and Korean Patent Publication No. 10-2007-0012218 (published on Jan. 25, 2007) discloses the embodiment in which polycyclic compound is applied to an electric transport layer of OLED.

On the other hand, in recent years, development of OLED materials has been actively carried out in relation to the types, the number and the position of heteroatoms of a five-ring membered compound, as disclosed in Korean Patent Publication No. 10-2013-0103180 (published on Sep. 23, 2013).

OBJECT, TECHNICAL SOLUTION AND EFFECTS OF THE INVENTION

The objection of the present invention is to provide a compound lowering driving voltage and improving luminous efficiency and lifetime of the element, an organic electric element comprising the same, and an electric device thereof by using the properties of a polycyclic compound.

In an aspect of the present invention, the present invention provides the compound represented by the following formula.

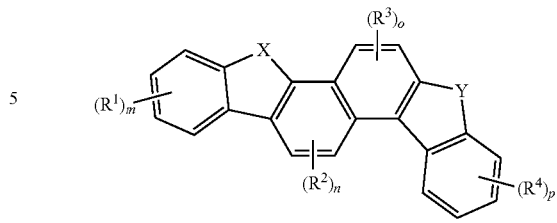

In another aspect of the present invention, the present invention provides an organic electric element using the compound represented by the formula above, and an electronic device thereof.

By using the compound according to embodiments of the present invention, the driving voltage of element can be lowered, and the luminous efficiency and lifetime of the element can be significantly improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

The FIGURE illustrates an example of an organic electric element according to an embodiment of the present invention.

Hereinafter, some embodiments of the present invention will be described in detail with reference to the accompanying illustrative drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic) and an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

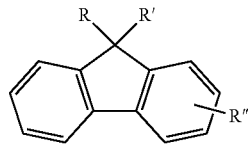

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

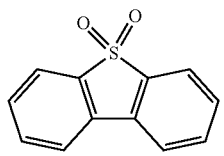 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted" in the expression "substituted or unsubstituted" means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

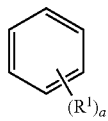

Wherein, when a is an integer of zero, the substituent $R^1$ is absent, that is, hydrogen atoms are bonded to all the carbon constituting the benzene ring, and chemical formulas or compounds may be written without explicitly describing the hydrogen. In addition, one substituent $R^1$ is bonded to any carbon of the carbons forming the benzene ring when "a" is an integer of 1, substituent $R^1$s are bonded, for example, as followings when "a" is an integer of 2 or 3, substituent $R^1$s are bonded to the carbon of the benzene ring in a similar manner when "a" is an integer of 4 to 6, and $R^1$s may be the same or different from each other when "a" is an integer of 2 or more.

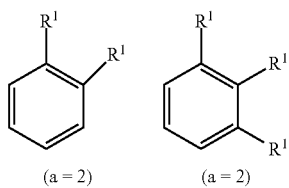

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 110 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may comprise a hole injection layer 130, a hole transport layer 140, a light emitting layer 150, an electron transport layer 160, and an electron injection layer 170 formed in sequence on the first electrode 120. Here, at least one layer of the organic material layer may be omitted, the organic material layer may further include a hole blocking layer, an electron blocking layer, an emission-auxiliary layer 151, an electron transport auxiliary layer, a buffer layer 141, etc., the electron transport layer 160 or the like may serve as the hole blocking layer.

Although not shown, the organic electric element according to an embodiment of the present invention may further include at least a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, and the like, as a host or a dopant material of a light emitting layer 150, or as a material of a layer for improving luminous efficiency. For example, the inventive compound may be used as material of the light emitting layer 150, the hole transport layer 140, and/or the emission-auxiliary layer 151, preferably, as material of the light emitting layer 150.

On the other hand, even if the core is the same core, the band gap, the electrical characteristics, the interface characteristics, and the like may be different depending on which substituent is bonded at which position. Therefore, it is necessary to study the selection of the core and the combination of the core and the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by forming a light emitting layer 150 which comprises the compound represented by the formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by the following formula 1.

[Formula 1]

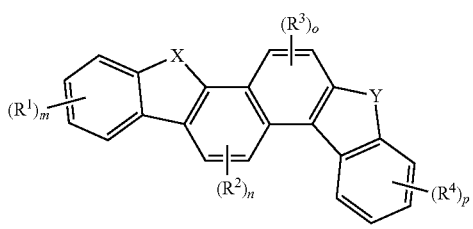

In the formula 1, each of symbols may be defined as follows.

$R^1$ to $R^4$ are each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group and a $C_6$-$C_{30}$ aryloxy group, with the proviso that neighboring $R^2$s and/or neighboring $R^3$s are bonded to each other to form a ring, and neighboring $R^1$s and/or neighboring $R^4$s are optionally bonded to each other to form a ring.

m and p are each an integer of 0 to 4, n and o are each an integer of 0 to 2, and a plurality of $R^1$s to a plurality of $R^4$s are the same or different from each other when m, p, n and o are each an integer of 2 or more.

In $R^1$ to $R^4$, a ring formed by adjacent $R^1$s to adjacent $R^4$s bonding to each other may be a $C_6$-$C_{60}$ aromatic ring, a fluorene, a $C_2$-$C_{60}$ heterocyclic group containing at least one heteroatom selected from the group consisting of O, N, S, Si, and P, or a fused ring group of a $C_3$-$C_{60}$ aliphatic ring and a $C_6$-$C_{60}$ aromatic ring.

When $R^1$ to $R^4$ are an aryl group, $R^1$ to $R^4$ may be preferably a $C_6$-$C_{30}$ aryl group, more preferably a $C_6$-$C_{18}$ aryl group, for example, phenyl, benzophenanthrene and the like. When $R^1$ to $R^4$ are heterocyclic group, $R^1$ to $R^4$ may be preferably a $C_2$-$C_{30}$ heterocyclic group, more preferably a $C_2$-$C_{25}$ heterocyclic group, for example, pyrimidine, carbazole, dihydrodiphenyl acridine and the like. A ring formed by adjacent $R^2$s and/or adjacent $R^3$s bonding to each other may be, for example, benzene ring.

X and Y are each independently N(-$L^1$-$Ar^1$), S, O or C($Ar^2$)($Ar^3$). Here, one of X and Y is N(-$L^1$-$Ar^1$), and the other is S, O or C($Ar^2$)($Ar^3$). That is, the case where both of X and Y are N(-$L^1$-$Ar^1$) is excluded.

In N(-$L^1$-$Ar^1$), $L^1$ may be each independently selected from the group consisting of a single bond, a $C_6$-$C_{60}$ arylene group, a fluorenylene group; a $C_2$-$C_{60}$ heterocyclic group containing at least one heteroatom selected from the group consisting of O, N, S, Si, and P, and a fused ring formed by a $C_3$-$C_{60}$ aliphatic ring and a $C_6$-$C_{60}$ aromatic ring.

When $L^1$ is an arylene group, $L^1$ may be preferably a $C_6$-$C_{30}$ arylene group, more preferably $C_6$-$C_{12}$ arylene group, for example, phenyl, naphthyl, biphenyl and the like. When $L^1$ is a heterocyclic group, $L^1$ may be preferably $C_2$-$C_{30}$ heterocyclic group, more preferably $C_2$-$C_{18}$ heterocyclic group, for example, imidazole, pyrimidine, triazine, quinazoline, quinoxaline, pyridopyrimidine, pyridoindole, pyrimidoindole, pyridopyridine, benzoquinazoline, benzothienopyrimidine benzofuropyrimidine, dibenzoquinazoline, dibenzofuran, dimethylbenzoindenopyrimidine, naphthothienopyrimidine, naphthofuropyrimidine, phenanthrofuropyrimidine and the like.

In N(-$L^1$-$Ar^1$), $Ar^1$ may be selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, -$L^a$-N($R^a$)($R^b$), a $C_1$-$C_{30}$ alkoxyl group, and a $C_6$-$C_{30}$ aryloxy group.

When $Ar^1$ is an aryl group, $Ar^1$ may be preferably $C_6$-$C_{30}$ aryl group, more preferably $C_6$-$C_{18}$ aryl group, for example, phenyl, biphenyl, terphenyl, naphthyl, phenanthrene, fluoranthene, pyrene, triphenylene and the like. When $Ar^1$ is a heterocyclic group, $Ar^1$ may be preferably $C_2$-$C_{30}$ heterocyclic group, more preferably $C_2$-$C_{18}$ heterocyclic group, for example, imidazole, pyridine, pyrimidine, triazine, quinazoline, quinoxaline, benzoquinazoline, carbazole, cyanthrene, pyridopyrimidine, pyridoindole, benzothienopyrimidine, benzofuropyrimidine, benzothienopyridine, dibenzofuran, dibenzothiophene, dibenzoquinazoline, dimethylbenzoindenopyrimidine, naphthofuropyrimidine, phenanthrofuropyrimidine, indolocarbazole, pyrimidoindole, naphthothienopyrimidine, benzonaphthothiophene and the like. When $Ar^1$ is a fluorenyl group, $Ar^1$ may be 9,9-dimethyl-9H-fluorene, 9,9'-spirobifluorene and the like, and when $Ar^1$ is an alkyl group, $Ar^1$ may be a methyl group, and when $Ar^1$ is an alkenyl group, $Ar^1$ may be an ethenyl group $L^a$ may be each independently selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group of a $C_3$-$C_{60}$ aliphatic ring and a $C_6$-$C_{60}$ aromatic ring, and $R^a$ and $R^b$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a $C_1$-$C_{50}$ alkyl group, a fused ring group of a $C_6$-$C_{60}$ aromatic ring and a $C_3$-$C_{60}$ aliphatic ring, and a $C_2$-$C_{20}$ alkenyl group.

$Ar^2$ and $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_2$-$C_{30}$ alkoxyl group, and a $C_6$-$C_{30}$ aryloxy group. $Ar^2$ and $Ar^3$ may be bonded to each other to form a spiro compound together with C they are bonded to. For example, $Ar^2$ and $Ar^3$ may be each independently phenyl, methyl and the like.

$R^1$ to $R^4$, $R^a$, $R^b$, $L^1$, $L^a$, $Ar^1$ to $Ar^3$ and a ring formed by adjacent $R^1$s to adjacent $R^4$s may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, —N($R^c$)($R^d$), a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

$R^c$ and $R^d$ may be each independently selected from the group consisting of a $C_6$-$C_{60}$ aryl group, a fluorenyl group and a $C_2$-$C_{60}$ heterocyclic group containing at least one heteroatom selected from the group consisting of O, N, S, Si and P.

The formula 1 may be represented by formula 1-1 or the following formula 1-2. In the formula 1, the formula 1 may be represented by the following formula 1-1 when X is N(-$L^1$-$Ar^1$) and Y is S, O or C($Ar^2$)($Ar^3$), and the formula 1 may be represented by the following formula 1-2, when X is S, O or C($Ar^2$)($Ar^3$) and Y is N-$L^1$-$Ar^1$.

<Formula 1-1>

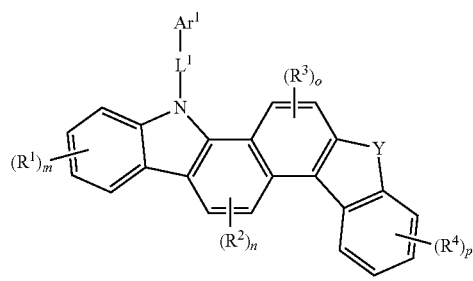

<Formula 1-2>

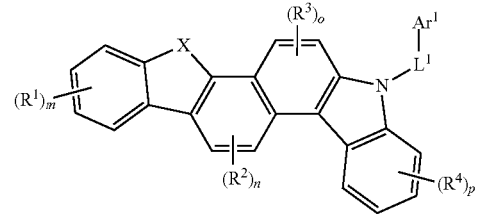

In the formulas 1-1 and 1-2, X, Y, $R^1$ to $R^4$, $Ar^1$, $L^1$, m, n, o and p are the same as defined in the formula 1.

The formula 1 may be represented by the following formula 2 when benzene ring is formed by adjacent $R^2$s bonding to each other, the formula 1 may be represented by the following formula 3 when benzene ring is formed by adjacent $R^3$s bonding to each other, and the formula 1 may be represented by the following formula 4 when benzene ring is formed by adjacent $R^2$s bonding to each other and adjacent $R^3$s bonding to each other.

<Formula 2>

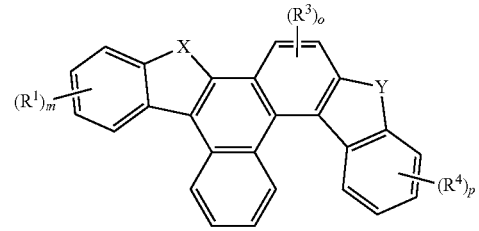

<Formula 3>

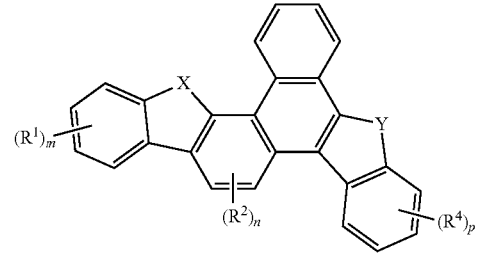

<Formula 4>

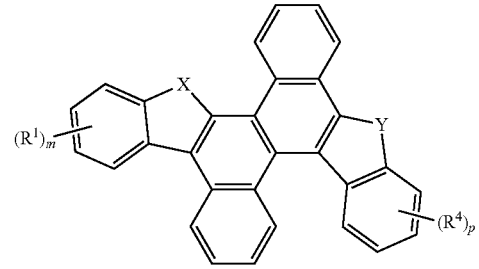

In the formulas 2 to 4, symbols such as X, Y, $R^1$ to $R^4$, m, n, o and p and the like are the same as defined in the formula 1.

Preferably, $Ar^1$ may be represented by one of the following formulas A-1 to A-3 when X or Y is $N(-L^1-Ar^1)$ in the formula 1.

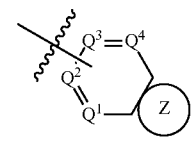
<A-1>

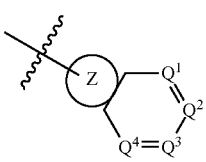
<A-2>

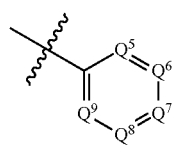
<A-3>

In the formulas A-1 and A-2, Z ring is a $C_6-C_{60}$ aromatic ring or a $C_2-C_{60}$ heterocyclic group containing at least one heteroatom selected from the group consisting of O, N, S, Si, and P.

In the formula A-1, one of $Q^1$ to $Q^4$ is carbon (C) boned to $L^1$, and the others are each independently N or $C(R^e)$. Preferably, one of $Q^1$ to $Q^4$ is C, and at least one of the others is N.

In the formula A-2, $Q^1$ to $Q^4$ are each independently N or $C(R^e)$, preferably, at least one of $Q^1$ to $Q^4$ is N.

In the formula A-3, $Q^5$ to $Q^9$ are each independently N or $C(R^e)$, preferably, at least one of $Q^5$ to $Q^9$ is N.

In the formulas A-1 to A-3, $R^e$ is selected from the group consisting of hydrogen, deuterium, halogen, a silane group substituted or unsubstituted with a $C_1-C_{20}$ alkyl group or a $C_6-C_{20}$ aryl group, a siloxane group, a boron group, a germanium group, a cyano group, a nitro group, a $C_1-C_{20}$ alkylthio group, a $C_1-C_{20}$ alkoxyl group, a $C_1-C_{20}$ alkyl group, a $C_2-C_{20}$ alkenyl group, a $C_2-C_{20}$ alkynyl group, a $C_6-C_{20}$ aryl group, a $C_6-C_{20}$ aryl group substituted with deuterium, a fluorenyl group, a $C_2-C_{20}$ heterocyclic group containing at least one heteroatom selected from the group consisting of O, N, S, Si, and P, a $C_3-C_{20}$ cycloalkyl group, a $C_7-C_{20}$ arylalkyl group, and a $C_8-C_{20}$ arylalkenyl group.

Preferably, the formula 1 may be represented by one of the following formulas 5 to 10.

When benzene ring is formed by adjacent $R^2$s and/or adjacent $R^3$s bonding to each other and X is $N(-L^1-Ar^1)$, wherein $Ar^1$ is represented by the formula A-1, the formula 1 may be represented by any of the following formulas 5 to 7. When benzene ring is formed by adjacent $R^2$s and/or adjacent $R^3$s bonding to each other and Y is $N(-L^1-Ar^1)$, wherein $Ar^1$ is represented by the formula A-1, the formula 1 may be represented by any of the following formulas 8 to 10.

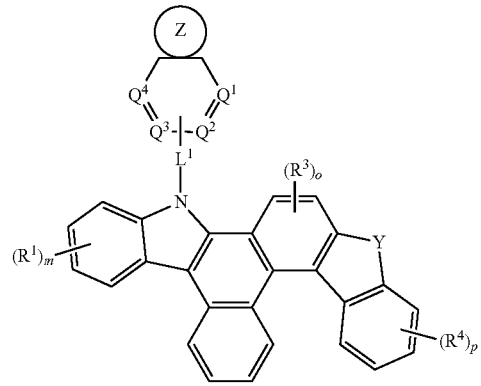
<Formula 5>

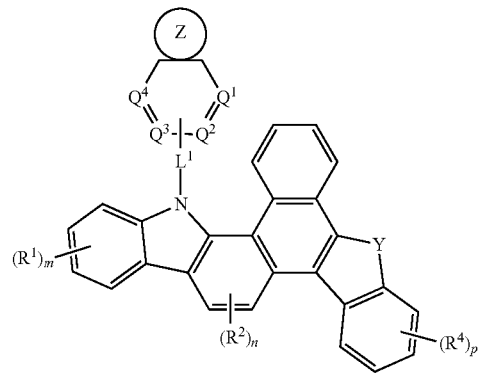
<Formula 6>

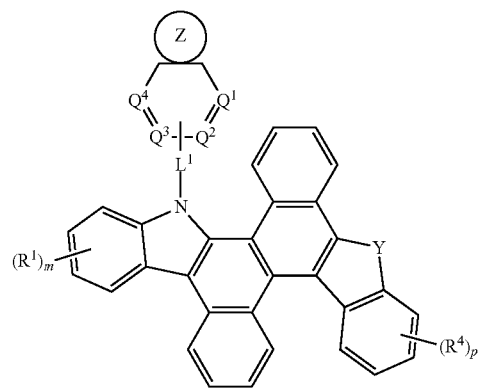
<Formula 7>

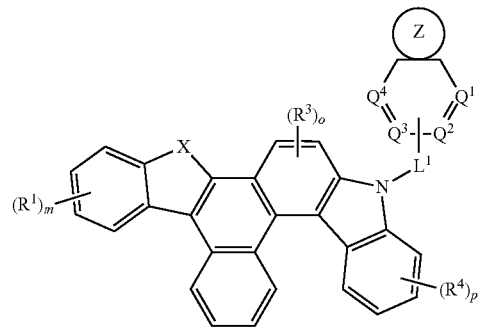
<Formula 8>

<Formula 9>

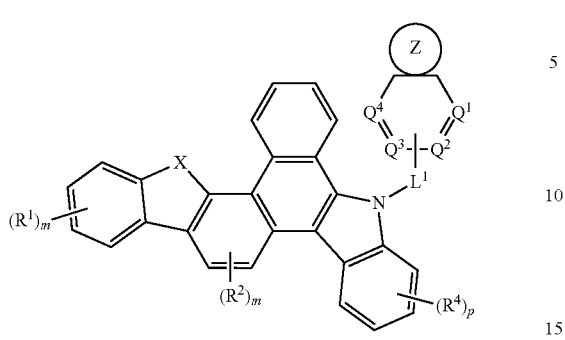

<Formula 10>

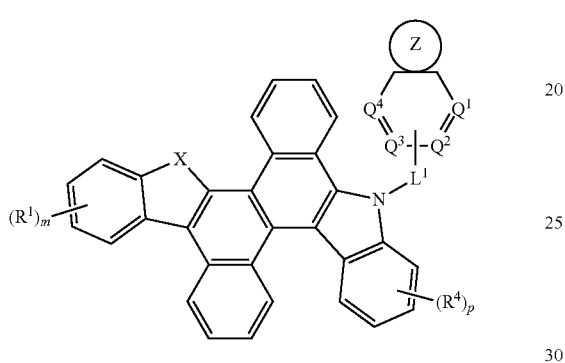

In the formulas 5 to 10, symbols such as X, Y, $R^1$ to $R^4$, m, n, o and p and the like are the same as defined in the formula 1, and Z ring, and $Q^1$ to $Q^4$ are the same as defined in the formula A-1.

Specifically, Z ring may be one of the following groups.

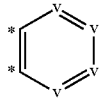 <Z-1>

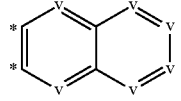 <Z-2>

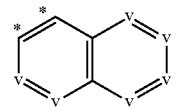 <Z-3>

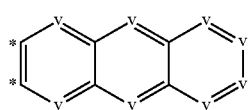 <Z-4>

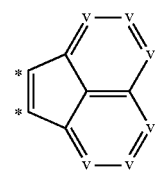 <Z-5>

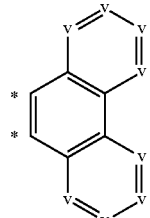 <Z-6>

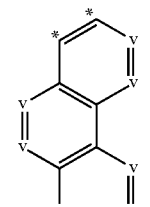 <Z-7>

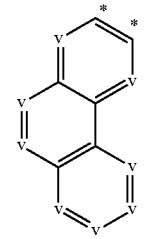 <Z-8>

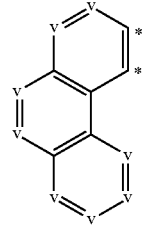 <Z-9>

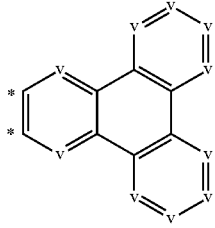 <Z-10>

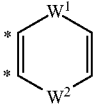 <Z-11>

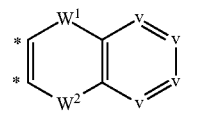 <Z-12>

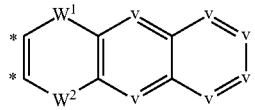 <Z-13>

-continued

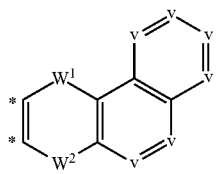
<Z-14>

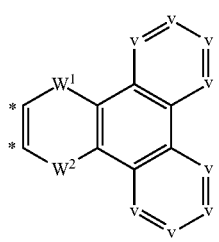
<Z-15>

In the Z ring group (Z-1 to Z-15), V is each independently N, C or C(R$^e$). With the proviso that V is N or C(R$^e$) when the above group is Z ring of formula A-1, one of Vs is carbon (C) boned to L$^1$, the others are each independently N or C(R$^e$) when the above group is Z ring of A-2.

In the Z ring group, W$^1$ and W$^2$ are each independently a single bond, N(-L$^1$-Ar$^1$), S, O or C(Ar$^2$)(Ar$^3$), L$^1$, Ar$^1$ to Ar$^3$ and the like are the same as defined in the formula 1, R$^e$ is the same as defined in the formulas A-1 to A-3, and "*" indicates the position where a ring comprising Q$^1$ to Q$^4$ in the formulas A-1 and A-2 is bonded.

Preferably, in the formulas A-1 and A-2, when at least one of Q$^1$ to Q$^4$ is N, Z ring may be represented by one of the following formulas Z-16 to Z-50.

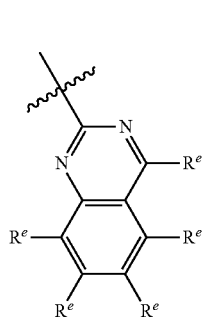
<Z-16>

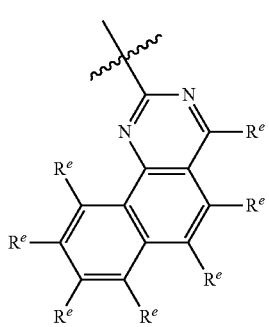
<Z-17>

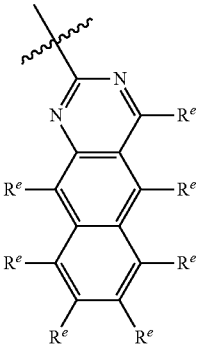
<Z-18>

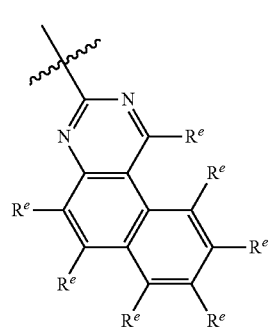
<Z-19>

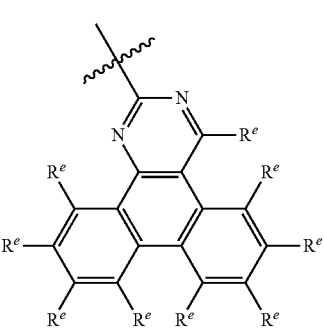
<Z-20>

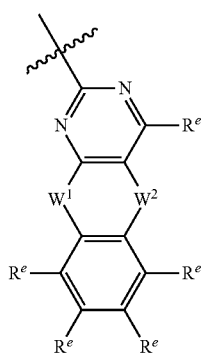
<Z-21>

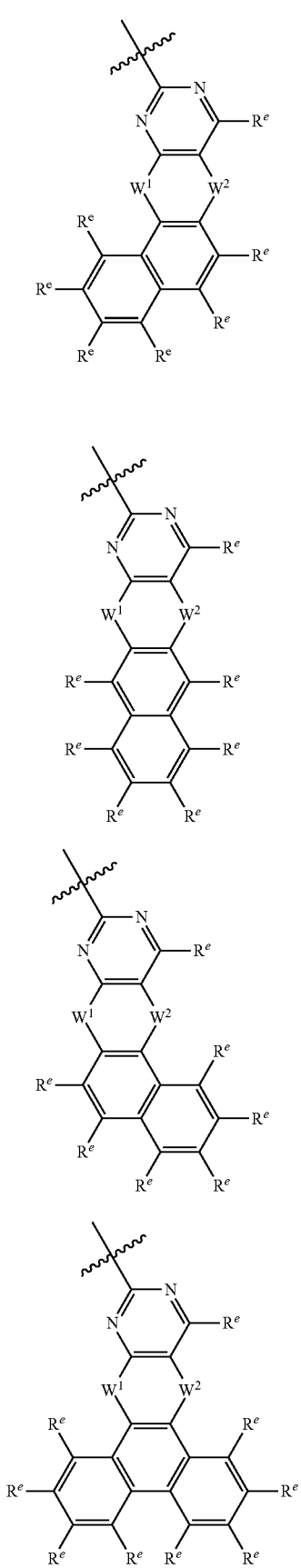
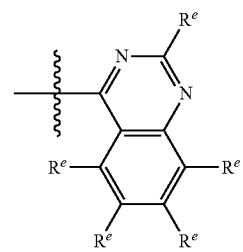
<Z-26>
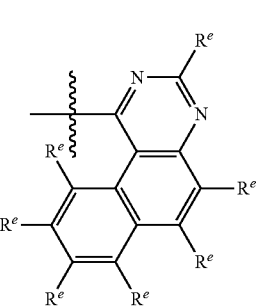
<Z-27>
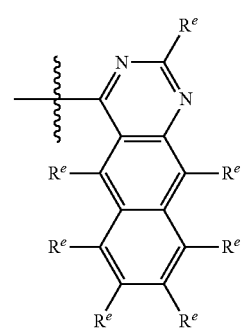
<Z-28>
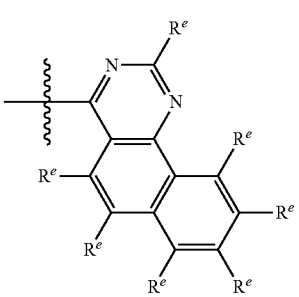
<Z-29>
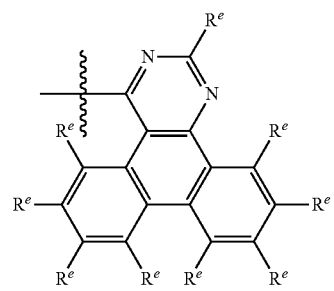
<Z-30>

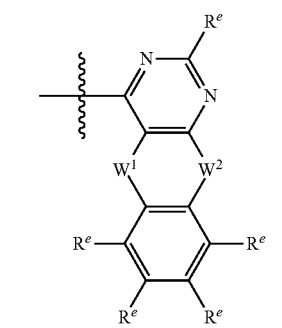
<Z-31>
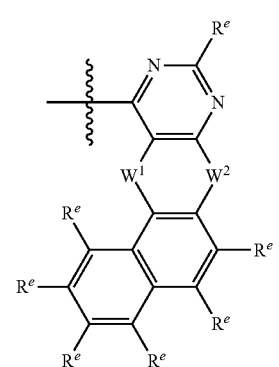
<Z-32>
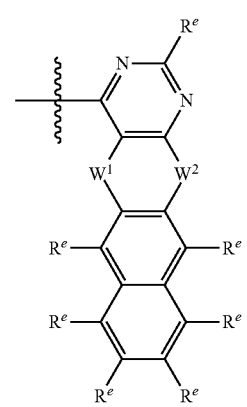
<Z-33>
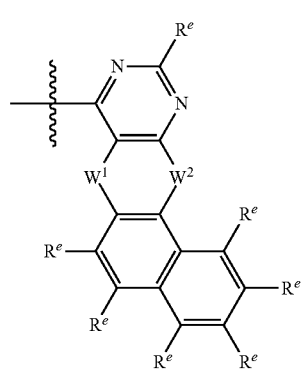
<Z-34>
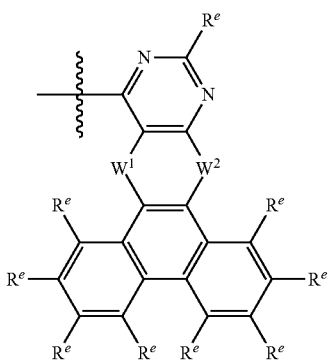
<Z-35>
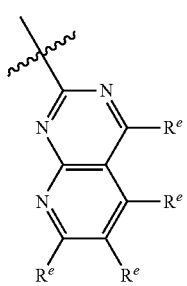
<Z-36>
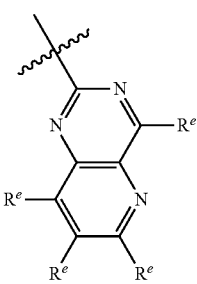
<Z-37>
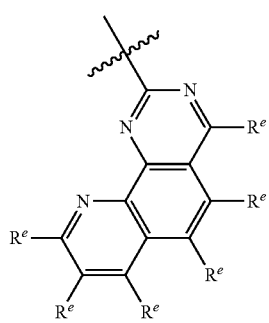
<Z-38>
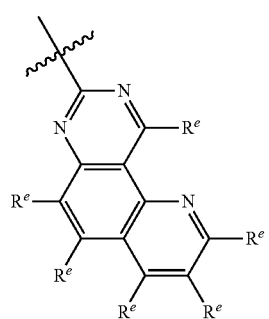
<Z-39>

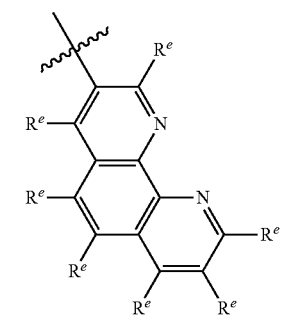 <Z-40>
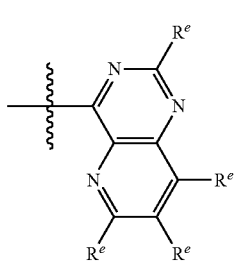 <Z-41>
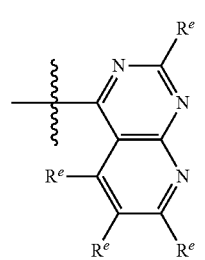 <Z-42>
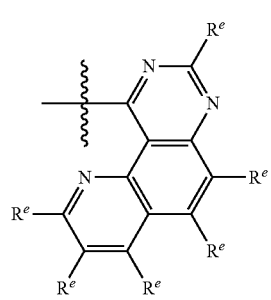 <Z-43>
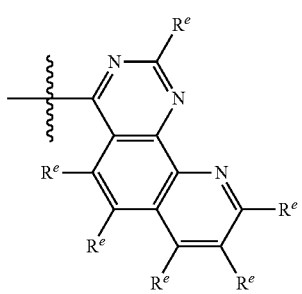 <Z-44>
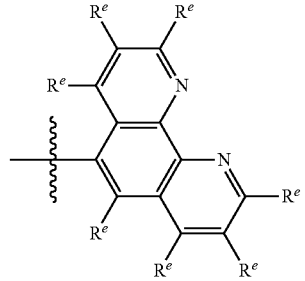 <Z-45>
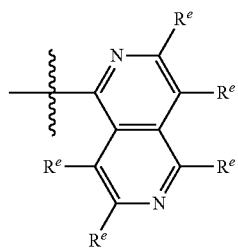 <Z-46>
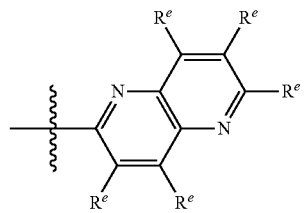 <Z-47>
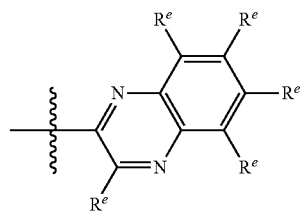 <Z-48>
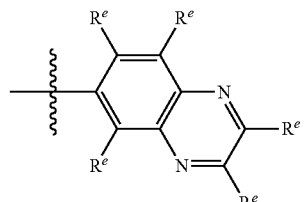 <Z-49>
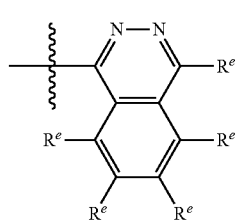 <Z-50>
In the above group (Z-16 to Z-50, $R^e$, $W^1$ and $W^2$ are the same as defined in the formulas A-1 and A-2.
Specifically, the compound represented by the formula 1 may be one of the following compounds.

P 1-1
P 1-2
P 1-3
P 1-4
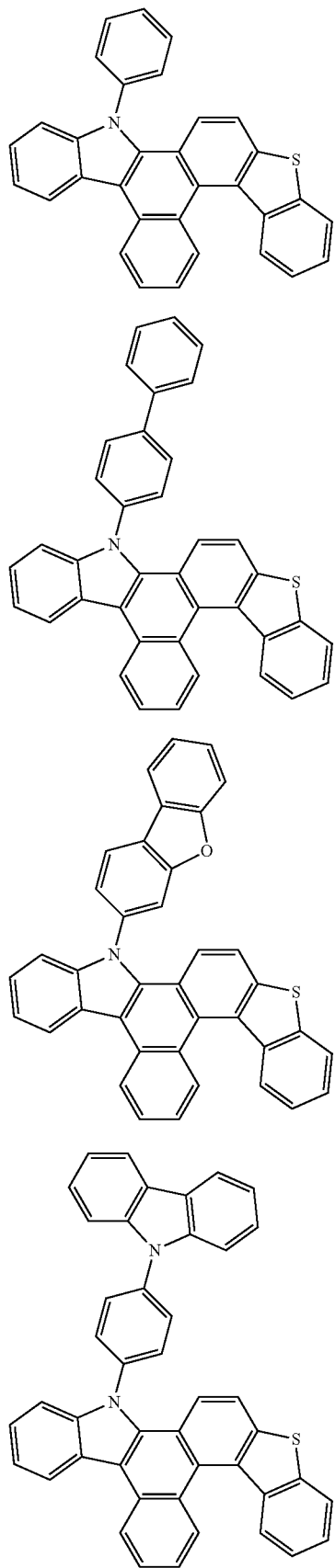
P 1-5
P 1-6
P 1-7
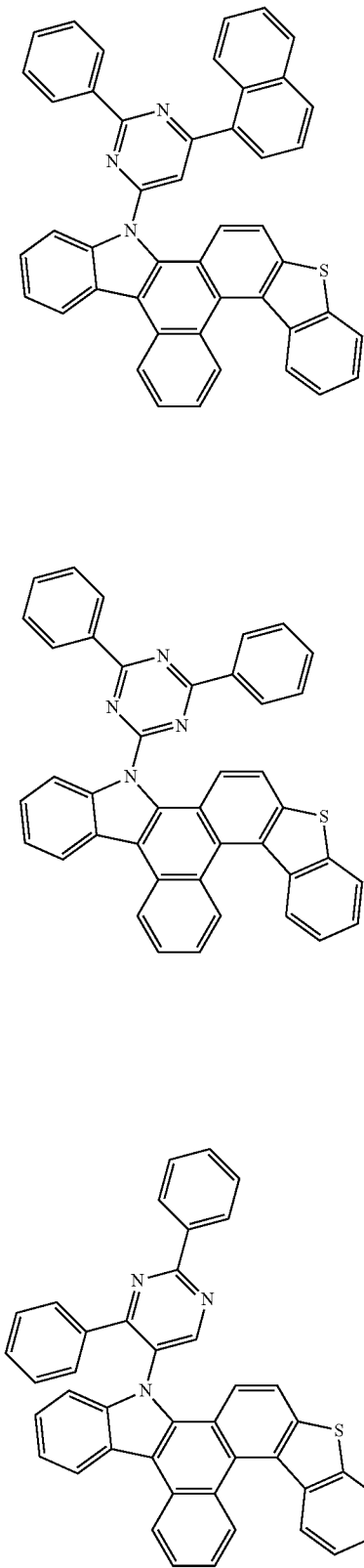

P 1-8
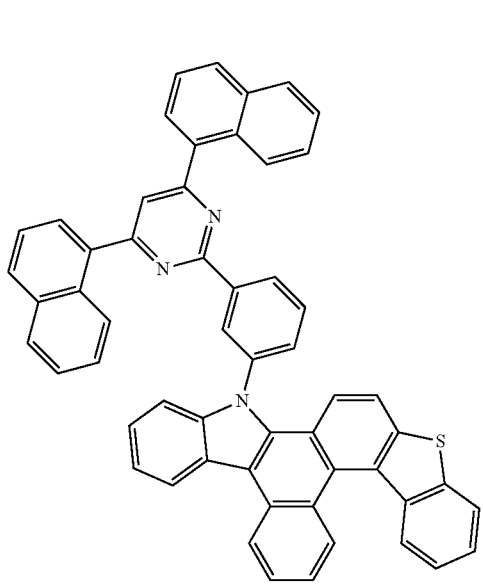
P 1-11
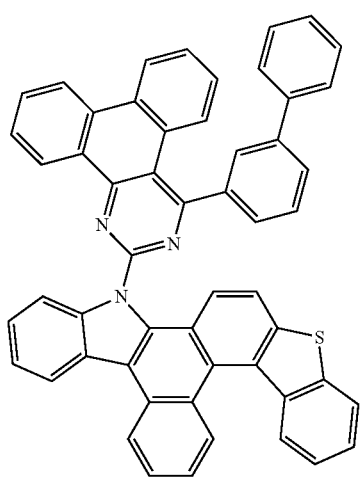
P 1-9
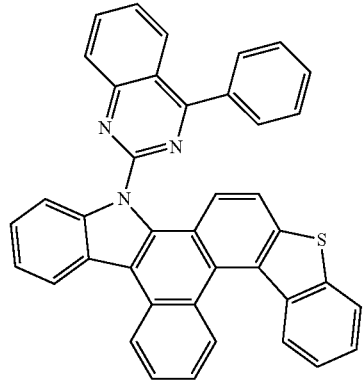
P 1-12
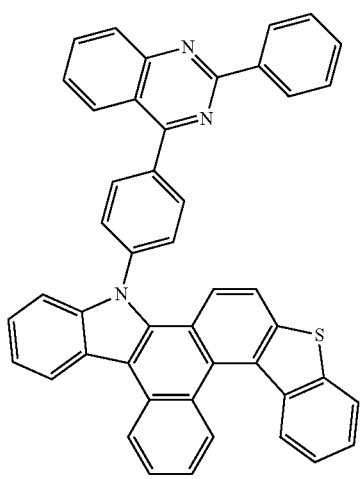
P 1-10
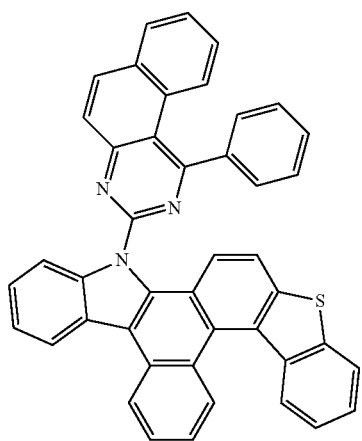
P 1-13
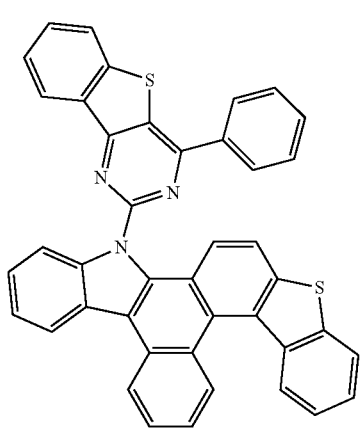

P 1-14
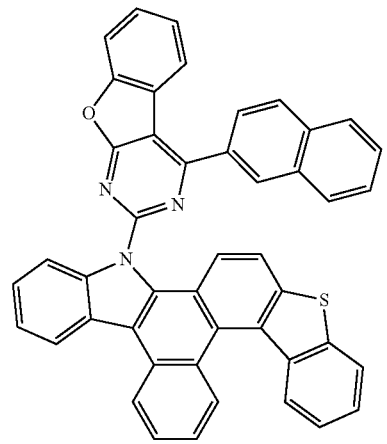
P 1-15
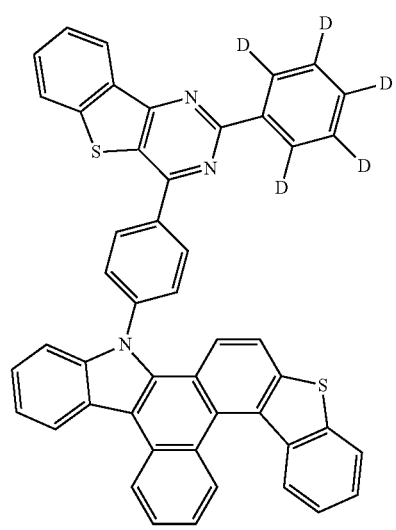
P 1-16
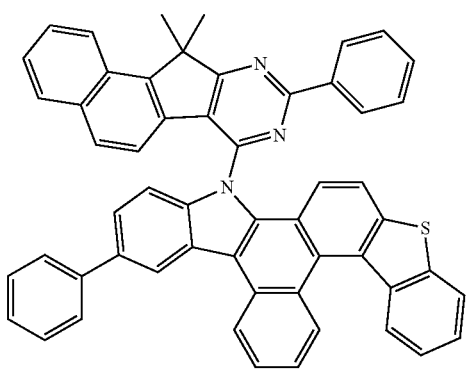
P 1-17
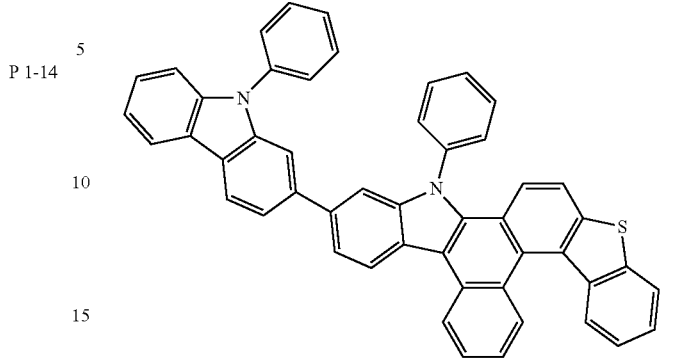
P 1-18
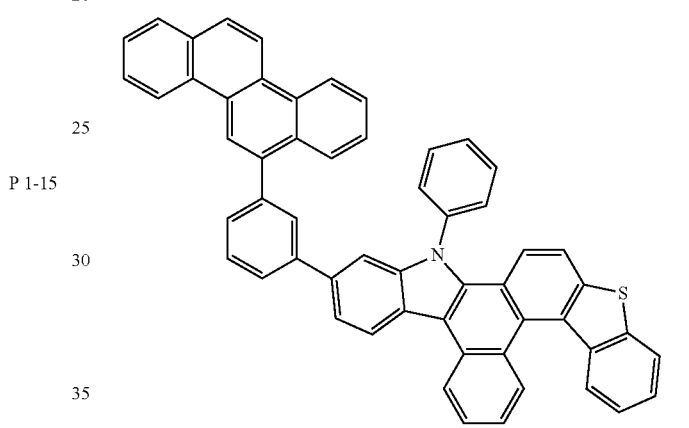
P 1-19
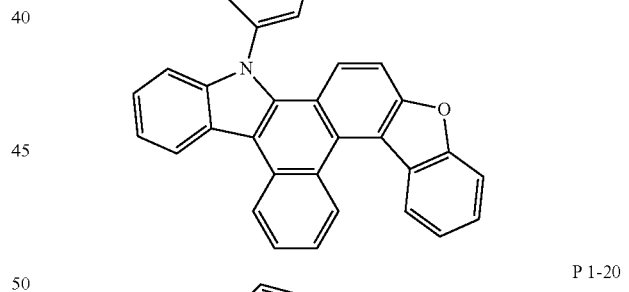
P 1-20
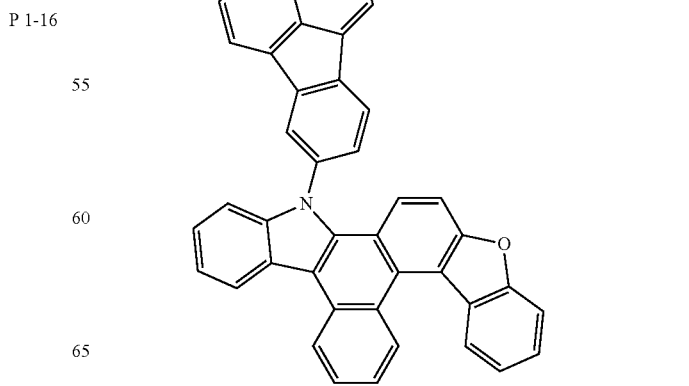

P 1-21
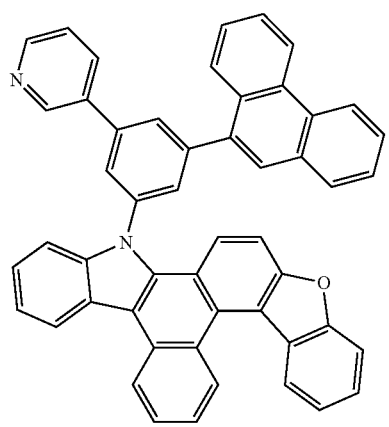
P 1-22
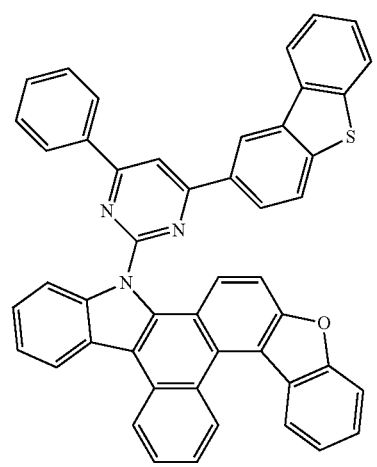
P 1-23
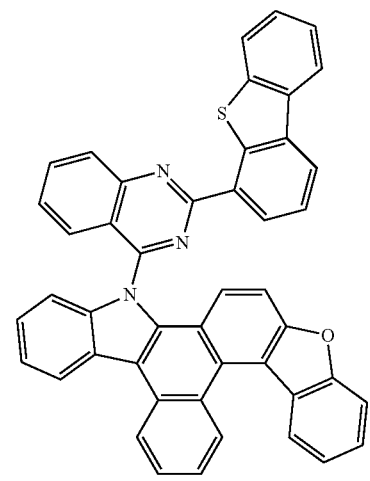
P 1-24
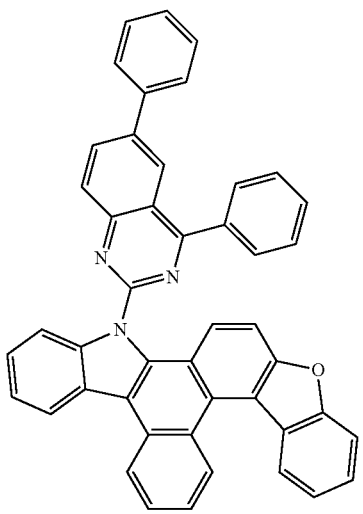
P 1-25
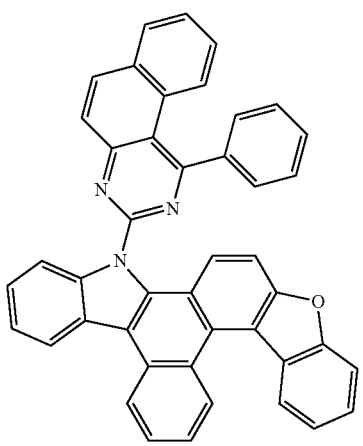
P 1-26
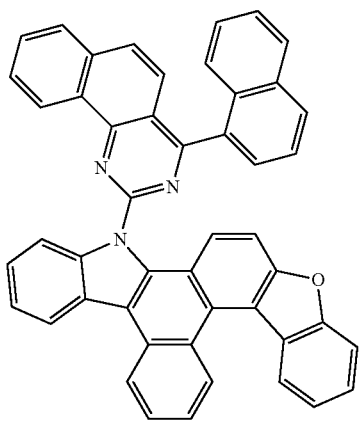

P 1-27
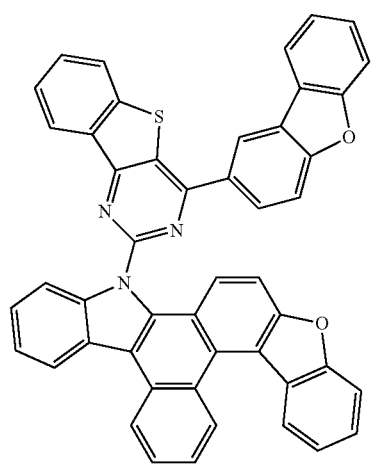
P 1-28
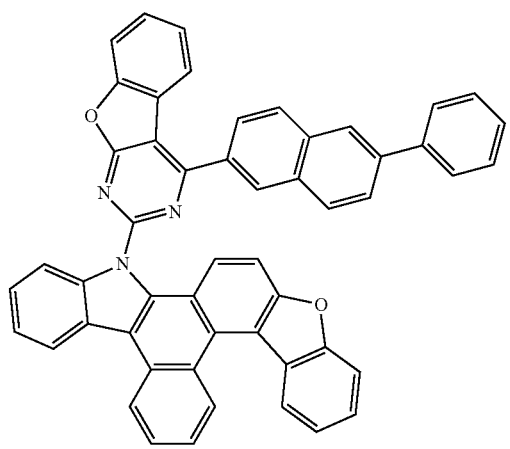
P 1-29
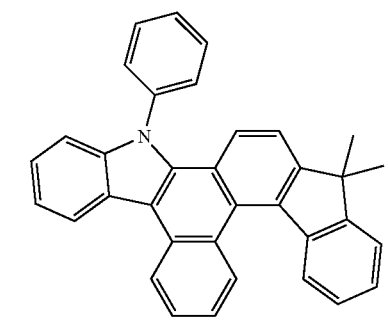
P 1-30
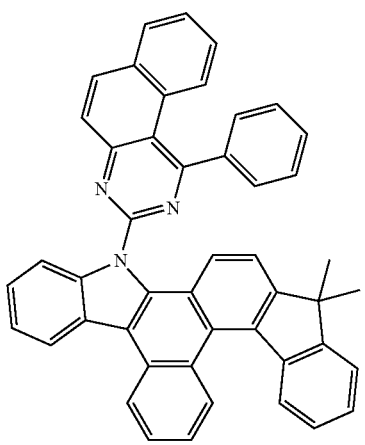
P 1-31
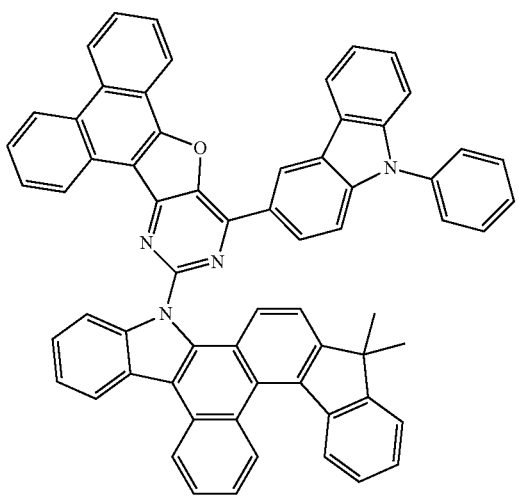
P 1-32
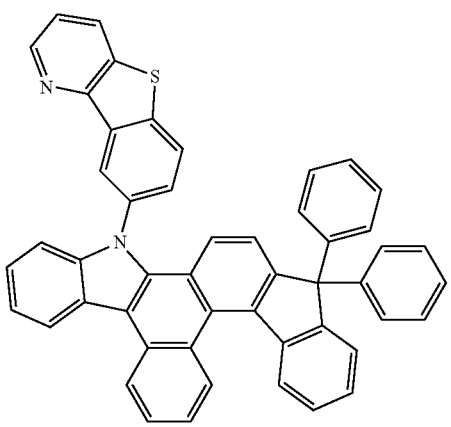

-continued
P 1-33
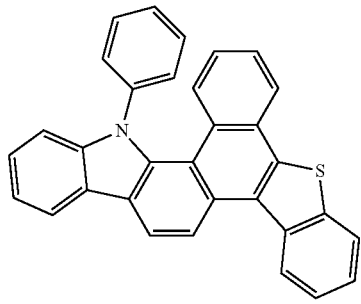
P 1-34
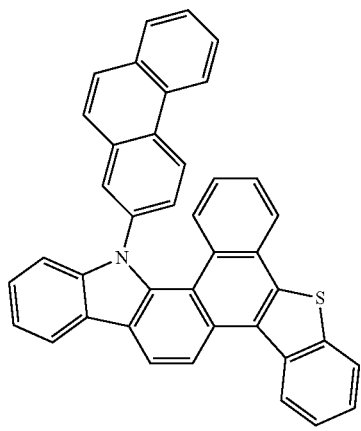
P 1-35
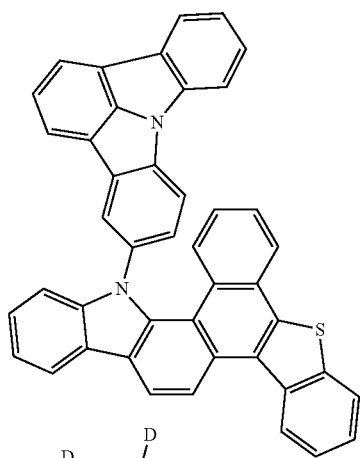
P 1-36
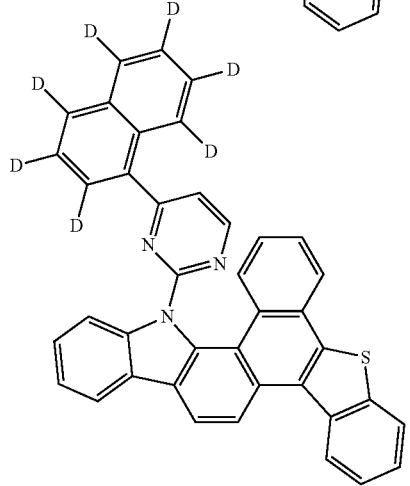
-continued
P 1-37
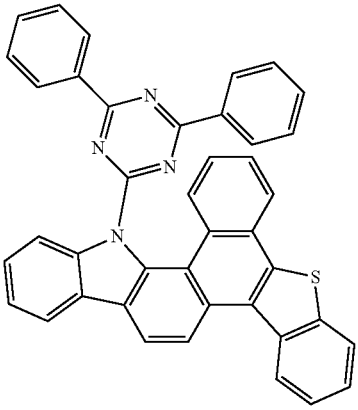
P 1-38
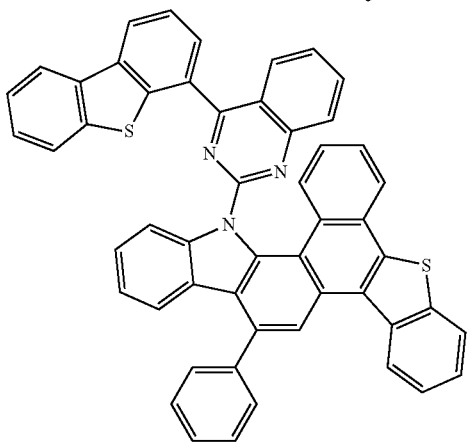
P 1-39
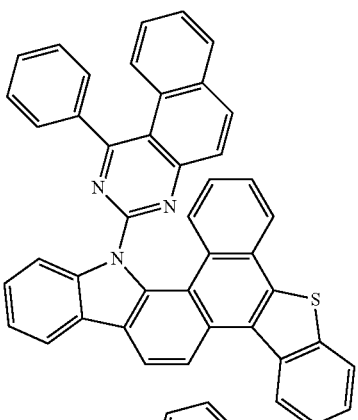
P 1-40
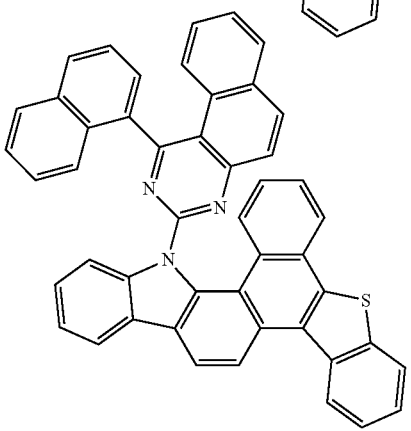

-continued
P 1-41
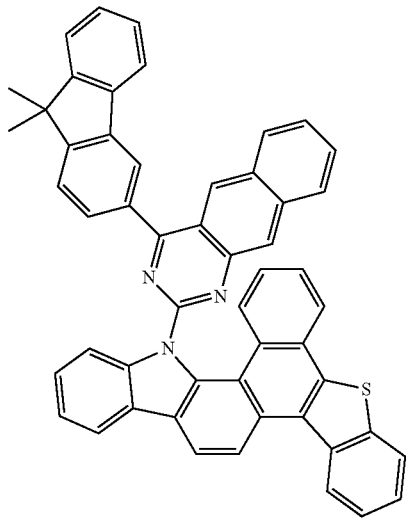
P 1-42
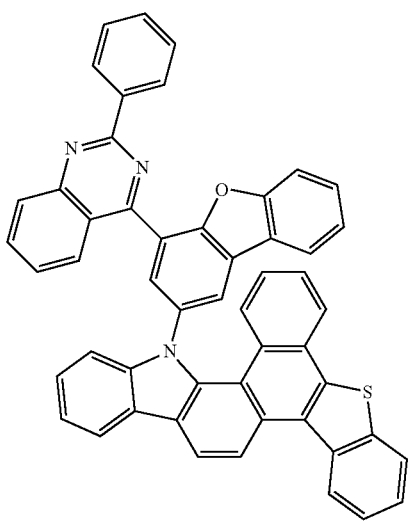
P 1-43
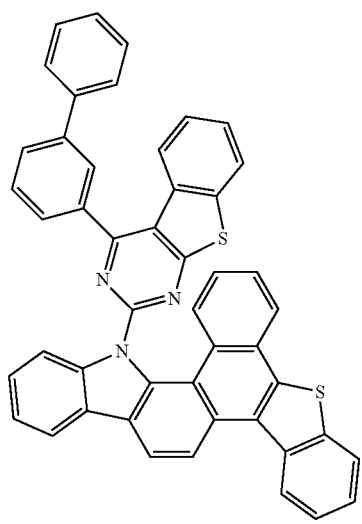
-continued
P 1-44
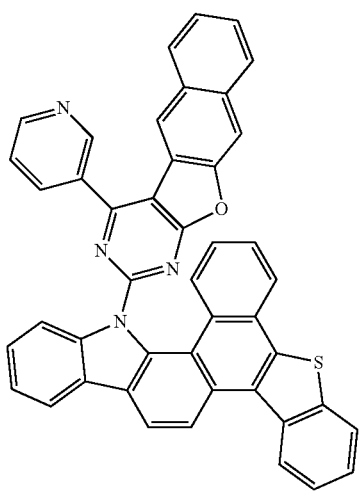
P 1-45
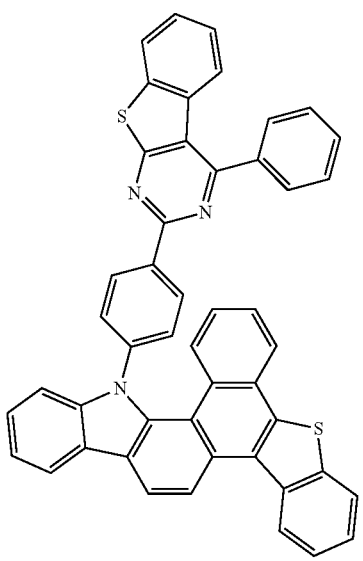
P 1-46
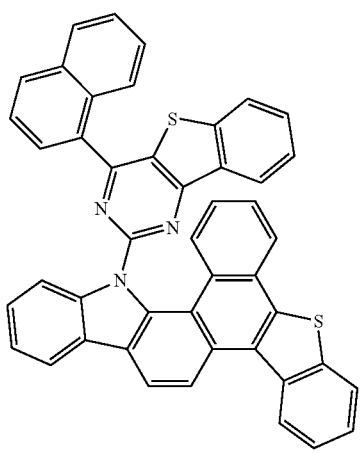

P 1-47
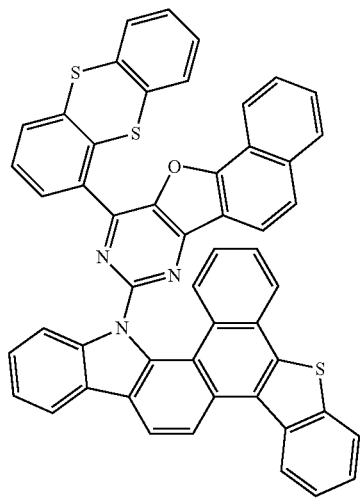
P 1-48
P 1-49
P 1-50
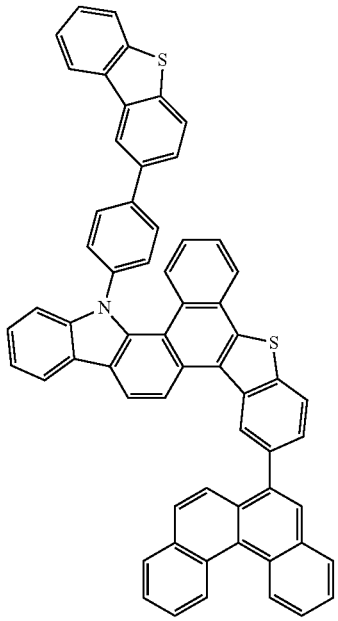
P 1-51
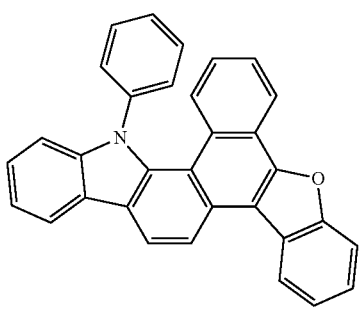
P 1-52
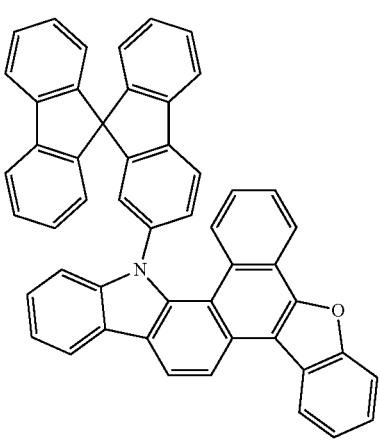

-continued
P 1-53
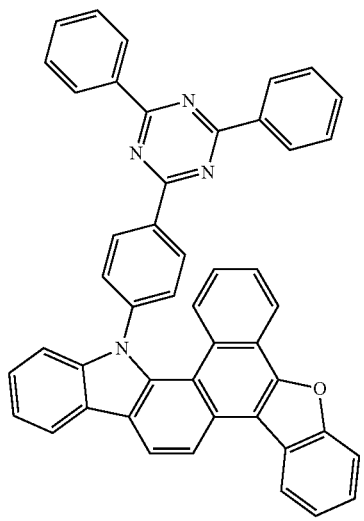
P 1-54
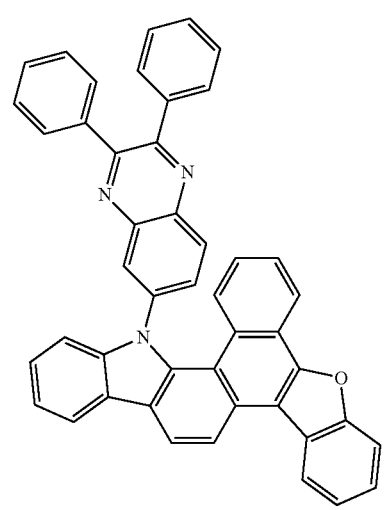
P 1-55
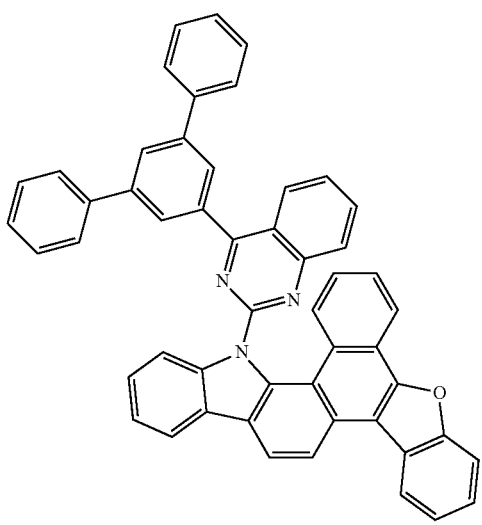
P 1-56
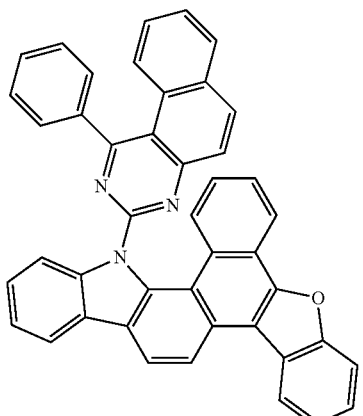
P 1-57
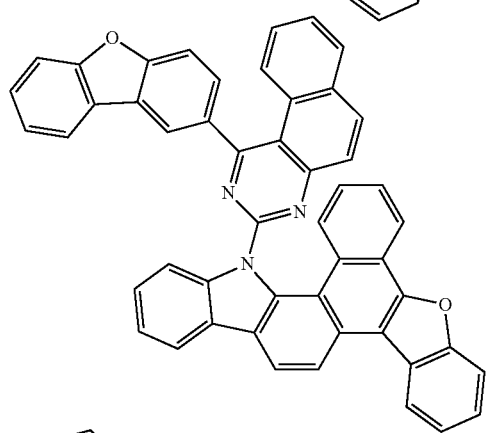
P 1-58
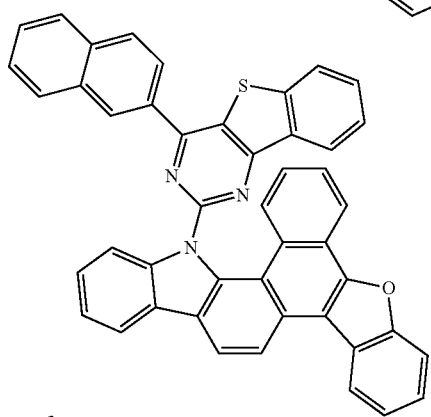
P 1-59
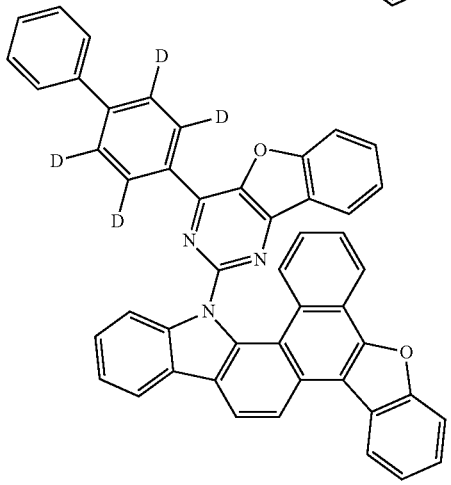

P 1-60
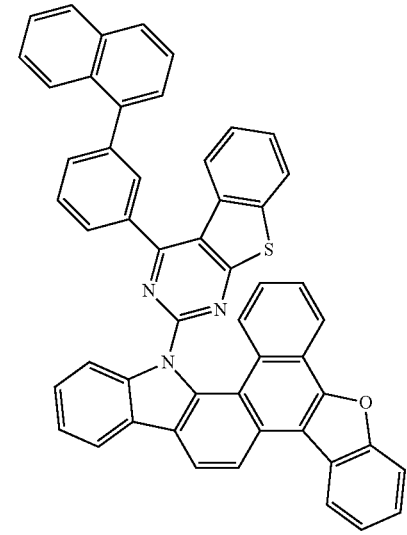
P 1-61
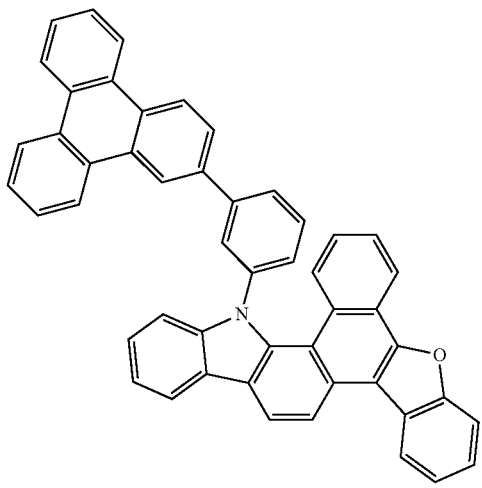
P 1-62
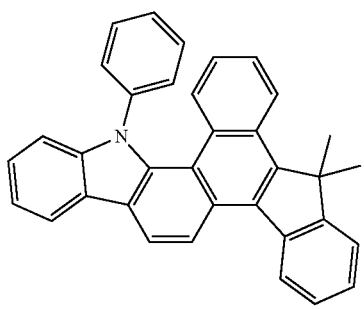
P 1-63
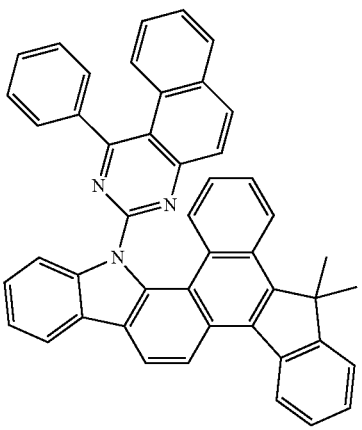
P 1-64
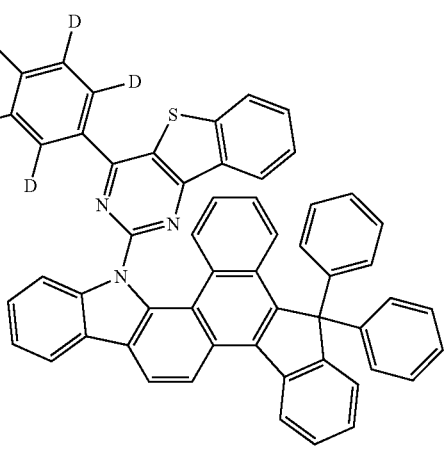
P 1-65
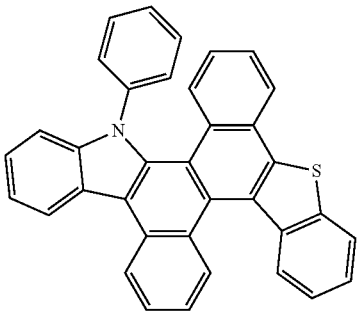
P 1-66
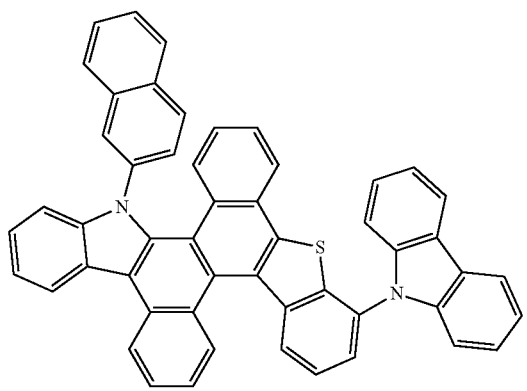

-continued
P 1-67
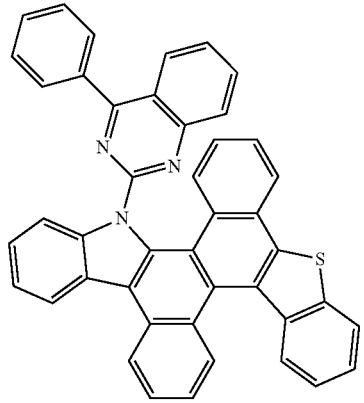
P 1-68
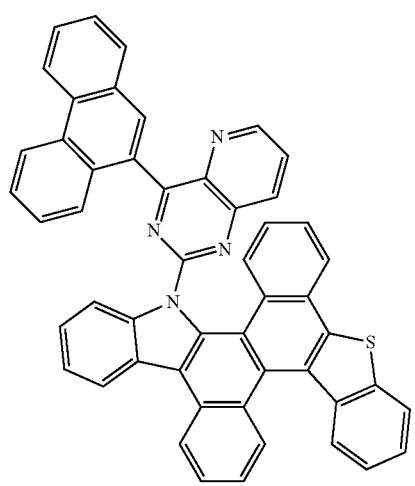
P 1-69
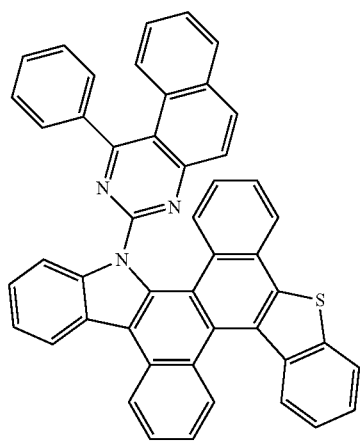
-continued
P 1-70
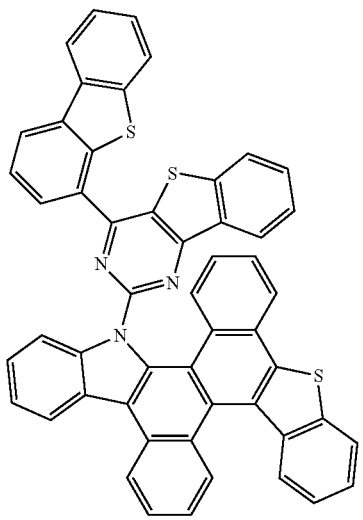
P 1-71
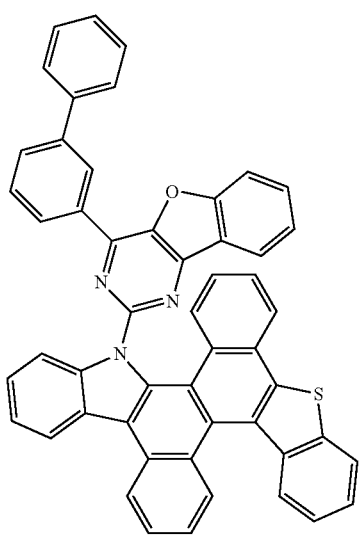
P 1-72
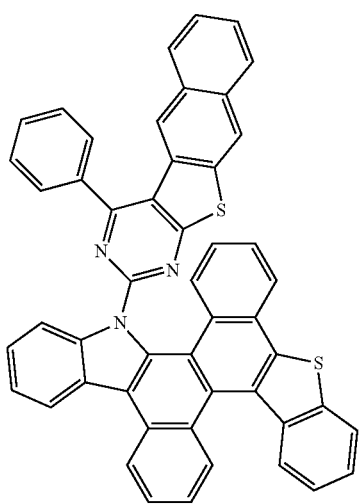

-continued
P 1-73
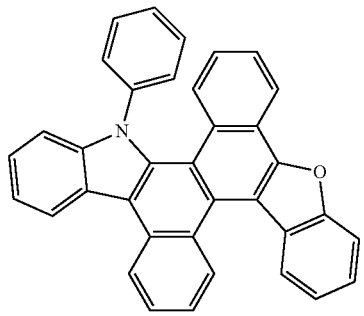
P 1-74
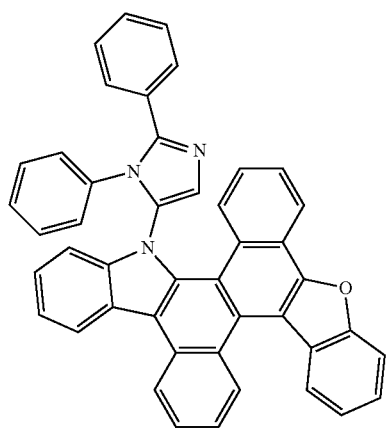
P 1-75
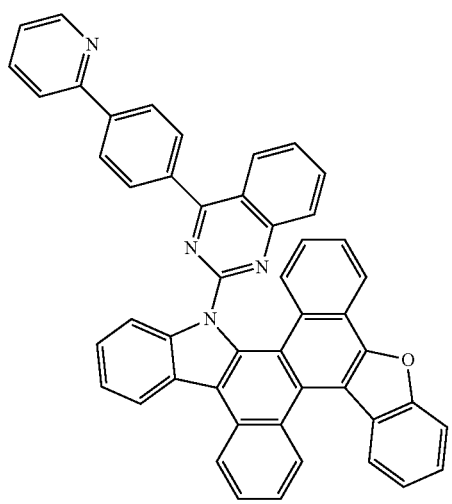
-continued
P 1-76
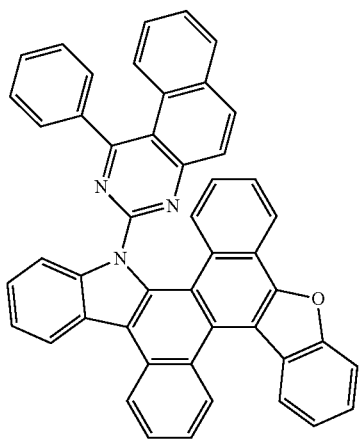
P 1-77
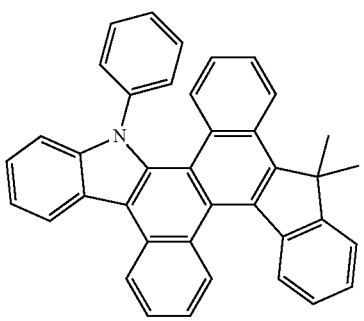
P 1-78
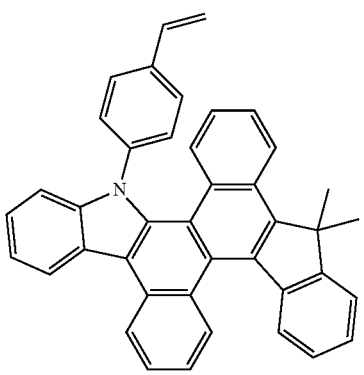
P 1-79
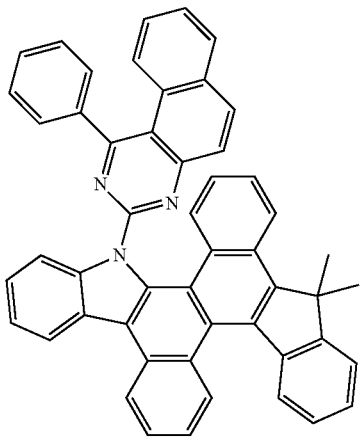

P 1-80
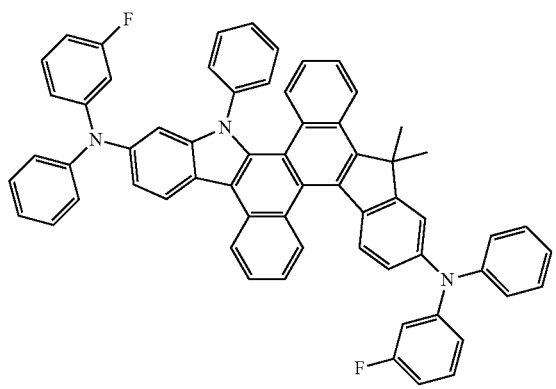
P 2-4
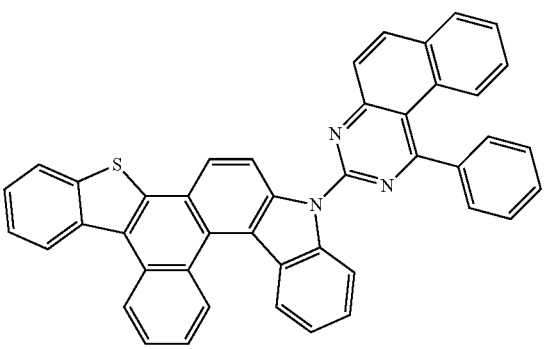
P 2-1
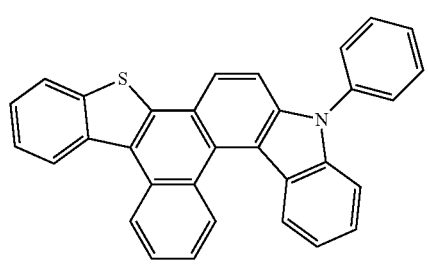
P 2-5
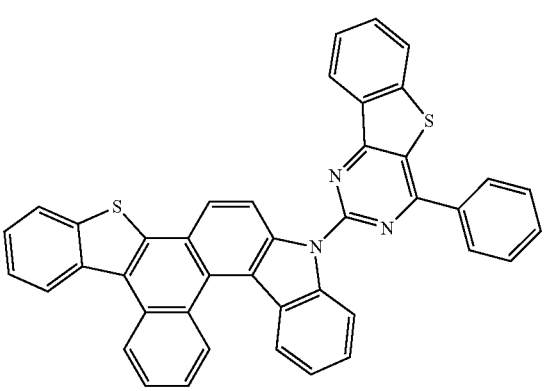
P 2-2
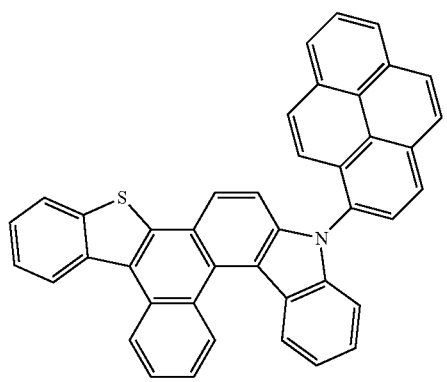
P 2-6
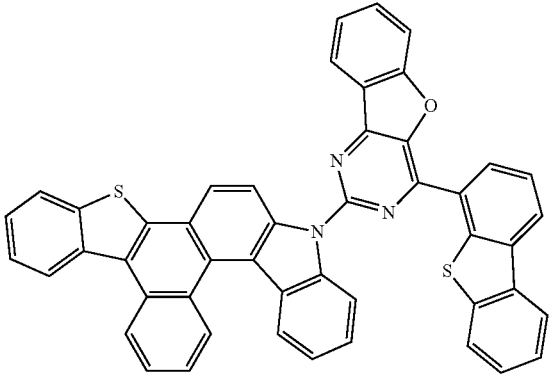
P 2-3
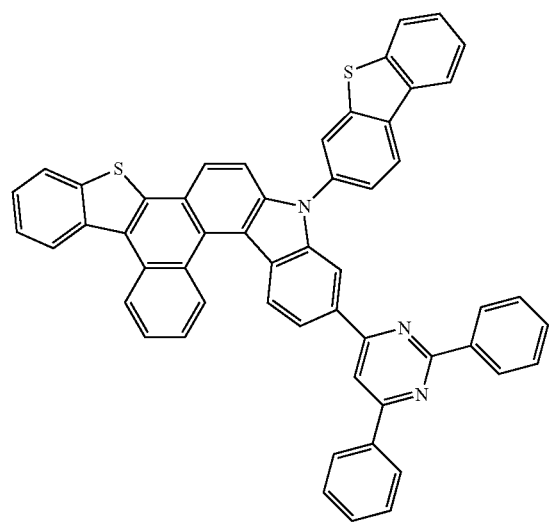
P 2-7
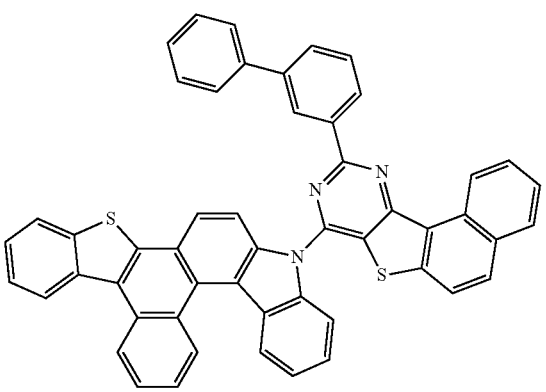

-continued
P 2-8
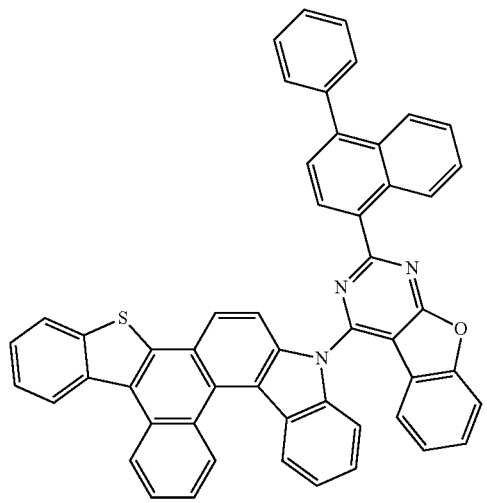
P 2-9
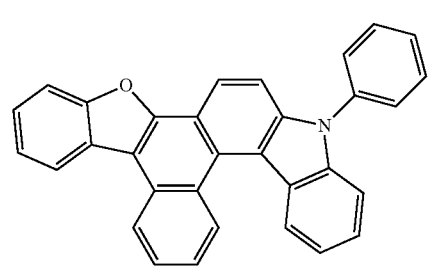
P 2-10
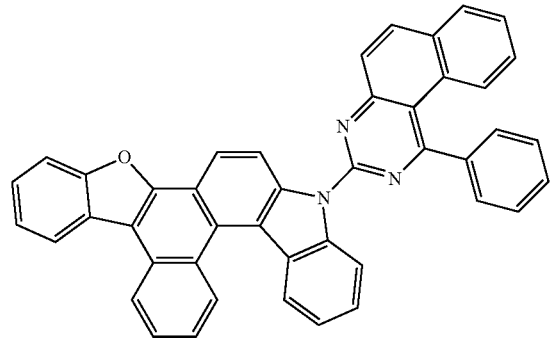
P 2-11
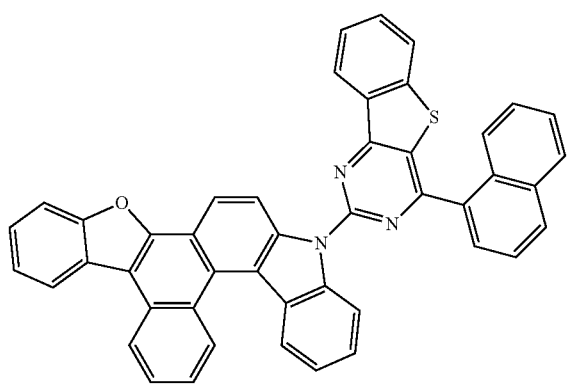
-continued
P 2-12
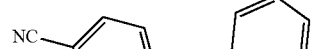
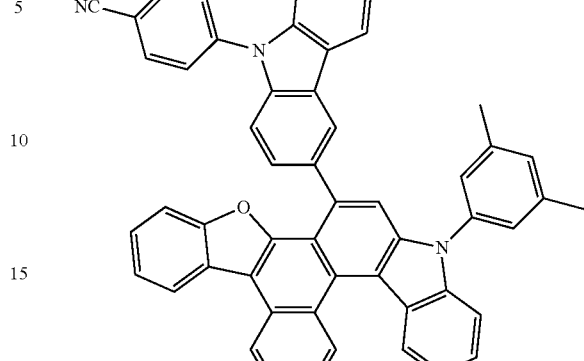
P 2-13
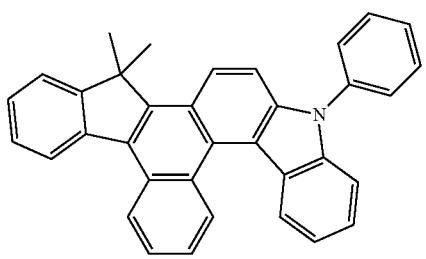
P 2-14
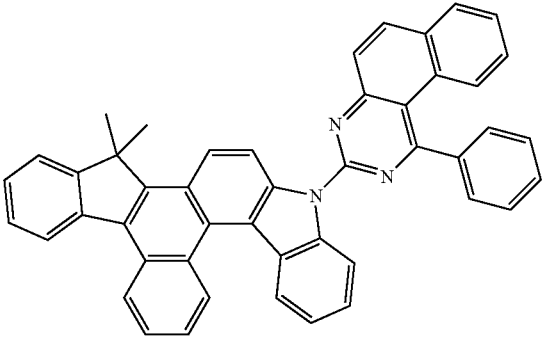
P 2-15
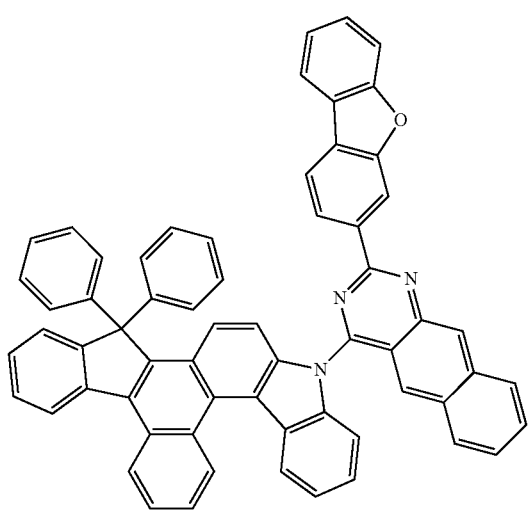

-continued
P 2-16
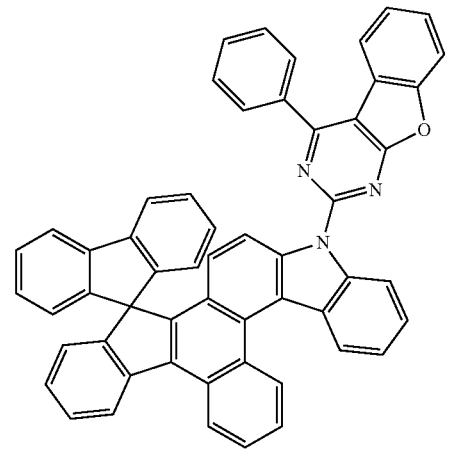
P 2-17
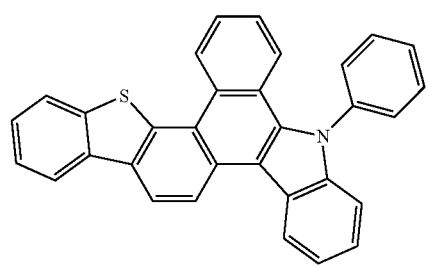
P 2-18
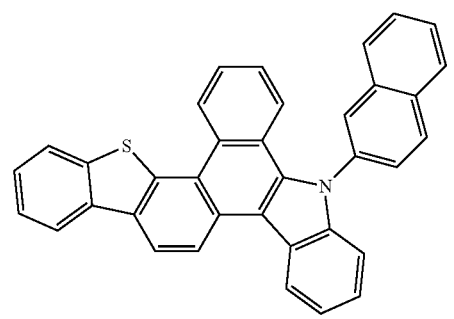
P 2-19
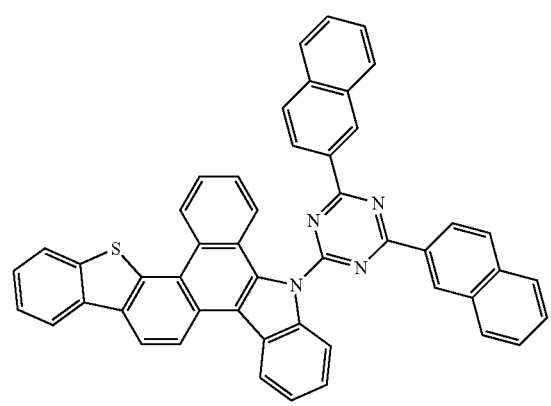
-continued
P 2-20
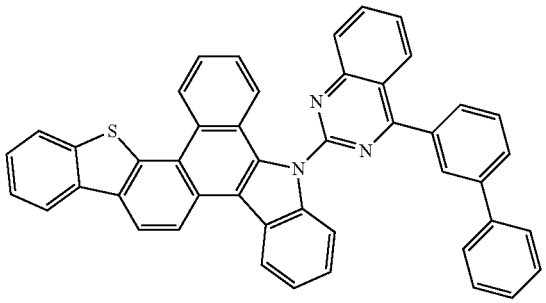
P 2-21
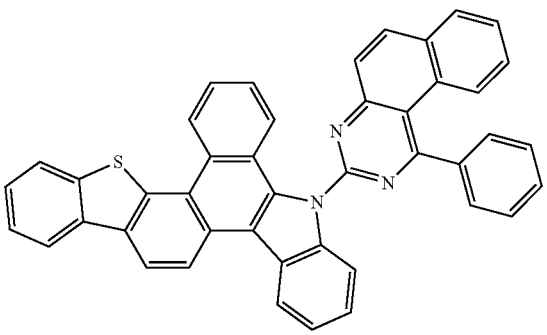
P 2-22
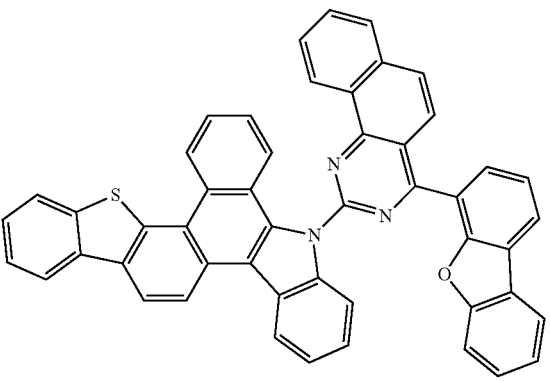
P 2-23
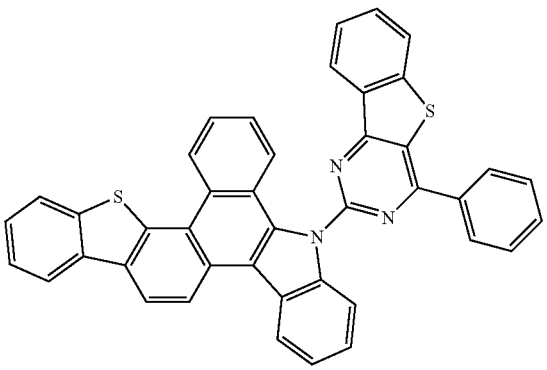

P 2-24
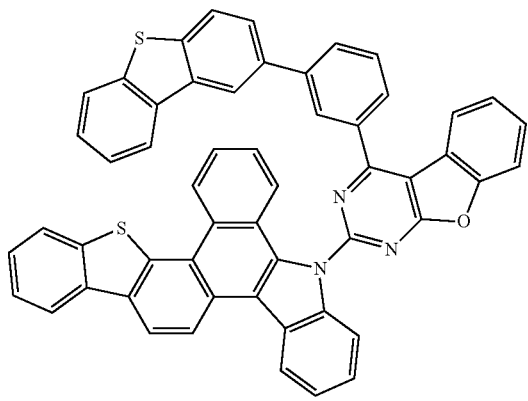
P 2-25
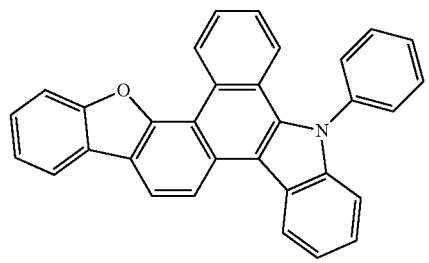
P 2-26
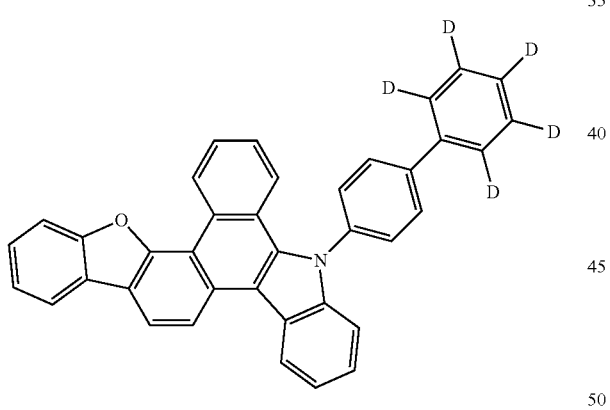
P 2-27
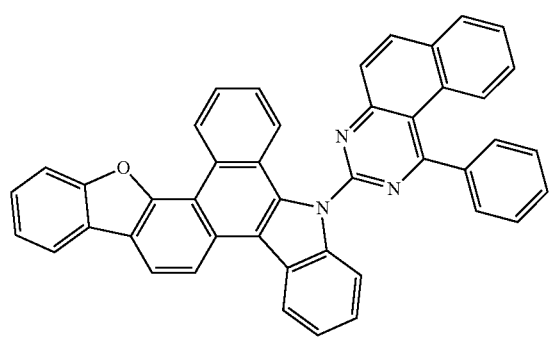
P 2-28
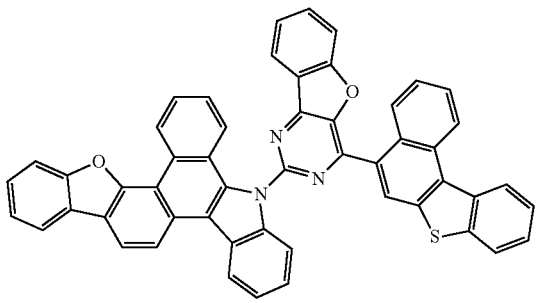
P 2-29
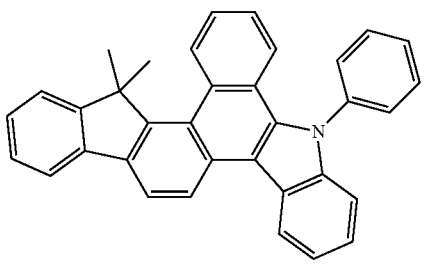
P 2-30
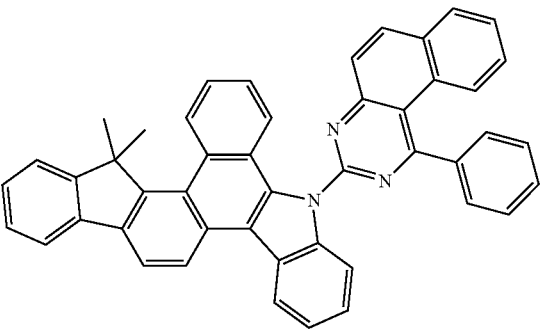
P 2-31
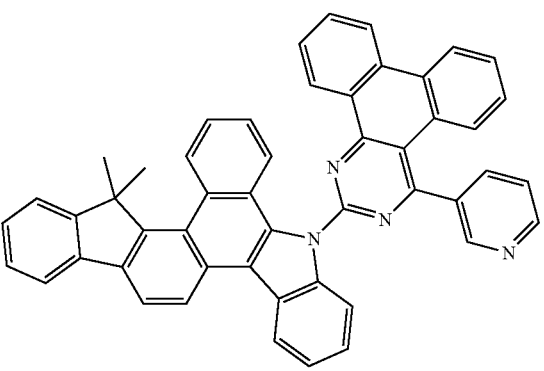

-continued
P 2-32
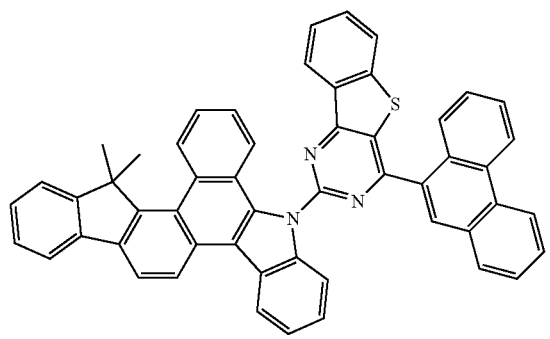
P 2-33
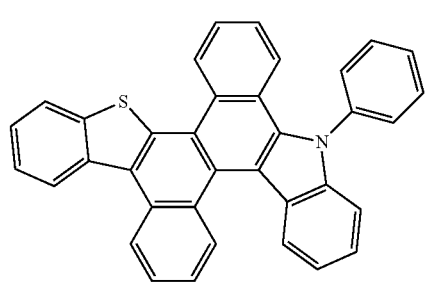
P 2-34
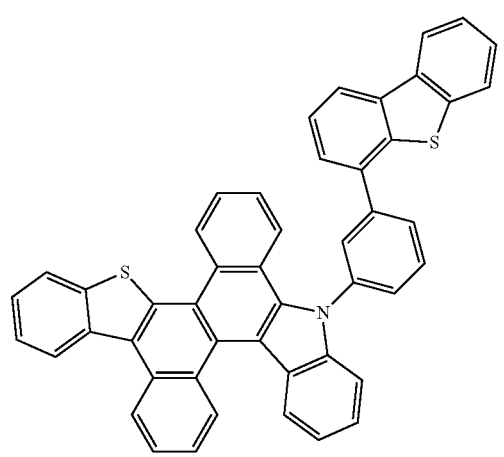
P 2-35
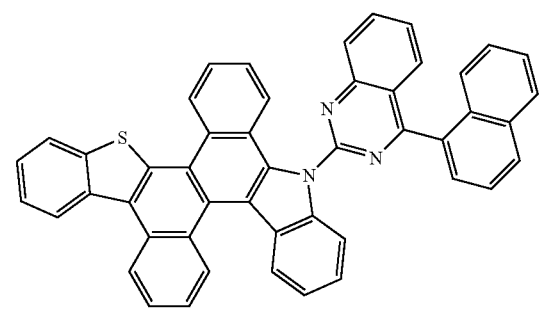
P 2-36
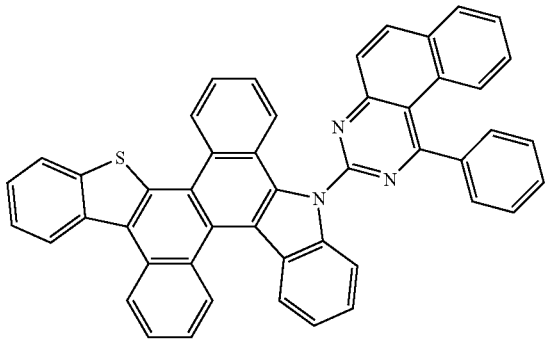
P 2-37
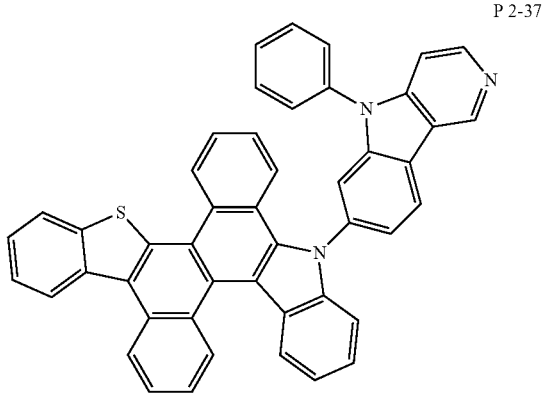
P 2-38
P 2-39
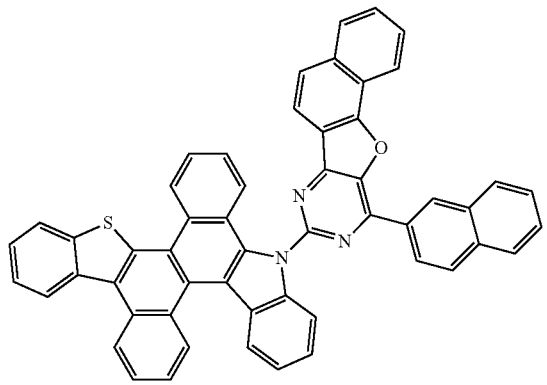

P 2-40

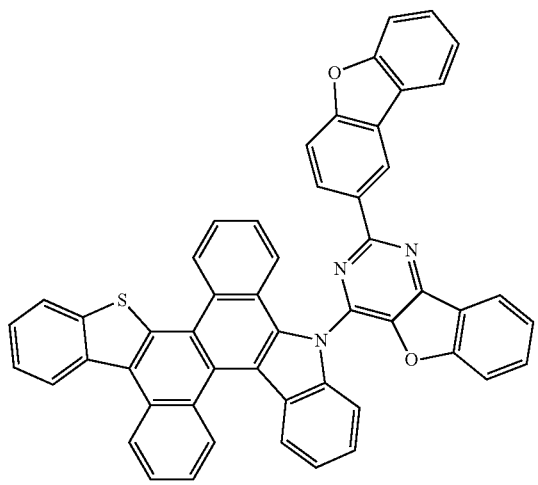

P 2-41

P 2-42

P 2-43

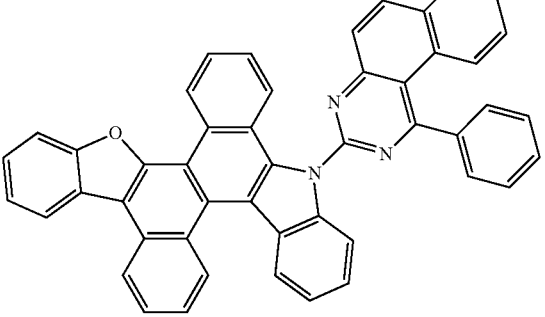

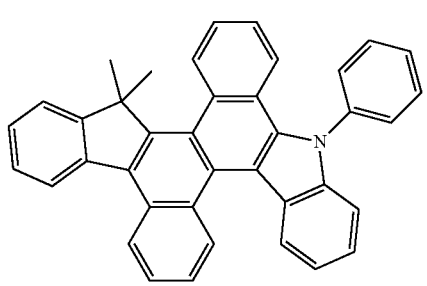

P 2-44

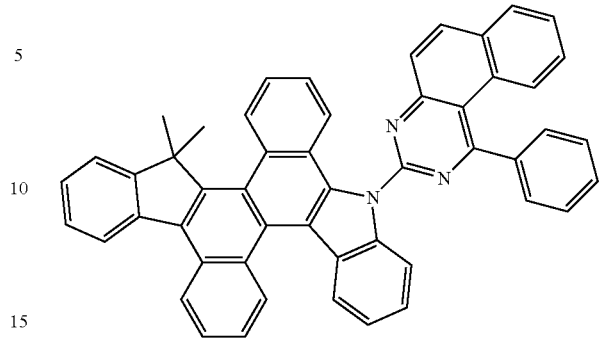

In accordance with an aspect of the present invention, the present invention provides the organic electric element comprising a first electrode, a second electrode, and an organic material layer positioned between the first electrode and the second electrode.

The organic material layer may be at least one of a hole injection layer, a hole transport layer, an emission-auxiliary layer and a light emitting layer, and the organic material layer may comprise at least one of the above compounds. That is, the organic material layer may comprise a single compound or a mixture of two or more kinds represented by the formula 1, and the compound represented by formula 1 may be used as a host material of the light emitting layer, in particular, a green phosphorescent host or a red phosphorescent host.

Hereinafter, synthesis example of the compound represented by the formula 1 according to one embodiment of the present invention and manufacturing of an organic electric element will be described in detail by way of examples. However, the present invention is not limited to the following examples.

SYNTHESIS EXAMPLE

For example, as shown the following reaction scheme 1 or 2, the compound (final products) represented by the formula 1 according to the present invention can be synthesized by reacting Sub 1A or 1B with Sub 2, but there is no limitation thereto.

<Reaction Scheme 1>

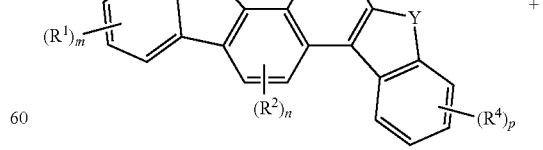

Sub 1A

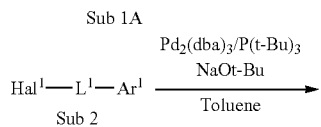

Sub 2

Final Product 1

Sub 1A

<Reaction Scheme 2>

Sub 1B

+

Sub 1B

Sub 2

Final Product 2

In the reaction schemes 1 and 2, $Hal^1$ is Br or Cl, and X, Y, $L^1$, $Ar^1$, $R^1$ to $R^4$, m, n, o and p are the same as defined in the formula 1.

I. Synthesis of Sub 1

Sub 1A and 1B in the reaction schemes 1 and 2 can be synthesized by reaction route of the following reaction scheme 3 or 4, but there is no limitation thereto.

<Reaction Scheme 3>

Sub 1-I

Sub 1

Sub 1

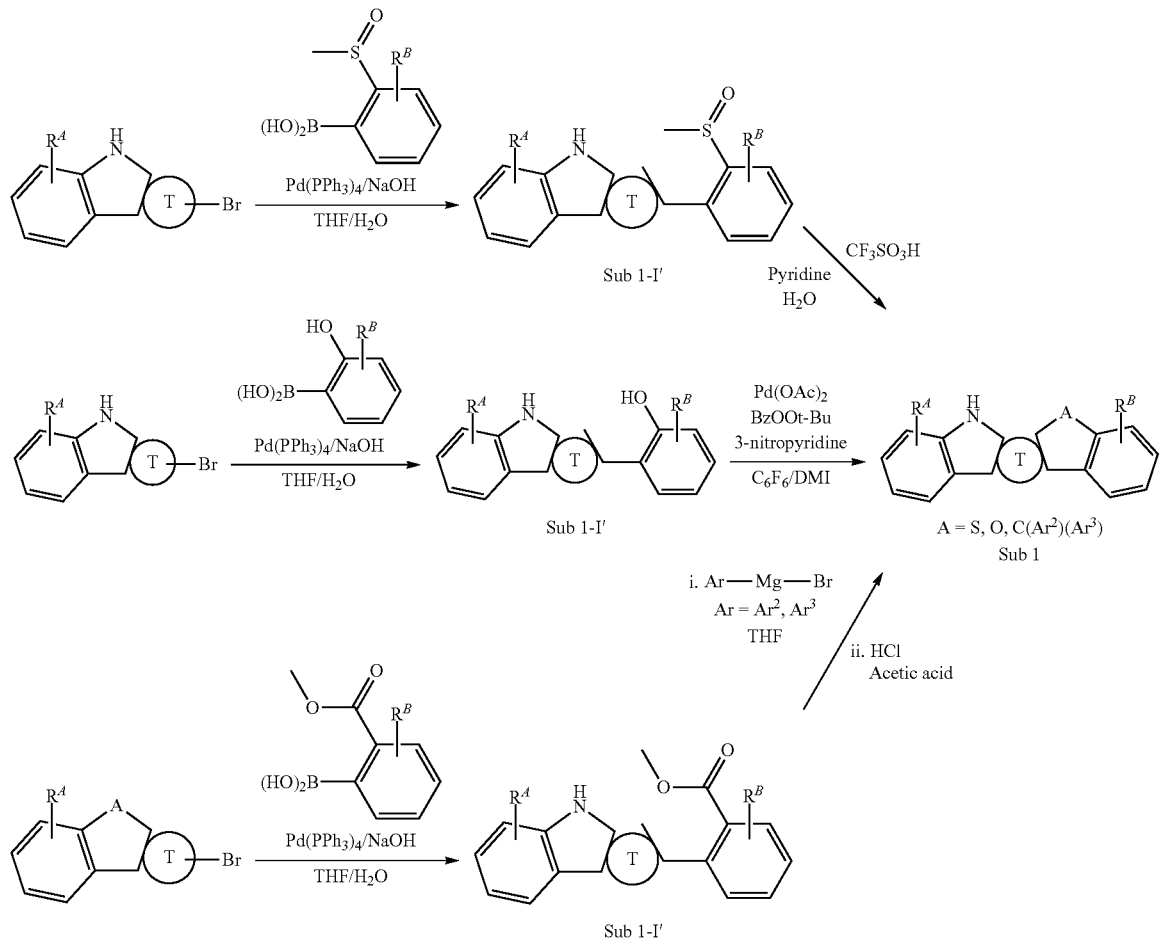

The synthesis examples of the compounds comprised in Sub 1 are as follows.

1. Synthesis Example of Sub 1A-1

<Reaction Scheme 5>

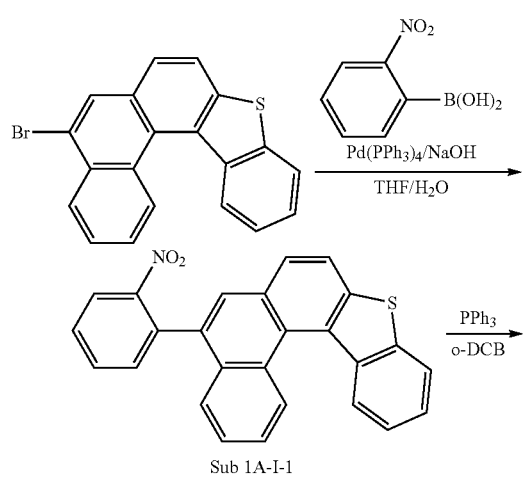

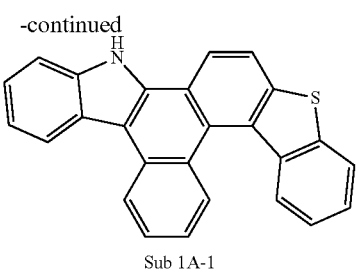
Sub 1A-1

(1) Synthesis of Sub 1A-I-1

The starting material 5-bromobenzo[b]phenanthro[4,3-d]thiophene (38.33 g, 105.51 mmol) was dissolved in THF (350 ml) in a round bottom flask and (2-nitrophenyl)boronic acid (17.61 g, 105.51 mmol), Pd(PPh$_3$)$_4$ (4.88 g, 4.22 mmol), NaOH (12.66 g, 316.54 mmol) and water (175 ml) were added to the solution. Then, the mixture was stirred at 80° C. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 35.51 g (yield: 83%) of the product.

(2) Synthesis of Sub 1A-1

Sub 1A-I-1 (35.51 g, 87.58 mmol) obtained in the synthesis above was dissolved in o-dichlorobenzene (765 ml) in a round bottom flask and triphenylphosphine (57.43 g, 218.94 mmol) was added the solution. Then, the mixture was stirred at 200° C. When the reaction was completed, o-dichlorobenzene was removed by distillation, and then the residue was extracted with CH₂Cl₂ and water. Then, the organic layer was dried with MgSO₄ and concentrated. Then the concentrate was applied to silica gel column and recrystallized to obtain 20.28 g (yield: 62%) of the product.

2. Synthesis Example of Sub 1A-8

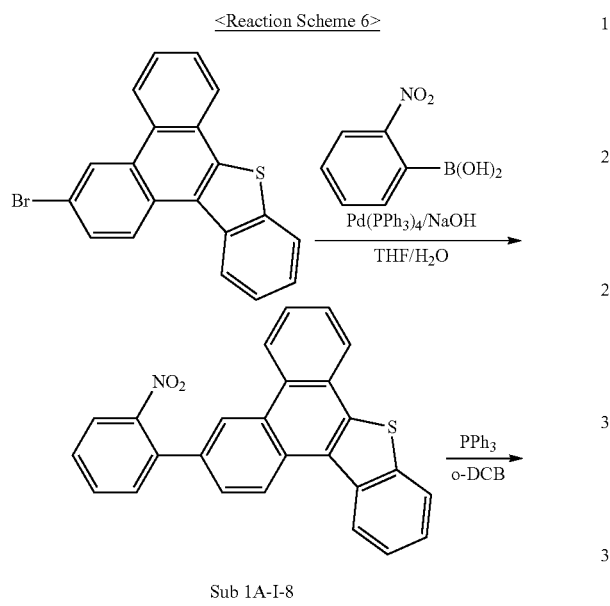

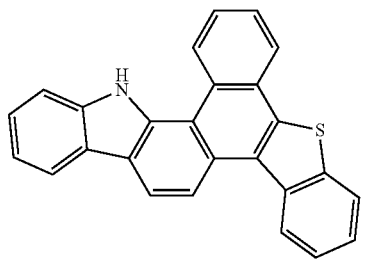

Sub 1A-8

(1) Synthesis of Sub 1A-I-8

(2-nitrophenyl)boronic acid (17.01 g, 101.88 mmol), Pd(PPh₃)₄ (4.71 g, 4.08 mmol), NaOH (12.23 g, 305.64 mmol), THF (340 ml) and water (170 ml) were added to the starting material 3-bromobenzo[b]phenanthro[9,10-d]thiophene (37.01 g, 101.88 mmol), and then 33.05 g (yield: 80%) of the product was obtained by the same method as in synthesis of Sub 1A-I-1.

(2) Synthesis of Sub 1A-8

Triphenylphosphine (53.45 g, 203.78 mmol) and o-dichlorobenzene (710 ml) were added to Sub 1A-I-8 (33.05 g, 81.51 mmol) obtained in the above synthesis, and then 19.79 g (yield: 65%) of the product was obtained by the same method as in synthesis of Sub 1A-1.

3. Synthesis Example of Sub 1A-12

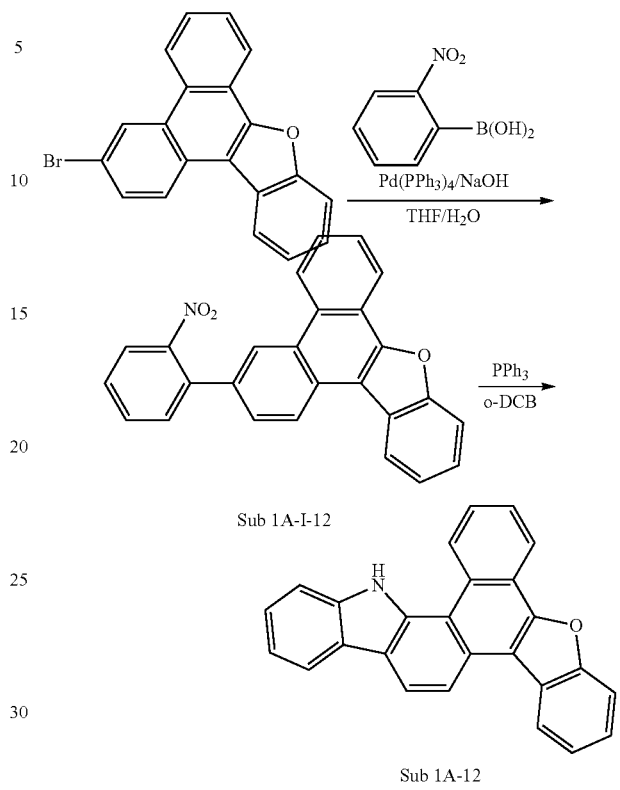

(1) Synthesis of Sub 1A-I-12

(2-nitrophenyl)boronic acid (18.12 g, 108.55 mmol), Pd(PPh₃)₄ (5.02 g, 4.34 mmol), NaOH (13.03 g, 325.66 mmol), THF (360 ml) and water (180 ml) were added to the starting material 3-bromophenanthro[9,10-b]benzofuran (37.69 g, 108.55 mmol), and then 33.82 g (yield: 80%) of the product was obtained by the same method as in synthesis of Sub 1A-I-1.

(2) Synthesis of Sub 1A-12

Triphenylphosphine (54.69 g, 208.52 mmol) and o-dichlorobenzene (730 ml) were added to Sub 1A-I-12 (33.82 g, 83.41 mmol) obtained in the above synthesis, and then 19.08 g (yield: 64%) of the product was obtained by the same method as in synthesis of Sub 1A-1.

4. Synthesis Example of Sub 1A-19

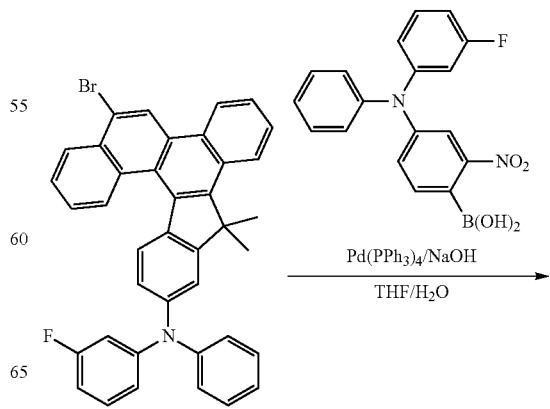

-continued

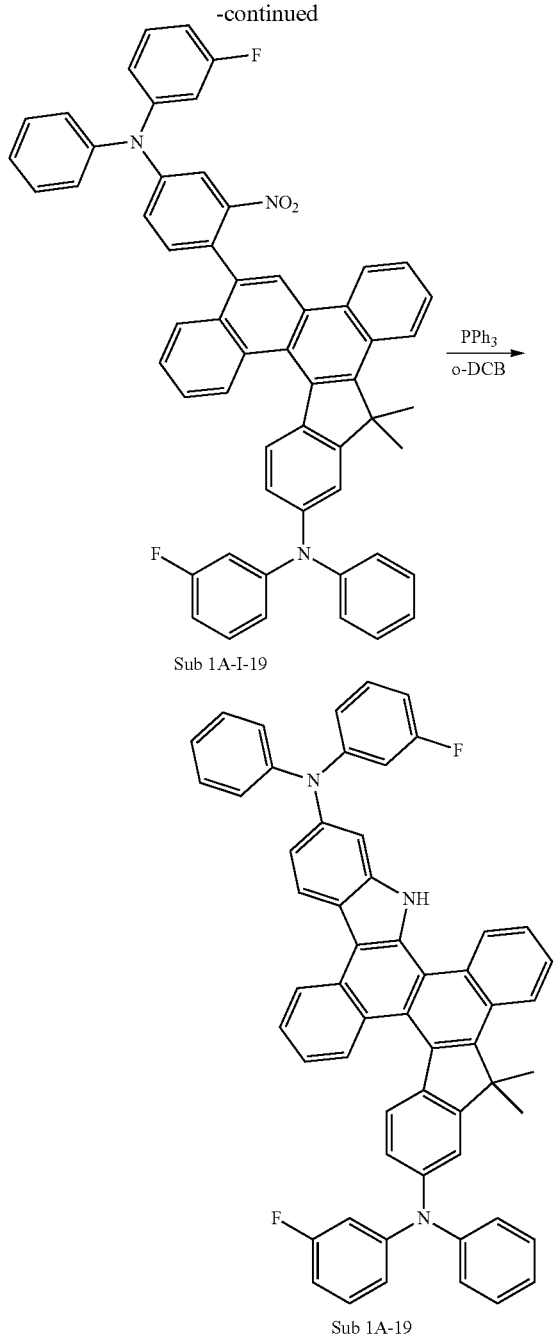

Sub 1A-I-19

Sub 1A-19

(1) Synthesis of Sub 1A-I-19

(4-((3-fluorophenyl)(phenyl)amino)-2-nitrophenyl)boronic acid (19.00 g, 53.97 mmol), Pd(PPh₃)₄ (2.49 g, 2.16 mmol), NaOH (6.48 g, 161.90 mmol), THF (180 ml) and water (90 ml) were added to the starting material 5-bromo-N-(3-fluorophenyl)-11,11-dimethyl-N-phenyl-11H-indeno[1,2-g]chrysen-13-amine (32.84 g, 53.97 mmol), and then 30.68 g (yield: 68%) of the product was obtained by the same method as in synthesis of Sub 1A-I-1.

(2) Synthesis of Sub 1A-19

Triphenylphosphine (24.07 g, 91.75 mmol) and o-dichlorobenzene (320 ml) were added to Sub 1A-I-19 (30.68 g, 36.70 mmol) obtained in the above synthesis, and then 15.05 g (yield: 51%) of the product was obtained by the same method as in synthesis of Sub 1A-1.

5. Synthesis Example of Sub 1B-5

<Reaction Scheme 9>

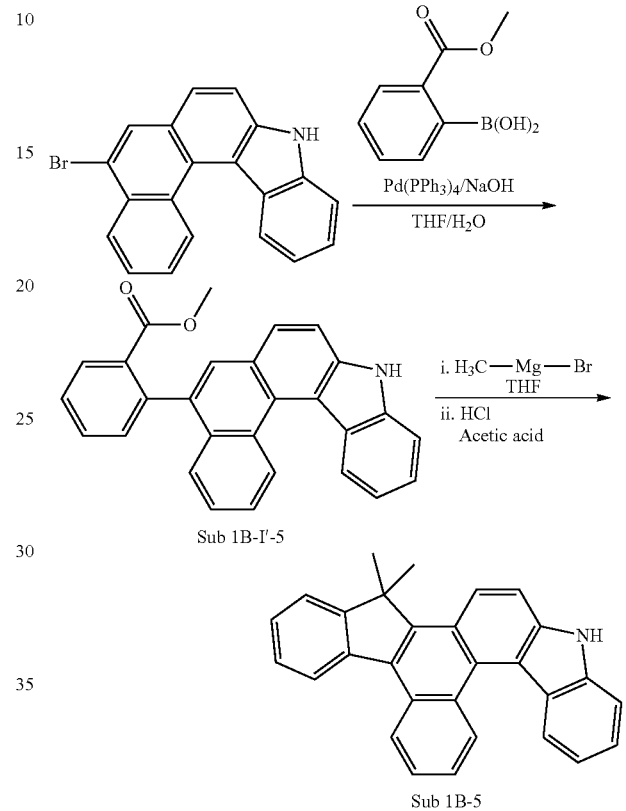

Sub 1B-I'-5

Sub 1B-5

(1) Synthesis of Sub 1B-I'-5

(2-(methoxycarbonyl)phenyl)boronic acid (14.79 g, 82.17 mmol), Pd(PPh₃)₄ (3.80 g, 3.29 mmol), NaOH (9.86 g, 246.52 mmol), THF (280 ml) and water (140 ml) were added to the starting material 5-bromo-9H-naphtho[2,1-c]carbazole (28.45 g, 82.17 mmol), and then 24.41 g (yield: 74%) of the product was obtained by the same method as in synthesis of Sub 1A-I-1.

(2) Synthesis of Sub 1B-5

Sub 1B-I'-5 (24.41 g, 60.80 mmol) obtained in the above synthesis was dissolved in THF (305 ml) in a round bottom flask and methyl magnesium bromide 1.0M in THF (243.2 ml, 243.21 mmol) was slowly added to the solution. Then, the mixture was stirred at room temperature. When the reaction was completed, the reaction product was extracted with diethyl ether and water. Then, the organic layer was dried with MgSO₄ and concentrated to obtain the intermediate. Then, the intermediate was dissolved in acetic acid solution (250 ml) and HCl (5 ml) was added the solution. Then, the mixture was refluxed. When the reaction was completed, water was added and then followed by stirring the mixture. Then, the obtained solid was filtered under reduced pressure and washed with water and methanol to obtain 17.72 g (yield: 76% over two steps) of the product being white powder.

6. Synthesis Example of Sub 1B-9

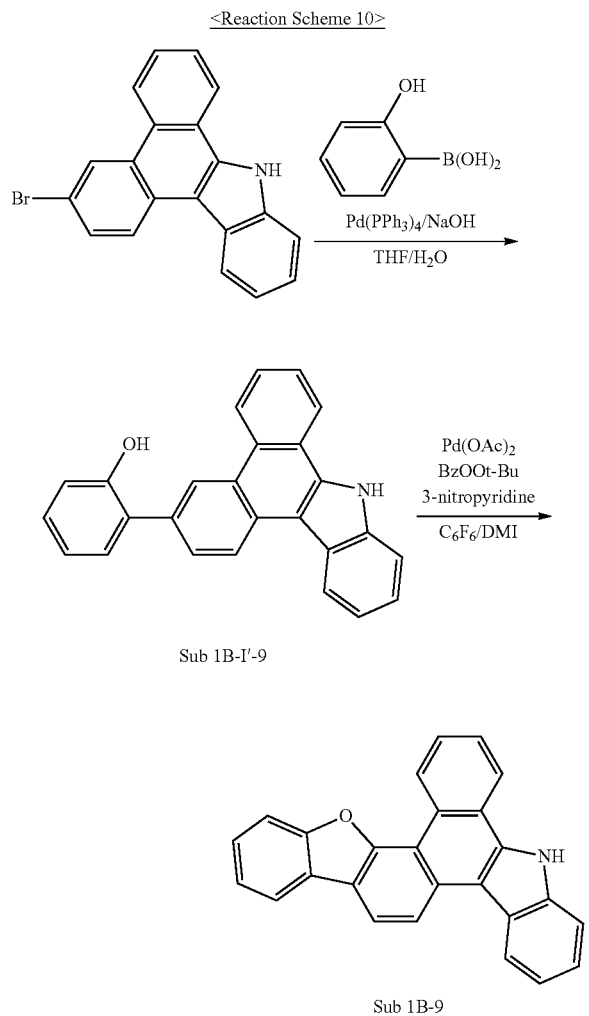

Sub 1B-I'-9

Sub 1B-9

(1) Synthesis of Sub 1B-I'-9

(2-hydroxyphenyl)boronic acid (21.09 g, 152.91 mmol), Pd(PPh$_3$)$_4$ (7.07 g, 6.12 mmol), NaOH (18.35 g, 458.73 mmol), THF (510 ml) and water (255 ml) were added to the starting material 3-bromo-9H-dibenzo[a,c]carbazole (52.94 g, 152.91 mmol), and then 36.27 g (yield: 66%) of the product was obtained by the same method as in synthesis of Sub 1A-I-1.

(2) Synthesis of Sub 1B-9

Sub 1B-I'-9 (36.27 g, 100.91 mmol) obtained in the above synthesis was placed in a round bottom flask together with Pd(OAc)$_2$ (2.27 g, 10.09 mmol) and 3-nitropyridine (1.25 g, 10.09 mmol), and the mixture was dissolved in C$_6$F$_6$ (150 ml) and DMI (100 ml). Then, tert-butyl peroxybenzoate (39.20 g, 201.83 mmol) was added to the solution, and followed by stirring the mixture at 90° C. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 16.95 g (yield: 47%) of the product.

7. Synthesis Example of Sub 1B-11

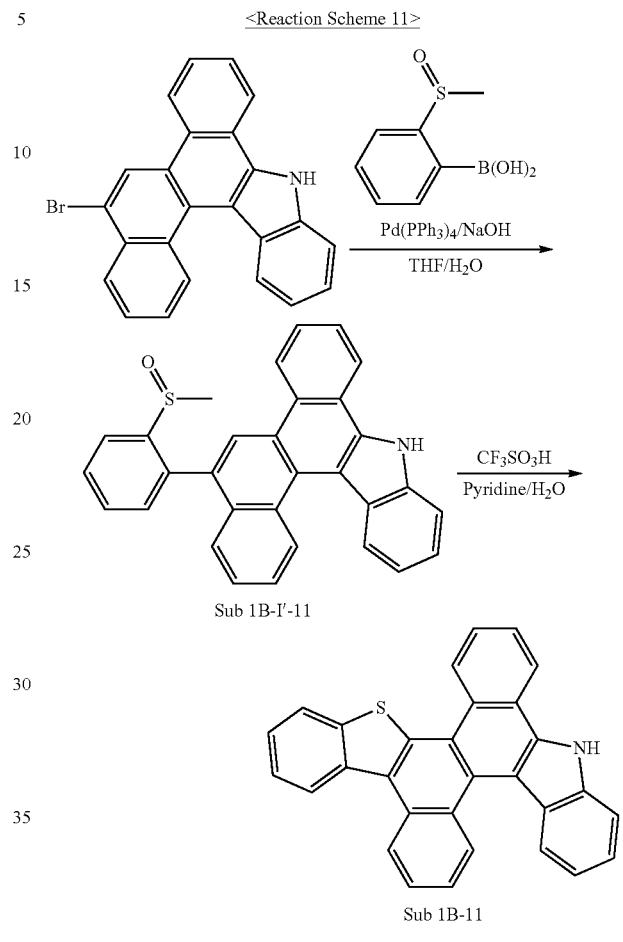

Sub 1B-I'-11

Sub 1B-11

(1) Synthesis of Sub 1B-I'-11

(2-(methylsulfinyl)phenyl)boronic acid (18.94 g, 102.91 mmol), Pd(PPh$_3$)$_4$ (4.76 g, 4.12 mmol), NaOH (12.35 g, 308.72 mmol), THF (340 ml) and water (170 ml) were added to the starting material 5-bromo-11H-benzo[a]naphtho[2,1-c]carbazole (40.78 g, 102.91 mmol), and then 24.38 g (yield: 52%) of the product was obtained by the same method as in synthesis of Sub 1A-I-1.

(2) Synthesis of Sub 1B-11

Sub 1B-I'-11 (24.38 g, 53.52 mmol) obtained in the above synthesis was placed in a round bottom flask together with triflic acid (71 ml, 802.73 mmol), and then the mixture was stirred at room temperature for 24 hours. Then, the pyridine solution (940 ml, pyridine:H$_2$O=1:5) was dropped slowly to the mixture, and then the mixture was stirred for 30 minutes under refluxing. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 14.28 g (yield: 63%) of the product.

The compound belonging to Sub 1 may be the following compounds, but there is no limitation thereto. Table 1 shows FD-MS (Field Desorption-Mass Spectrometry) values of some compounds belonging to Sub 1.

Sub 1A-1
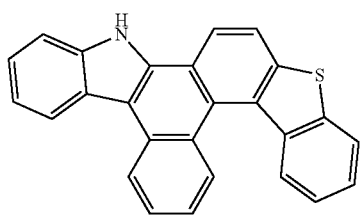
Sub 1A-6
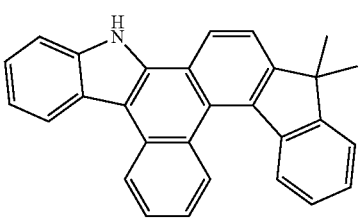
Sub 1A-2
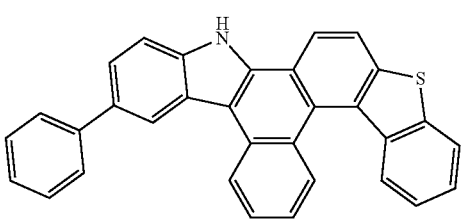
Sub 1A-7
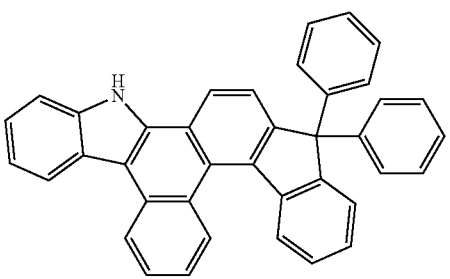
Sub 1A-3
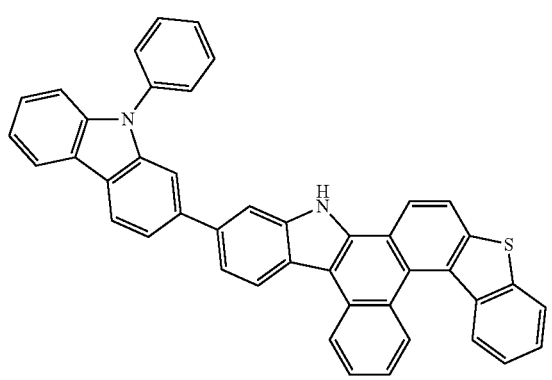
Sub 1A-8
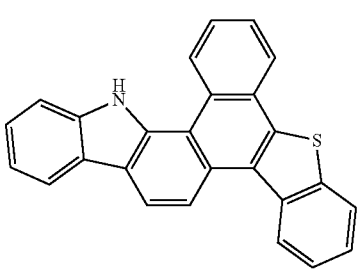
Sub 1A-9
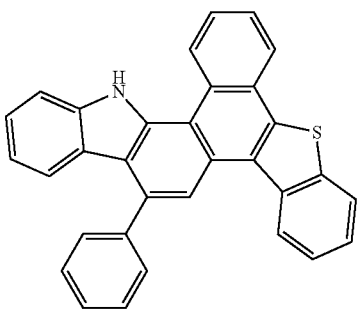
Sub 1A-4
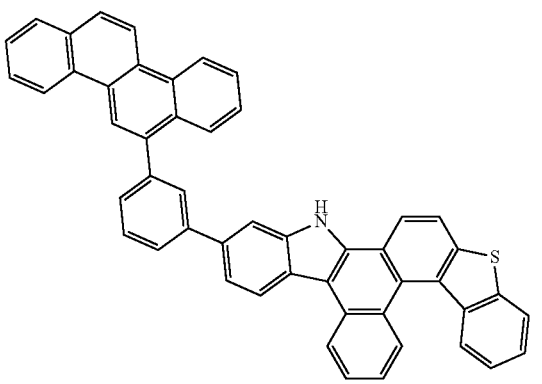
Sub 1A-10
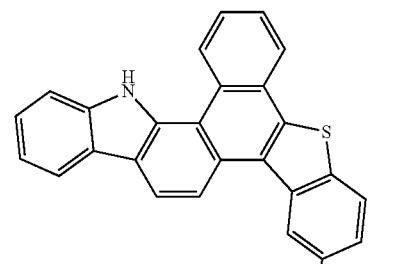
Sub 1A-5
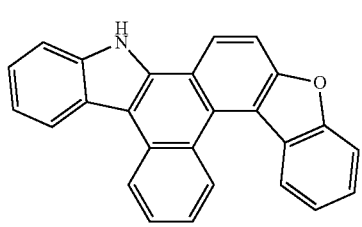
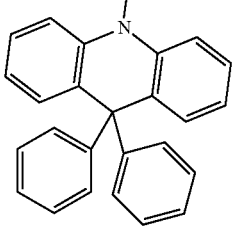

-continued
Sub 1A-11
Sub 1A-12
Sub 1A-13
Sub 1A-14
Sub 1A-15
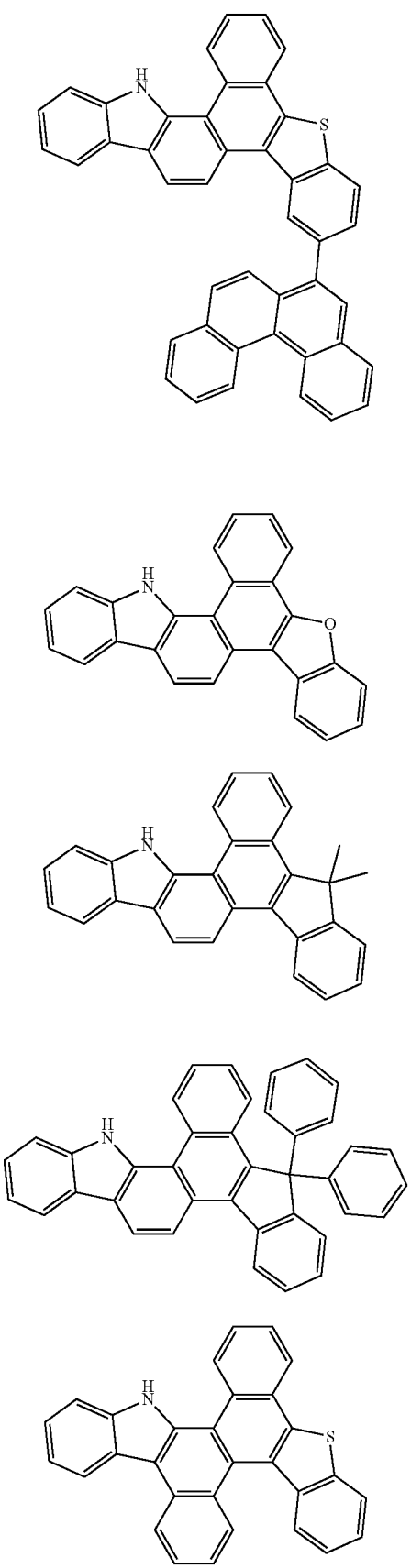
-continued
Sub 1A-16
Sub 1A-17
Sub 1A-18
Sub 1A-19
Sub 1B-1
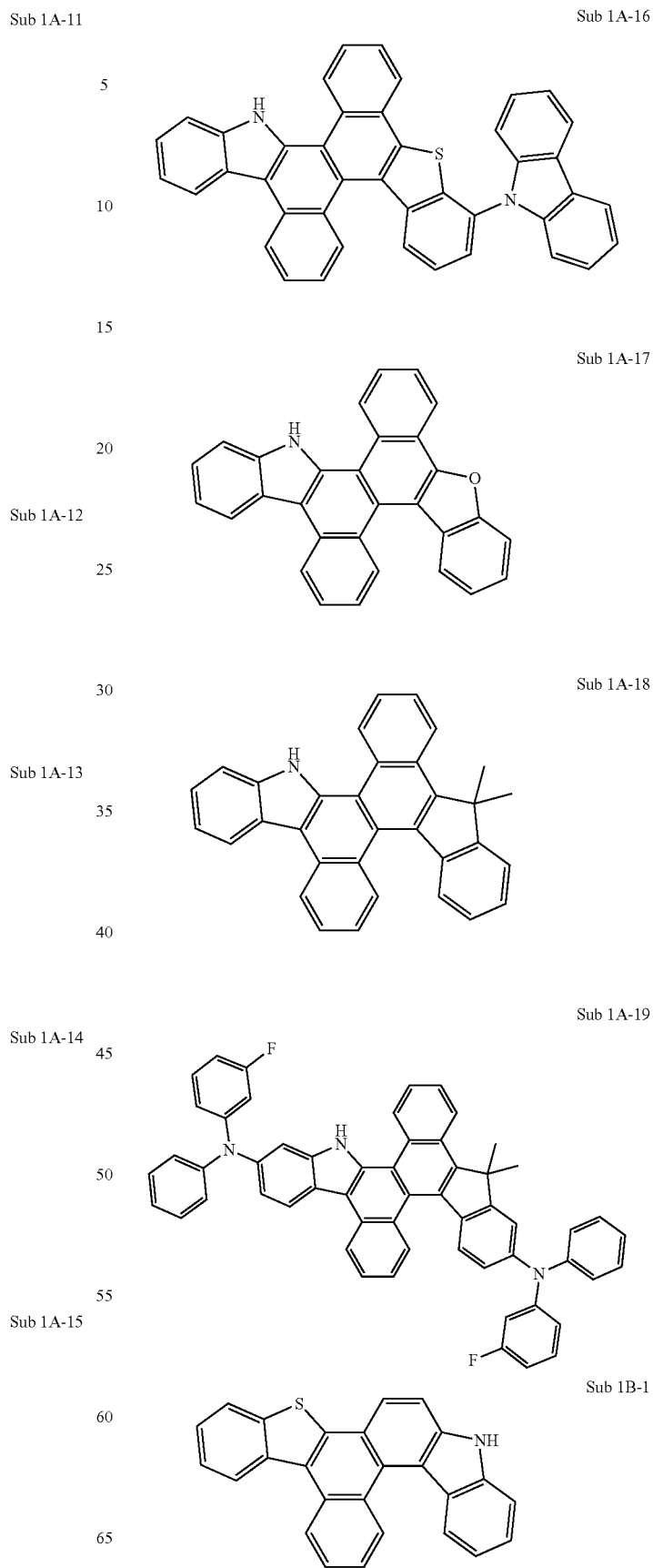

Sub 1B-2
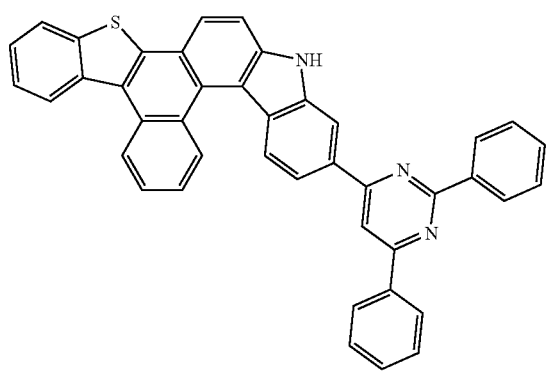
Sub 1B-3
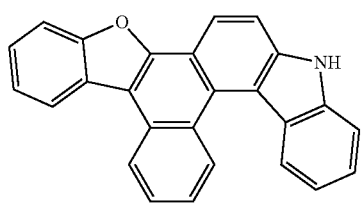
Sub 1B-4
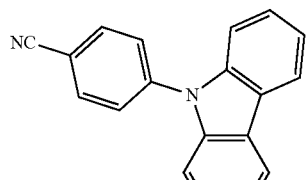
Sub 1B-5
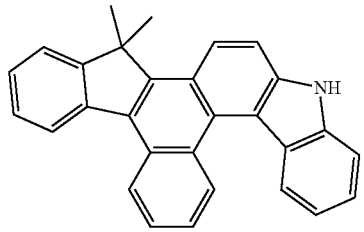
Sub 1B-6
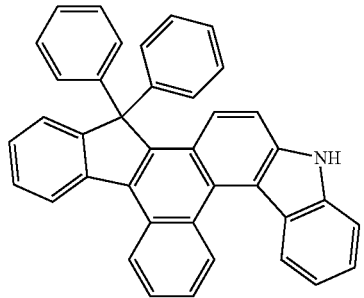
Sub 1B-7
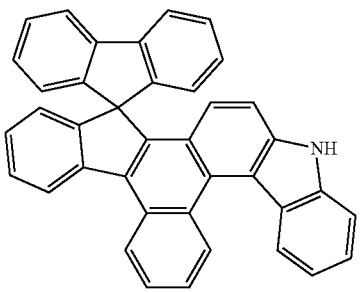
Sub 1B-8
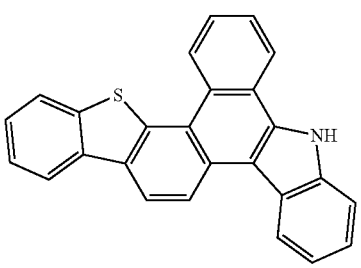
Sub 1B-9
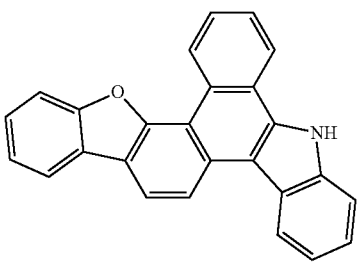
Sub 1B-10
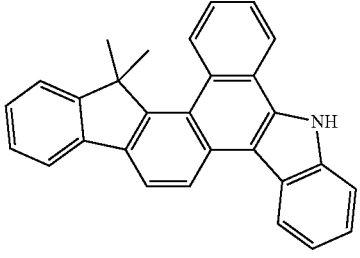
Sub 1B-11
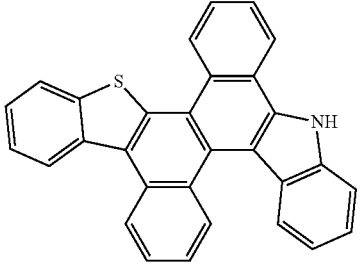
Sub 1B-12
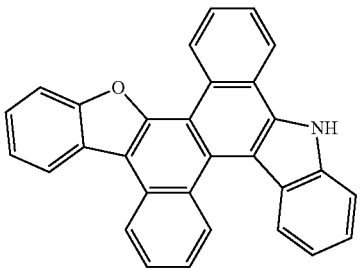

-continued

Sub 1B-13

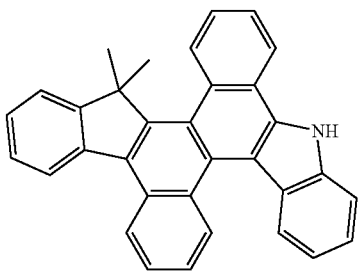

TABLE 1

| compound | FD-MS | compound | FD-MS |
| --- | --- | --- | --- |
| Sub 1A-1 | m/z = 373.09 ($C_{26}H_{15}NS$ = 373.47) | Sub 1A-8 | m/z = 373.09 ($C_{26}H_{15}NS$ = 373.47) |
| Sub 1A-12 | m/z = 357.12 ($C_{26}H_{15}NO$ = 357.40) | Sub 1A-19 | m/z = 803.31 ($C_{57}H_{39}F_2N_3$ = 803.94) |
| Sub 1B-5 | m/z = 383.17 ($C_{29}H_{21}N$ = 383.48) | Sub 1B-9 | m/z = 357.12 ($C_{26}H_{15}NO$ = 357.40) |
| Sub 1B-11 | m/z = 423.11 ($C_{30}H_{17}NS$ = 423.53) | | |

II. Synthesis of Sub 2

Sub 2 in the reaction schemes 1 and 2 can be synthesized by reaction route of the following reaction scheme 12, but there is no limitation thereto.

<Reaction Scheme 12>

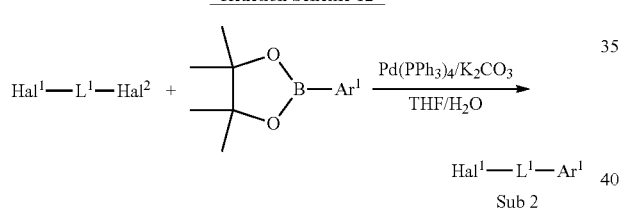

Sub 2

In the reaction scheme 12, $Hal^1$ and $Hal^2$ are Br or Cl.

The synthesis examples of the compounds comprised in Sub 2 are as follows.

1. Synthesis Example of Sub 2-13

<Reaction Scheme 13>

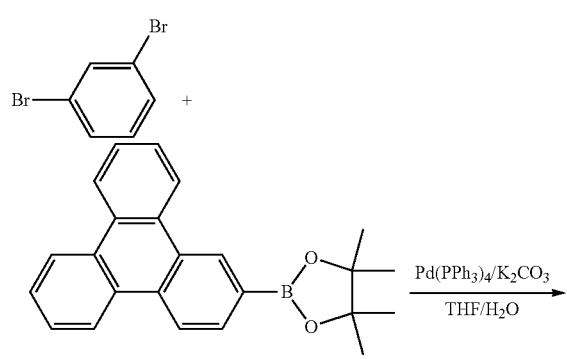

-continued

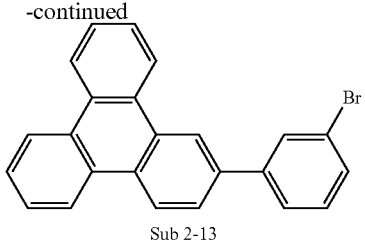

Sub 2-13

The starting material 1,3-dibromobenzene (20.17 g, 85.50 mmol) was dissolved in THF (300 ml) in a round bottom flask. Then, 4,4,5,5-tetramethyl-2-(triphenylen-2-yl)-1,3,2-dioxaborolane (33.32 g, 94.05 mmol), $Pd(PPh_3)_4$ (3.95 g, 3.42 mmol), $K_2CO_3$ (35.45 g, 256.51 mmol) and water (150 ml) were added to the solution. Then, the mixture was stirred at 90° C. When the reaction was completed, the reaction product was extracted with $CH_2Cl_2$ and water, and then the organic layer was dried with $MgSO_4$ and concentrated. Then, the concentrate was applied to silica gel column and recrystallized to obtain 20.65 g (yield: 63%) of the product.

2. Synthesis Example of Sub 2-17

<Reaction Scheme 14>

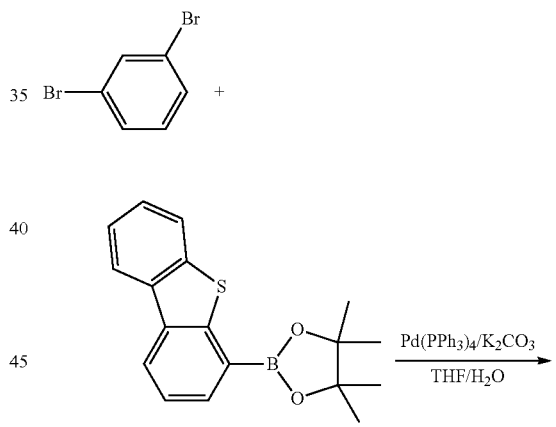

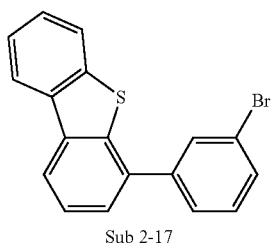

Sub 2-17

2-(dibenzo[b,d]thiophen-4-yl)-4,4,5,5-tetramethyl-1,3,2-dioxaborolane (27.37 g, 88.22 mmol), $Pd(PPh_3)_4$ (3.71 g, 3.21 mmol), $K_2CO_3$ (33.25 g, 240.61 mmol), THF (280 ml) and water (140 ml) were added to the starting material 1,3-dibromobenzene (18.92 g, 80.20 mmol), 19.32 g (yield: 71%) of the product was obtained by the same method as in synthesis of Sub 2-13.

3. Synthesis Example of Sub 2-19

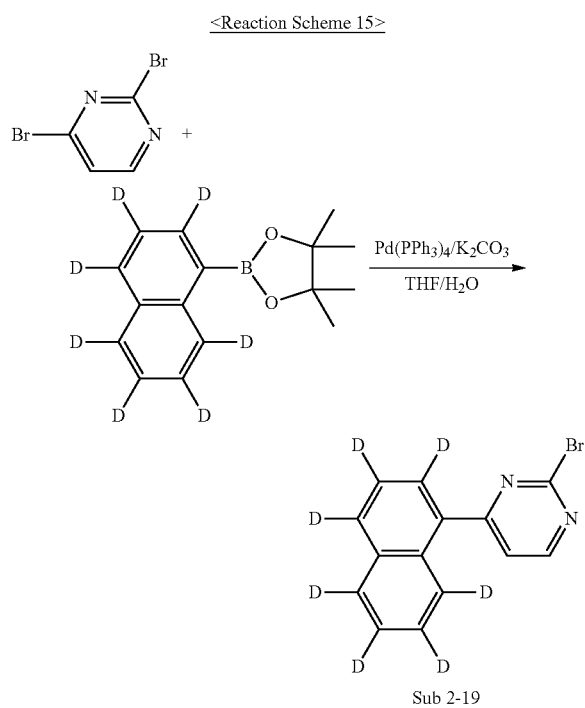

4,4,5,5-tetramethyl-2-(naphthalen-1-yl-d7)-1,3,2-dioxaborolane (29.54 g, 113.11 mmol), Pd(PPh$_3$)$_4$ (4.75 g, 4.11 mmol), K$_2$CO$_3$ (42.63 g, 308.47 mmol), THF (360 ml) and water (180 ml) were added to the starting material 2,4-dibromopyrimidine (24.46 g, 102.82 mmol), 18.03 g (yield: 60%) of the product was obtained by the same method as in synthesis of Sub 2-13.

4. Synthesis Example of Sub 2-36

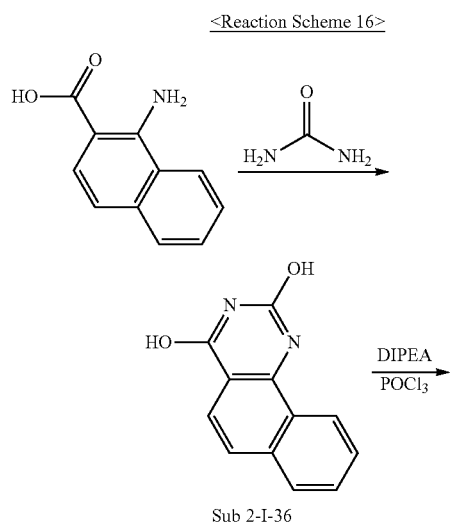

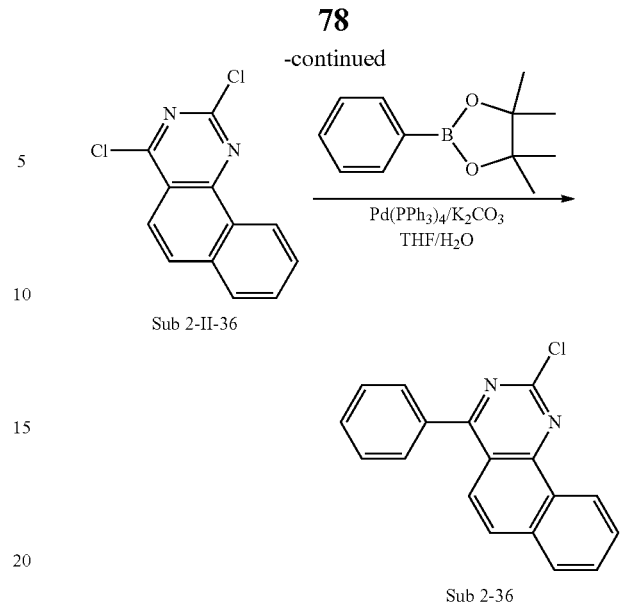

(1) Synthesis of Sub 2-I-36

The starting material 1-amino-2-naphthoic acid (75.11 g, 401.25 mmol) was placed in a round bottom flask together with urea (168.69 g, 2808.75 mmol), and then the mixture was stirred at 160° C. After checking the reaction through TLC, the mixture was cooled to 100° C. and water (200 ml) was added thereto, and then followed by stirring the mixture for 1 hour. When the reaction was completed, the obtained solid was filtered under reduced pressure, washed with water and dried to obtain 63.86 g (yield: 75%) of the product.

(2) Synthesis of Sub 2-II-36

Sub 2-I-36 (63.86 g, 300.94 mmol) obtained in the above synthesis was dissolved in POCl$_3$ (200 ml) in a round bottom flask at room temperature and N,N-Diisopropylethylamine (97.23 g, 752.36 mmol) was slowly added to the solution. Then, the mixture was stirred at 90° C. When the reaction was completed, the reaction product was concentrated and ice water (500 ml) was added thereto. Then, the resultant was stirred at room temperature for 1 hour. The obtained solid was filtered under reduced pressure and dried to obtain 67.47 g (yield: 90%) of the product.

(3) Synthesis of Sub 2-36

4,4,5,5-tetramethyl-2-phenyl-1,3,2-dioxaborolane (60.80 g, 297.94 mmol), Pd(PPh$_3$)$_4$ (12.52 g, 10.83 mmol), K$_2$CO$_3$ (112.30 g, 812.57 mmol), THF (950 ml) and water (475 ml) were added to Sub 2-II-36 (67.47 g, 270.86 mmol) obtained in the above synthesis, and then 44.89 g (yield: 57%) of the product was obtained by the same method as in synthesis of Sub 2-13.

5. Synthesis Example of Sub 2-54

<Reaction Scheme 17>

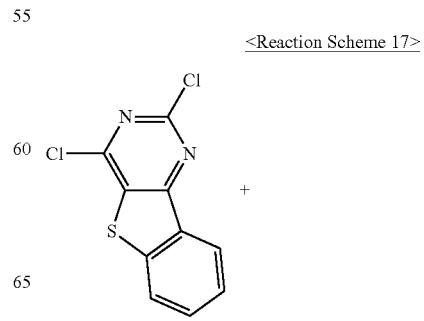

+

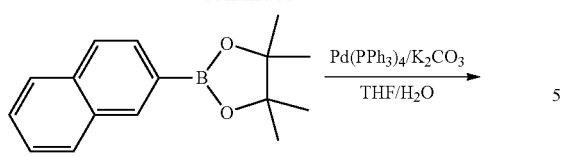

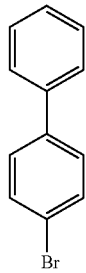

Sub 2-54

4,4,5,5-tetramethyl-2-(naphthalen-2-yl)-1,3,2-dioxaborolane (35.07 g, 138.02 mmol), Pd(PPh$_3$)$_4$ (5.80 g, 5.02 mmol), K$_2$CO$_3$ (52.02 g, 376.41 mmol), THF (440 ml) and water (220 ml) were added to the starting material 2,4-dichlorobenzo[4,5]thieno[3,2-d]pyrimidine (32.01 g, 125.47 mmol), and then 19.58 g (yield: 45%) of the product was obtained by the same method as in synthesis of Sub 2-13.

The compound belonging to Sub 2 may be the following compounds, but there is no limitation thereto. Table 2 shows FD-MS values of some compounds belonging to Sub 2.

Sub 2-1

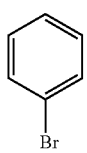

Sub 2-2

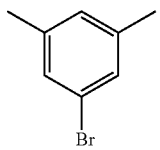

Sub 2-3

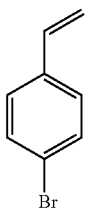

Sub 2-4

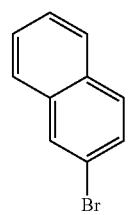

Sub 2-5

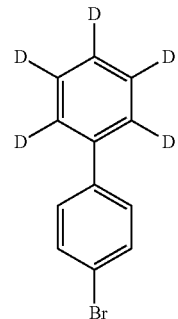

Sub 2-6

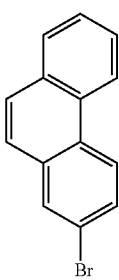

Sub 2-7

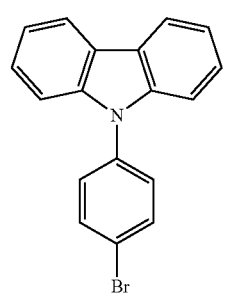

Sub 2-8

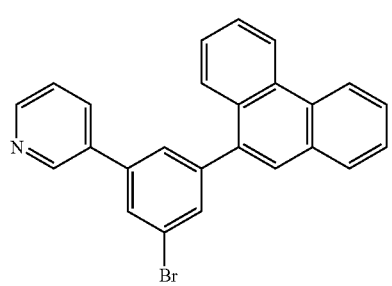

Sub 2-9

-continued
Sub 2-10
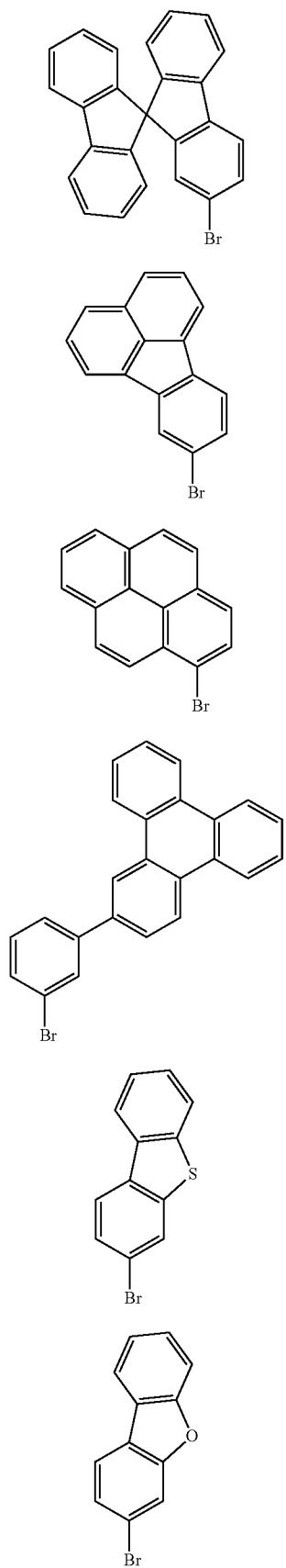
Sub 2-11
Sub 2-12
Sub 2-13
Sub 2-14
Sub 2-15
-continued
Sub 2-16
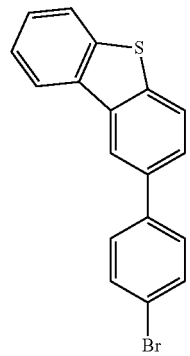
Sub 2-17
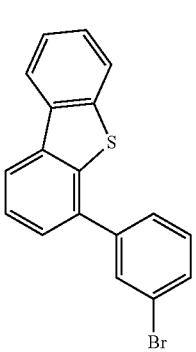
Sub 2-18
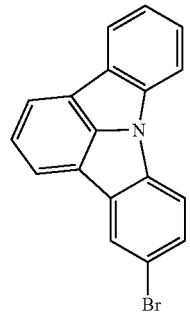
Sub 2-19
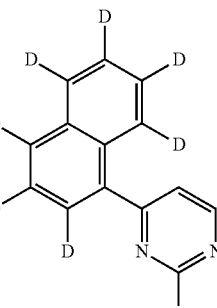
Sub 2-20
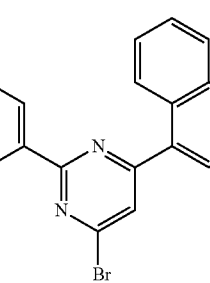

Sub 2-21
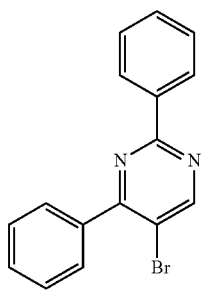
Sub 2-22
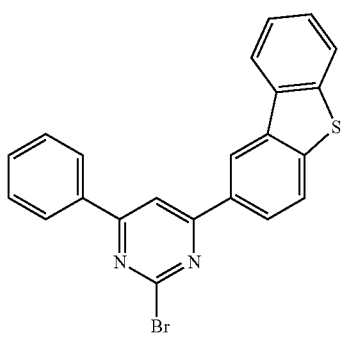
Sub 2-23
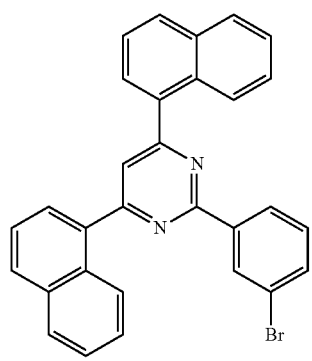
Sub 2-24
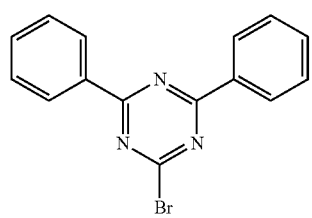
Sub 2-25
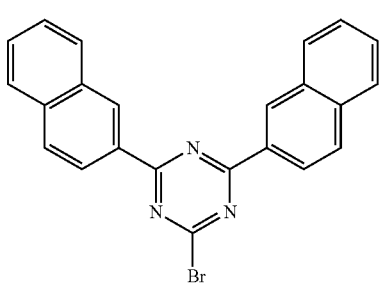
Sub 2-26
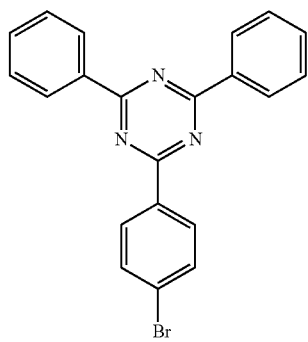
Sub 2-27
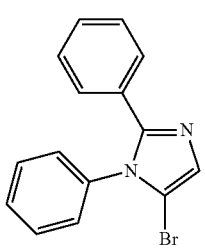
Sub 2-28
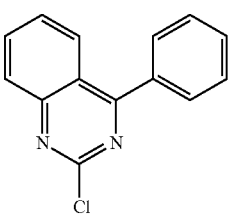
Sub 2-29
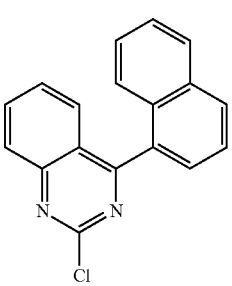
Sub 2-30
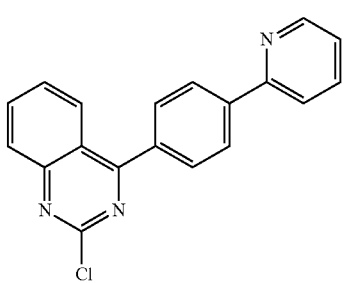

Sub 2-31
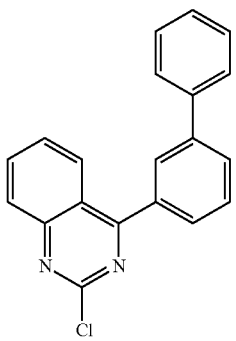
Sub 2-32
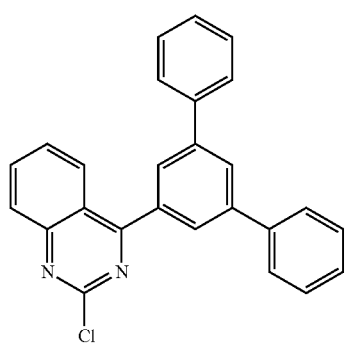
Sub 2-33
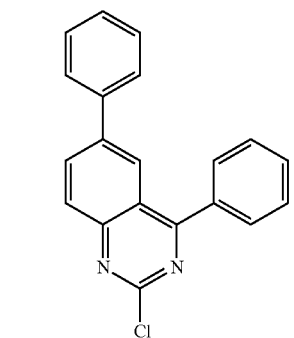
Sub 2-34
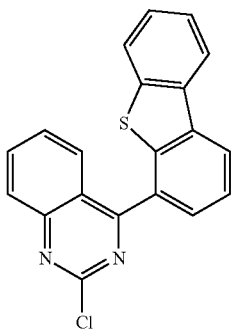
Sub 2-35
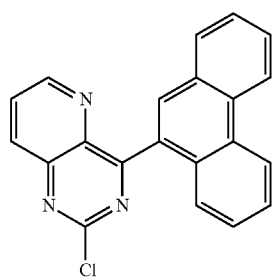
Sub 2-36
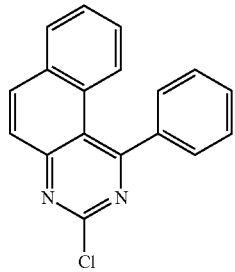
Sub 2-37
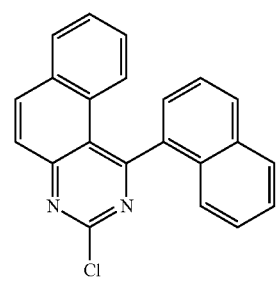
Sub 2-38
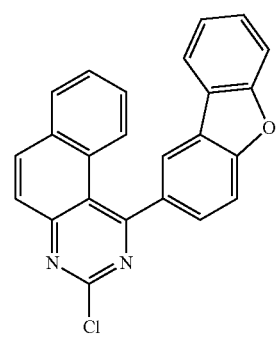
Sub 2-39
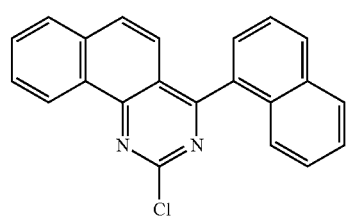
Sub 2-40
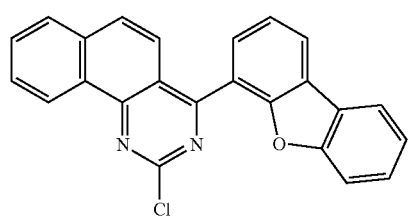

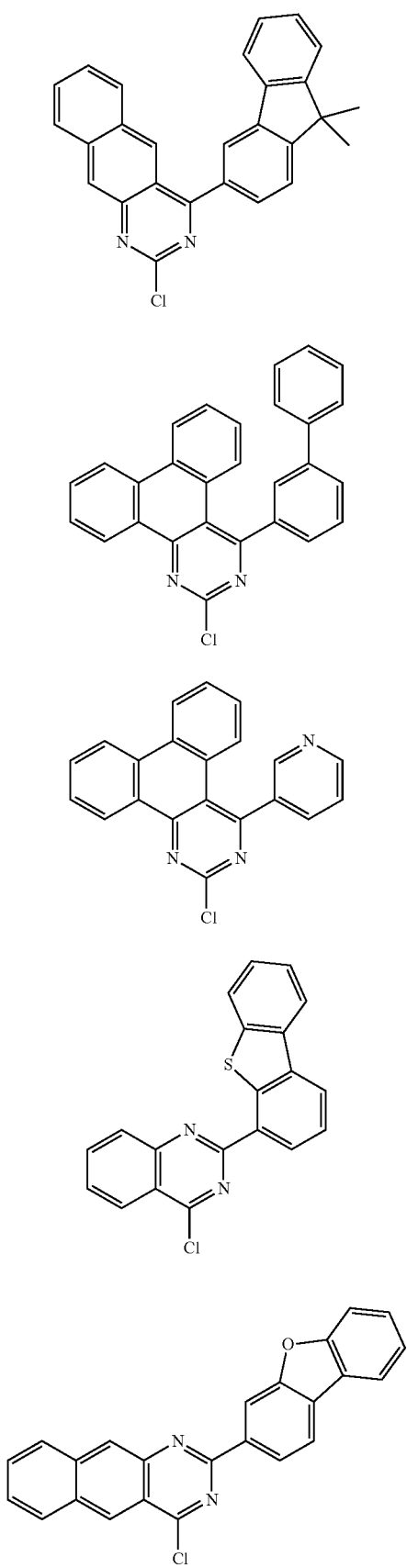
Sub 2-41
Sub 2-42
Sub 2-43
Sub 2-44
Sub 2-45
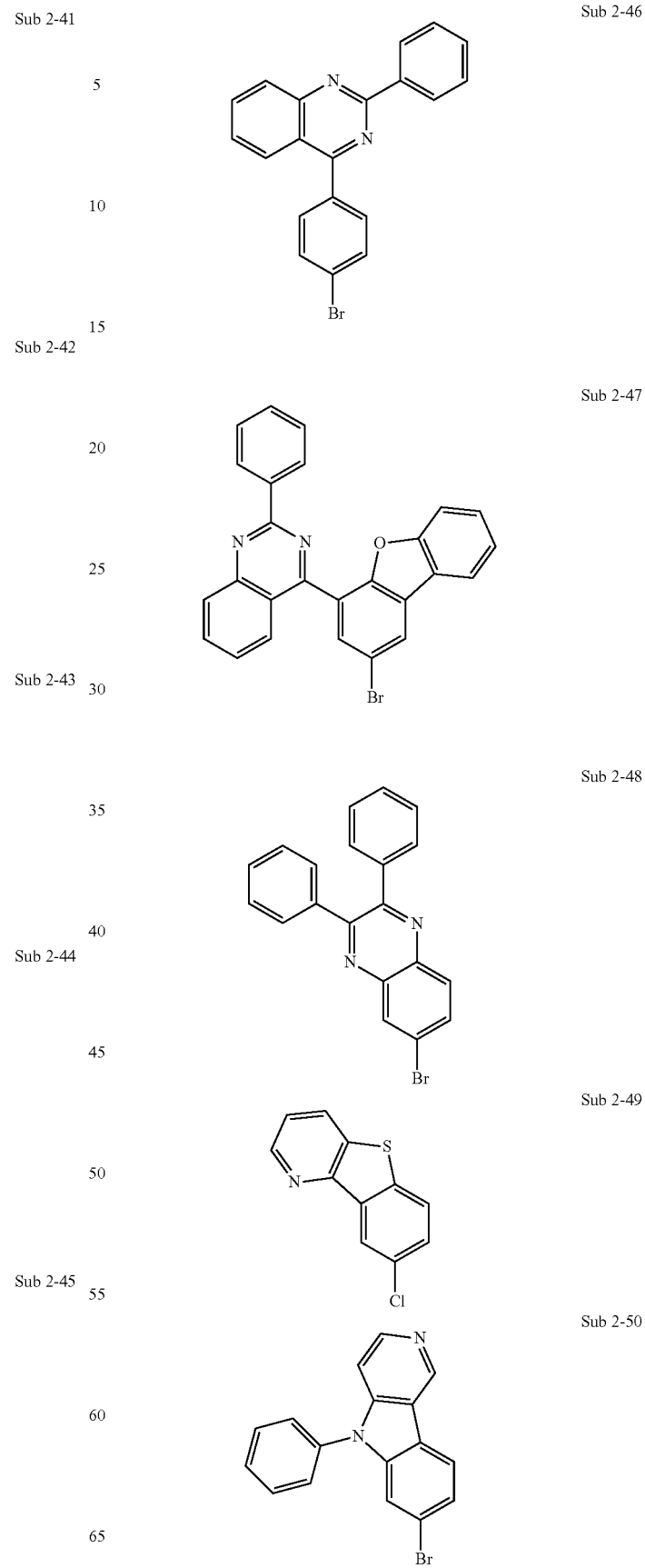
Sub 2-46
Sub 2-47
Sub 2-48
Sub 2-49
Sub 2-50

Sub 2-51
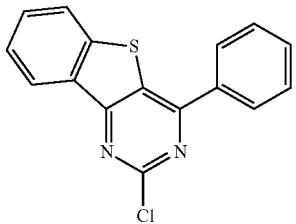
Sub 2-52
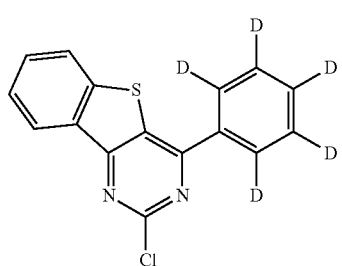
Sub 2-53
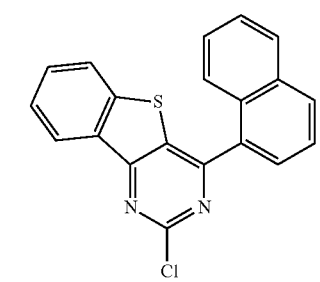
Sub 2-54
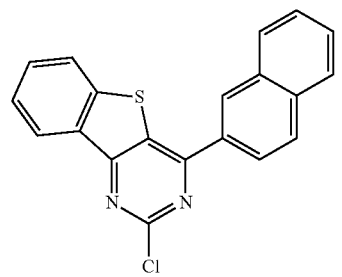
Sub 2-55
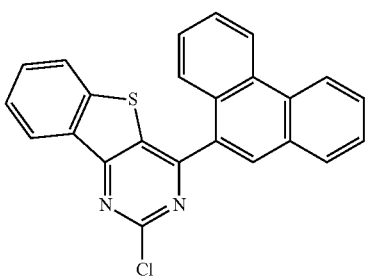
Sub 2-56
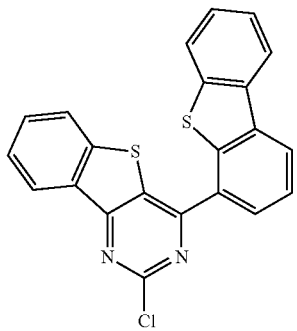
Sub 2-57
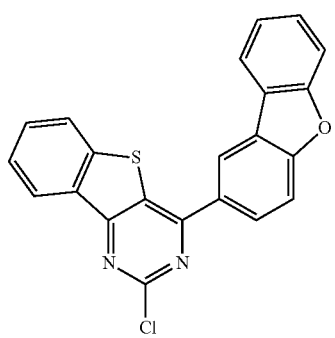
Sub 2-58
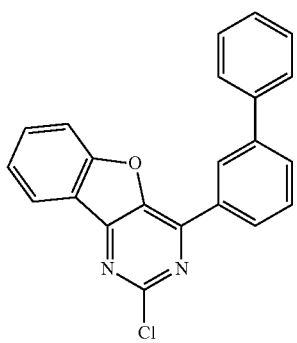
Sub 2-59
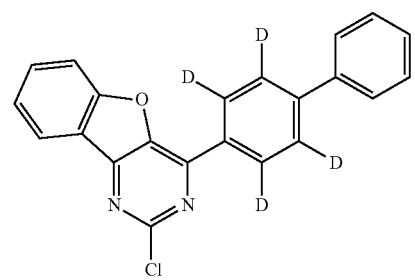
Sub 2-60
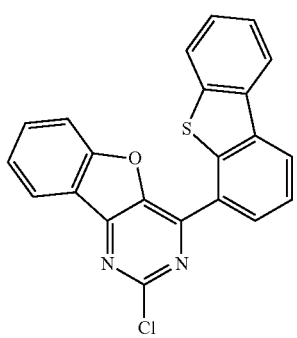

-continued
Sub 2-61
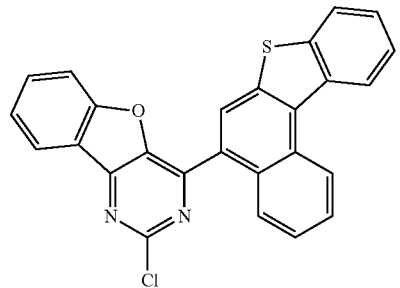
Sub 2-62
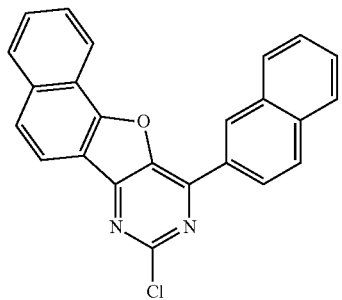
Sub 2-63
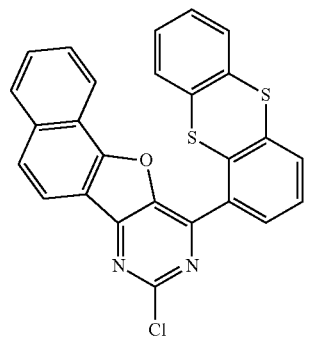
Sub 2-64
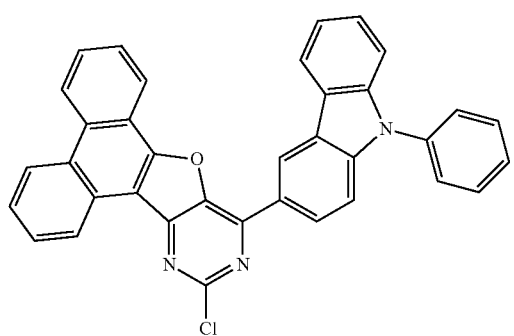
Sub 2-65
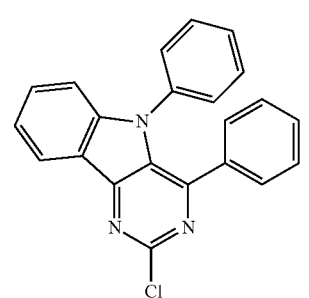
-continued
Sub 2-66
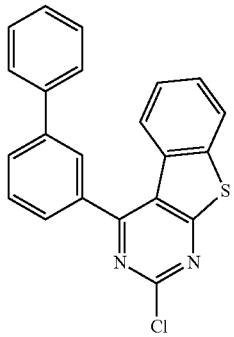
Sub 2-67
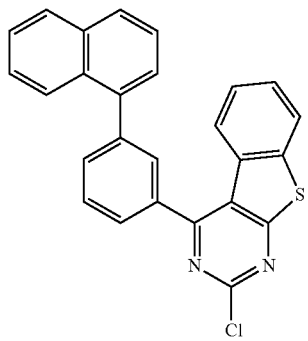
Sub 2-68
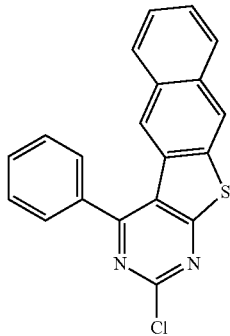
Sub 2-69
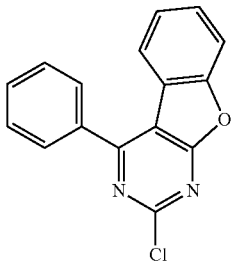
Sub 2-70
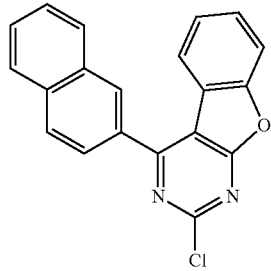

Sub 2-71
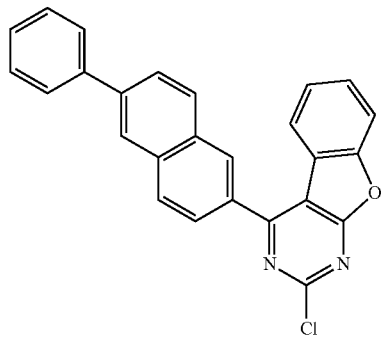
Sub 2-72
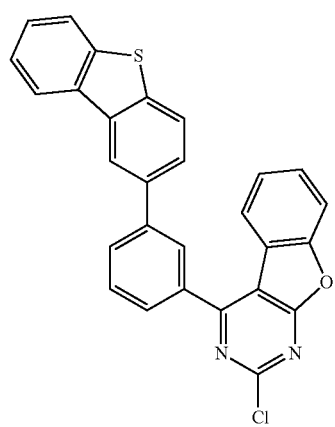
Sub 2-73
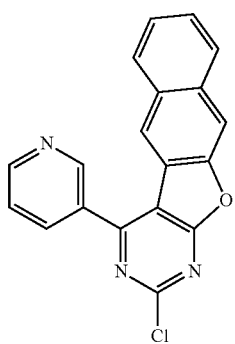
Sub 2-74
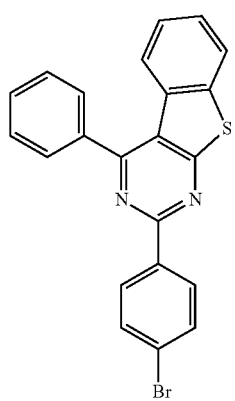
Sub 2-75
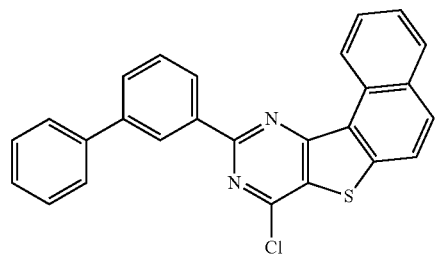
Sub 2-76
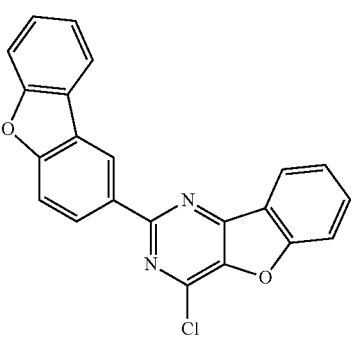
Sub 2-77
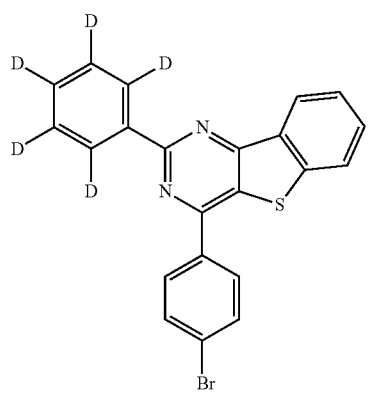
Sub 2-78
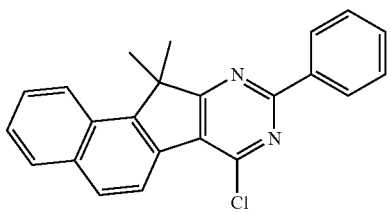
Sub 2-79
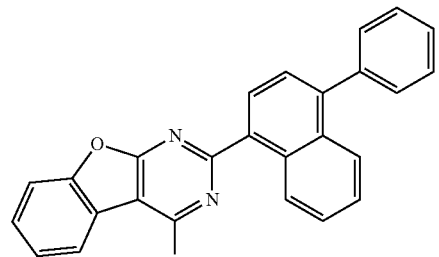

TABLE 2

| compound | FD-MS | compound | FD-MS |
|---|---|---|---|
| Sub 2-13 | m/z = 382.04 ($C_{24}H_{15}Br$ = 383.28) | Sub 2-17 | m/z = 337.98 ($C_{18}H_{11}BrS$ = 339.25) |
| Sub 2-19 | m/z = 291.04 ($C_{14}H_2D_7BrN_2$ = 292.18) | Sub 2-36 | m/z = 290.06 ($C_{18}H_{11}ClN_2$ = 290.75) |
| Sub 2-54 | m/z = 346.03 ($C_{20}H_{11}ClN_2S$ = 346.83) | | |

III. Synthesis of Final Product

Sub 1 (1 eq.) was dissolved in toluene in a round bottom flask. Then, Sub 2 (1 ep.), Pd$_2$(dba)$_3$ (0.03 ep.), P(t-Bu)$_3$ (0.06 ep.) and NaOt-Bu (3 ep.) were added the solution, and followed by stirring the mixture at 100° C. When the reaction was completed, the reaction product was extracted with CH$_2$Cl$_2$ and water. Then, the organic layer was dried with MgSO$_4$ and concentrated. Then, the concentrate was applied to silica gel column and recrystallized to obtain of a final product.

1. Synthesis Example of P 1-1

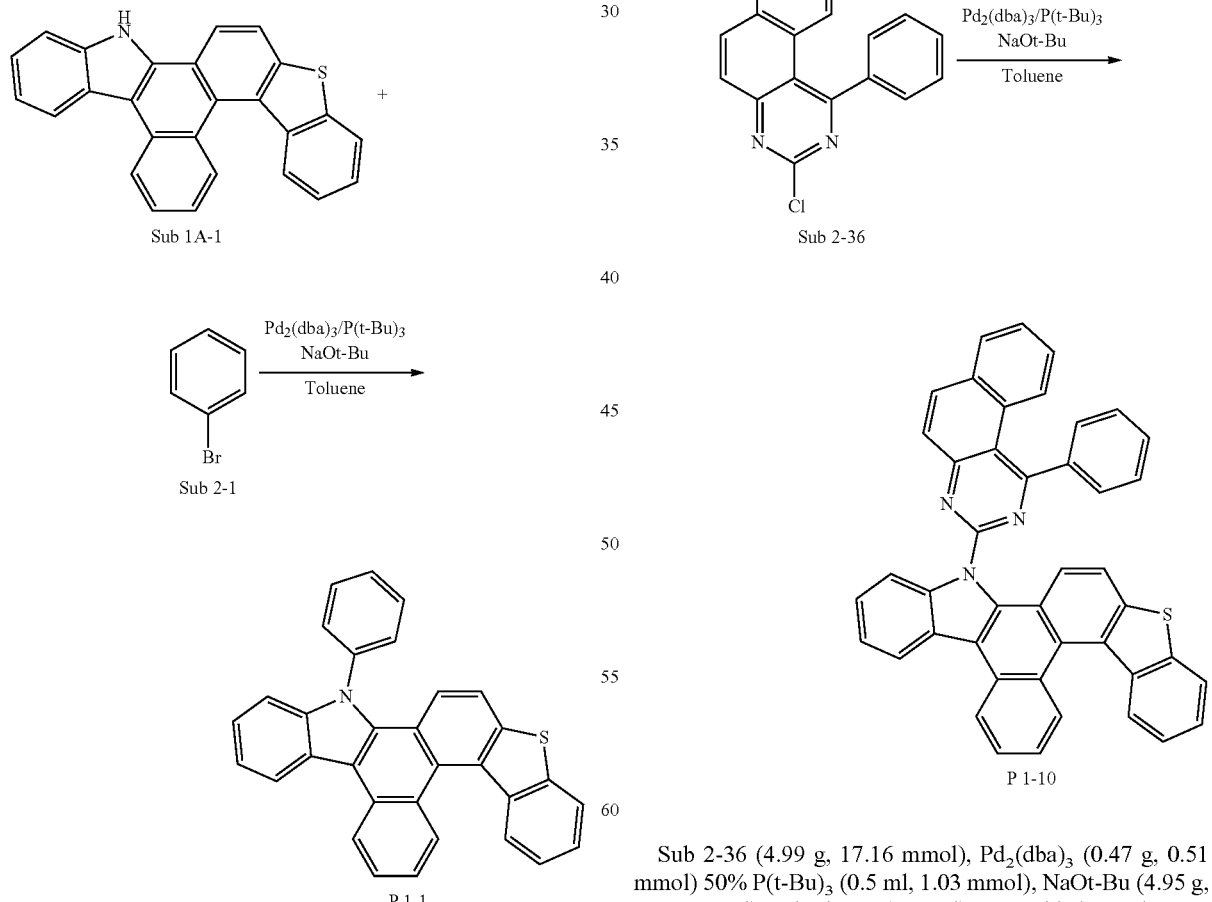

Sub 1A-1 (8.53 g, 22.84 mmol) obtained in the above synthesis was dissolved in toluene (230 ml) in a round bottom flask and Sub 2-1 (3.59 g, 22.84 mmol), Pd$_2$(dba)$_3$ (0.63 g, 0.69 mmol), 50% P(t-Bu)$_3$ (0.7 ml, 1.37 mmol) and NaOt-Bu (6.59 g, 68.52 mmol) were added to the solution. Then, the mixture was stirred at 100° C. When the reaction was completed, the reaction product was extracted with CH$_2$Cl$_2$ and water. Then, the organic layer was dried with MgSO$_4$ and concentrated. Then, the concentrate was applied to silica gel column and recrystallized to obtain 7.91 g (yield: 77%) of the product.

2. Synthesis Example of P 1-10

Sub 2-36 (4.99 g, 17.16 mmol), Pd$_2$(dba)$_3$ (0.47 g, 0.51 mmol) 50% P(t-Bu)$_3$ (0.5 ml, 1.03 mmol), NaOt-Bu (4.95 g, 51.49 mmol) and toluene (170 ml) were added to Sub 1A-1 (6.41 g, 17.16 mmol) obtained in the above synthesis, and then 7.33 g (yield: 68%) of the product was obtained by the same method as in synthesis of P 1-1.

3. Synthesis Example of P 1-36

<Reaction Scheme 20>

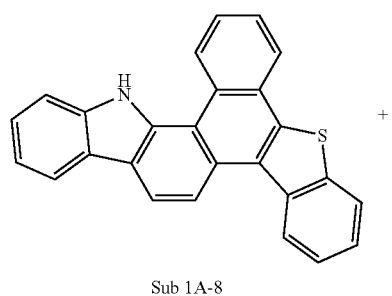

Sub 1A-8

+

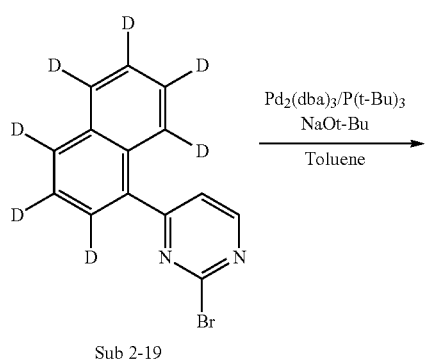

Sub 2-19

→ Pd$_2$(dba)$_3$/P(t-Bu)$_3$, NaOt-Bu, Toluene →

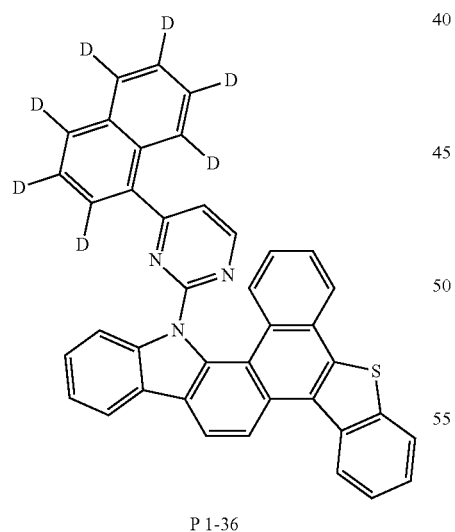

P 1-36

Sub 2-19 (5.57 g, 19.06 mmol), Pd$_2$(dba)$_3$ (0.52 g, 0.57 mmol) 50% P(t-Bu)$_3$ (0.6 ml, 1.14 mmol), NaOt-Bu (5.50 g, 57.19 mmol) and toluene (190 ml) were added to Sub 1A-8 (7.12 g, 19.06 mmol) obtained in the above synthesis, and then 7.69 g (yield: 69%) of the product was obtained by the same method as in synthesis of P 1-1.

4. Synthesis Example of P 1-58

<Reaction Scheme 21>

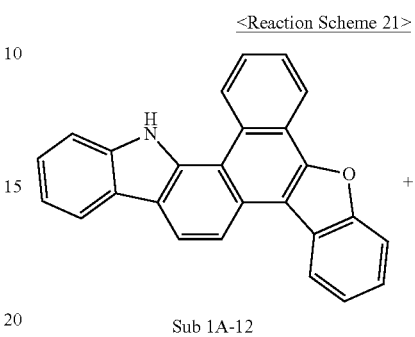

Sub 1A-12

+

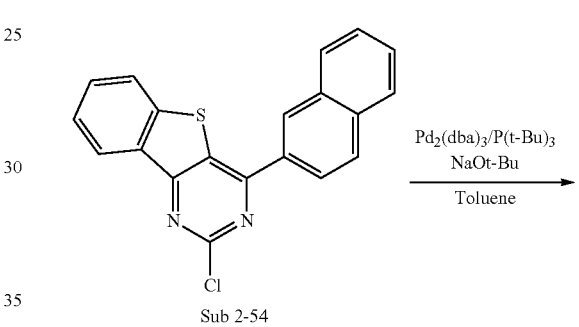

Sub 2-54

→ Pd$_2$(dba)$_3$/P(t-Bu)$_3$, NaOt-Bu, Toluene →

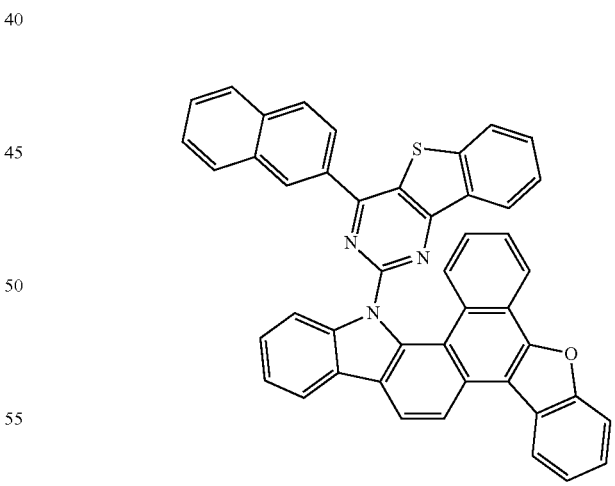

P 1-58

Sub 2-54 (6.28 g, 18.10 mmol), Pd$_2$(dba)$_3$ (0.50 g, 0.54 mmol) 50% P(t-Bu)$_3$ (0.5 ml, 1.09 mmol), NaOt-Bu (5.22 g, 54.31 mmol) and toluene (180 ml) were added to Sub 1A-12 (6.47 g, 18.10 mmol) obtained in the above synthesis, and then 7.25 g (yield: 60%) of the product was obtained by the same method as in synthesis of P 1-1.

5. Synthesis Example of P 1-61

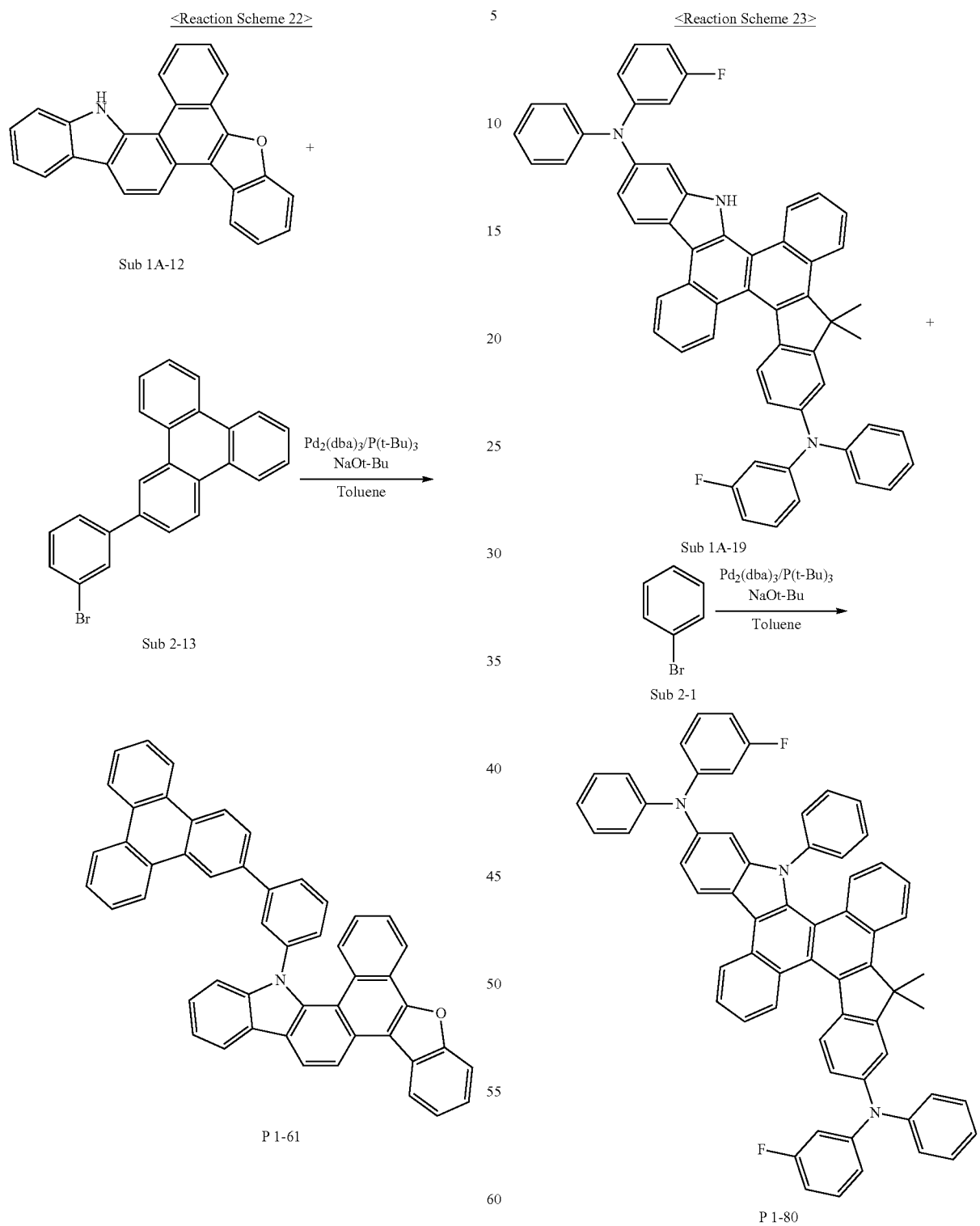

Sub 2-13 (7.44 g, 19.42 mmol), Pd$_2$(dba)$_3$ (0.53 g, 0.58 mmol) 50% P(t-Bu)$_3$ (0.6 ml, 1.17 mmol), NaOt-Bu (5.60 g, 58.25 mmol) and toluene (195 ml) were added to Sub 1A-12 (6.94 g, 19.42 mmol) obtained in the above synthesis, and then 8.07 g (yield: 63%) of the product was obtained by the same method as in synthesis of P 1-1.

6. Synthesis Example of P 1-80

Sub 2-1 (2.20 g, 13.99 mmol), Pd$_2$(dba)$_3$ (0.38 g, 0.42 mmol) 50% P(t-Bu)$_3$ (0.4 ml, 0.84 mmol), NaOt-Bu (4.03 g, 41.98 mmol) and toluene (140 ml) were added to Sub 1A-19 (11.25 g, 13.99 mmol) obtained in the above synthesis, and then 7.51 g (yield: 61%) of the product was obtained by the same method as in synthesis of P 1-1.

7. Synthesis Example of P 2-13

<Reaction Scheme 24>

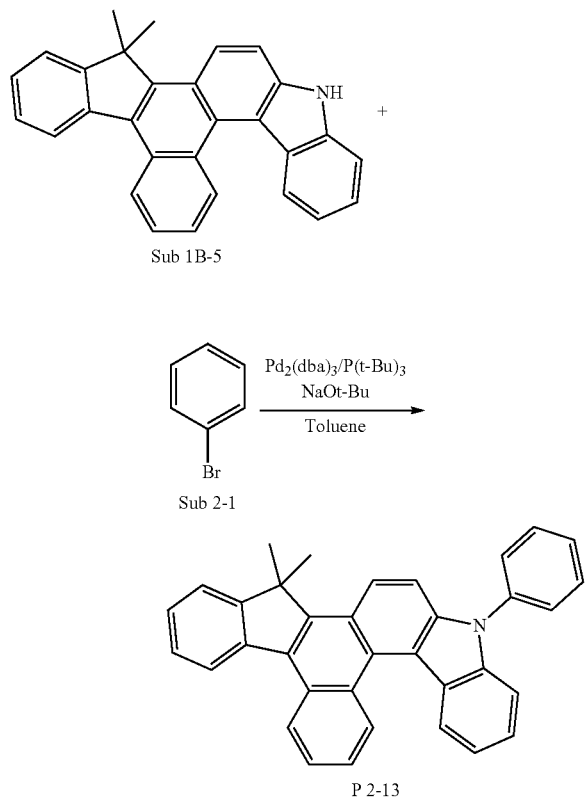

Sub 2-1 (3.44 g, 21.93 mmol), Pd$_2$(dba)$_3$ (0.60 g, 0.66 mmol) 50% P(t-Bu)$_3$ (0.6 ml, 1.32 mmol), NaOt-Bu (6.32 g, 65.79 mmol) and toluene (220 ml) were added to Sub 1B-5 (8.41 g, 21.93 mmol) obtained in the above synthesis, and then 7.66 g (yield: 76%) of the product was obtained by the same method as in synthesis of P 1-1.

8. Synthesis Example of P 2-27

<Reaction Scheme 25>

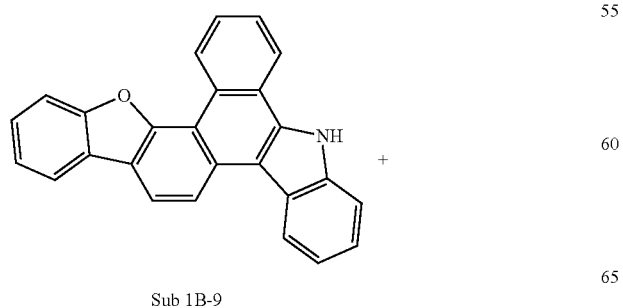

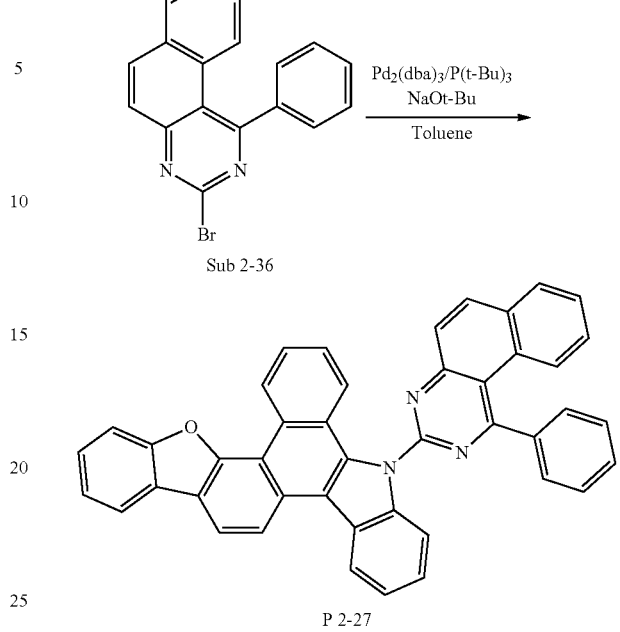

Sub 2-36 (5.95 g, 20.48 mmol), Pd$_2$(dba)$_3$ (0.56 g, 0.61 mmol) 50% P(t-Bu)$_3$ (0.6 ml, 1.23 mmol), NaOt-Bu (5.91 g, 61.44 mmol) and toluene (205 ml) were added to Sub 1B-9 (7.32 g, 20.48 mmol) obtained in the above synthesis, and then 8.14 g (yield: 65%) of the product was obtained by the same method as in synthesis of P 1-1.

9. Synthesis Example of P 2-34

<Reaction Scheme 26>

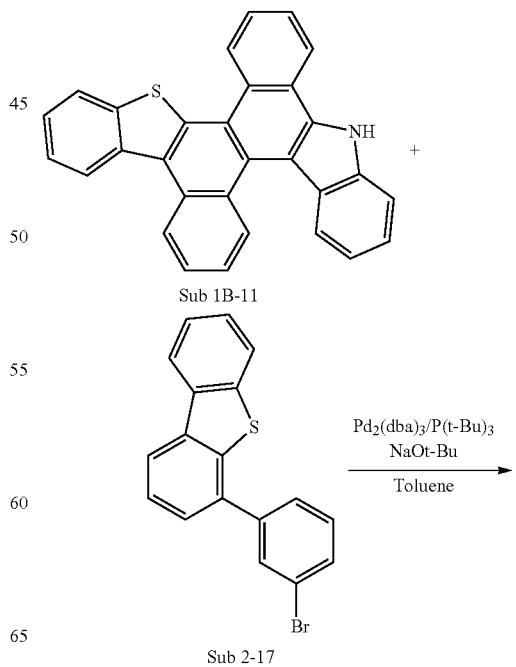

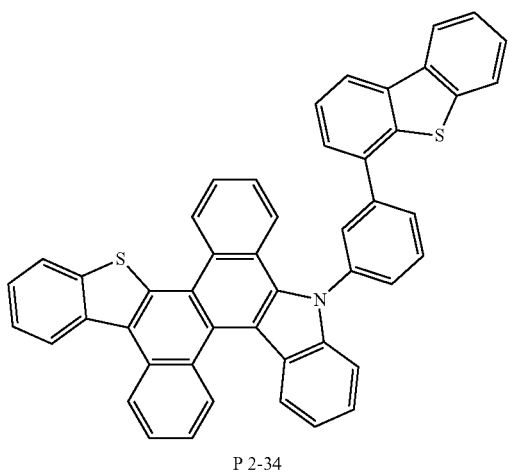

P 2-34

Sub 2-17 (5.09 g, 15.02 mmol), Pd$_2$(dba)$_3$ (0.41 g, 0.45 mmol) 50% P(t-Bu)$_3$ (0.4 ml, 0.90 mmol), NaOt-Bu (4.33 g, 45.05 mmol) and toluene (150 ml) were added to Sub 1B-11 (6.36 g, 15.02 mmol) obtained in the above synthesis, and then 7.37 g (yield: 72%) of the product was obtained by the same method as in synthesis of P 1-1.

Table 3 shows FD-MS values of some compounds of the present invention manufactured according to the above synthesis examples.

TABLE 3

| compound | FD-MS | compound | FD-MS |
|---|---|---|---|
| P 1-1 | m/z = 449.12 (C$_{32}$H$_{19}$NS = 449.56) | P 1-10 | m/z = 627.18 (C$_{44}$H$_{25}$N$_3$S = 627.75) |
| P 1-36 | m/z = 584.21 (C$_{40}$H$_{16}$D$_7$N$_3$S = 584.74) | P 1-58 | m/z = 667.17 (C$_{46}$H$_{25}$N$_3$OS = 667.78) |
| P 1-61 | m/z = 659.22 (C$_{50}$H$_{29}$NO = 659.77) | P 1-80 | m/z = 879.34 (C$_{63}$H$_{43}$F$_2$N$_3$ = 880.03) |
| P 2-13 | m/z = 459.20 (C$_{35}$H$_{25}$N = 459.58) | P 2-27 | m/z = 611.20 (C$_{44}$H$_{25}$N$_3$O = 611.69) |
| P 2-34 | m/z = 681.16 (C$_{48}$H$_{27}$NS$_2$ = 681.86) | | |

Even though an exemplary synthesis example of the present invention represented by the Formula 1 are described, all of them are based on Buchwald-Hartwig cross coupling reaction, Suzuki cross-coupling reaction, PPh$_3$-mediated reductive cyclization reaction (*J. Org. Chem.* 2005, 70, 5014.), Intramolecular acid-induced cyclization reaction (*J. mater. Chem.* 1999, 9, 2095.), Pd(II)-catalyzed oxidative cyclization reaction (*Org. Lett.* 2011, 13, 5504), Grignard reaction and Cyclic Dehydration reaction and the like. It will be understood by those skilled in the art that the above reaction proceeds even when other substituents (substituents of X, Y, L$^1$, Ar$^1$, R$^1$ to R$^4$, m, n, o and p and the like) defined in Formula 1 are bonded, in addition to the substituents described in the specific synthesis example.

For example, the reaction of Sub 1A and Sub 2→Final Product 1 in Reaction Scheme 1 and the reaction of Sub 1B and Sub 2→Final Product 2 in Reaction Scheme 2 are based on Buchwald-Hartwig cross coupling reaction, the reaction of the starting material→Sub 1-I in Reaction Scheme 3, the reaction of the starting material→Sub 1-I' in Reaction Scheme 4 and the reaction of the starting material→Sub 2 in Reaction Scheme 12 is based on Suzuki cross-coupling reaction, and the reaction of Sub 1-I→Sub 1 in Reaction Scheme 3 is based on PPh$_3$-mediated reductive cyclization reaction (*J. Org. Chem.* 2005, 70, 5014.). Further, the reaction of Sub 1-I'→Sub 1 in Reaction Scheme 4 is based on Intramolecular acid-induced cyclization reaction (*J. mater. Chem.* 1999, 9, 2095.), Pd(II)-catalyzed oxidative cyclization reaction (*Org. Lett.* 2011, 13, 5504), Grignard reaction and Cyclic Dehydration reaction and the like. The above reactions will proceed even if a substituent not specifically mentioned is attached.

Fabrication and Evaluation of Organic Electronic Element

[Example 1] Green OLED (A Phosphorescent Host)

Organic light emitting diodes (OLEDs) were fabricated according to a conventional method by using a compound of the present invention as luminous host material of the light emitting layer. First, an ITO layer (anode) was formed on a glass substrate, and then 4,4',4"-Tris[2-naphthyl(phenyl)amino]triphenylamine (hereinafter, "2-TNATA") was vacuum-deposited on the ITO layer to form a hole injection layer with a thickness of 60 nm. And 4,4'-bis[N-(1-naphthyl)-N-phenylamino]biphenyl (hereinafter, "NPD") was vacuum-deposited on the hole injection layer to form a hole transport layer with a thickness of 60 nm.

Subsequently, a light emitting layer with a thickness of 30 nm was vacuum-deposited on the hole transport layer by using compound P 1-1 of the present invention as a host material and tris(2-phenylpyridine)-iridium (hereinafter, "Ir (ppy)$_3$") as a dopant material in a weight ratio of 95:5.

Subsequently, (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq$_3$") was vacuum-deposited with a thickness of 40 nm on the hole blocking layer to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 20] Green OLED

The OLEDs were fabricated in the same manner as described in Example 1 except that compounds of the present invention described in Table 4 instead of the compound P 1-1 of the present invention were used as the green host material of a light emitting layer.

[Comparative Example 1] to [Comparative Example 6]

The OLEDs were fabricated in the same manner as described in Example 1 except that one of the comparative compounds 1 to 6 of the present invention instead of the compound P 1-1 of the present invention were used as the green host material of a light emitting layer.

<Comp.compd 1>

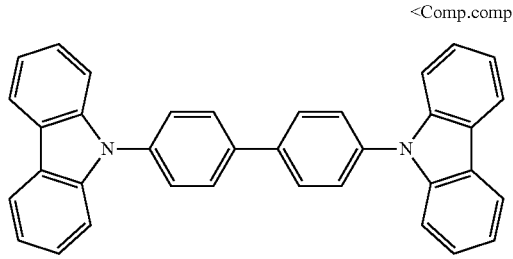

<Comp.compd 4>

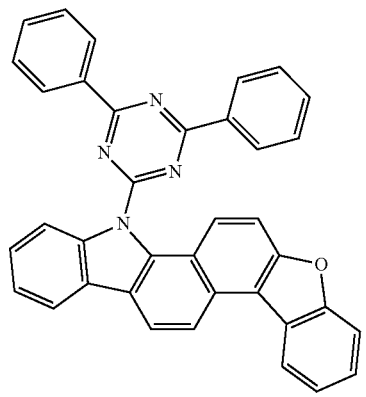

<Comp.compd 2>

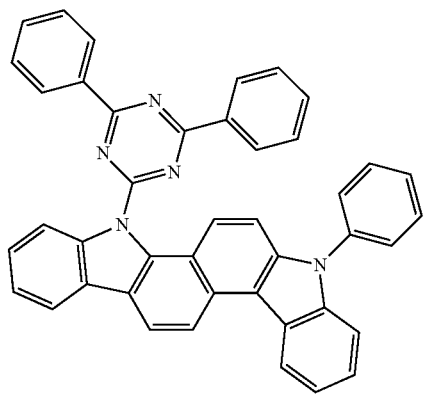

<Comp.compd 5>

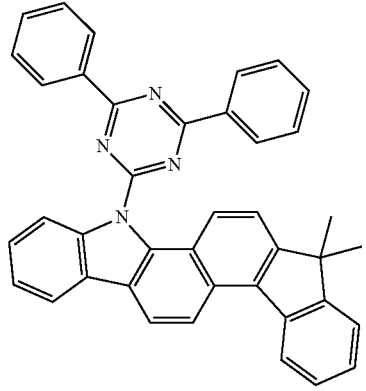

<Comp.compd 3>

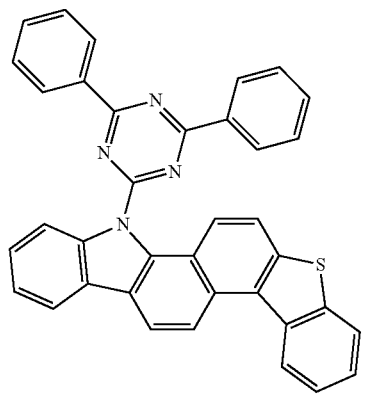

<Comp.compd 6>

Electroluminescence (EL) characteristics were measured with a PR-650 (Photoresearch) by applying a forward bias DC voltage to the OLEDs prepared in Examples 1 to 20 of the present invention and Comparative Examples 1 to 6. And, the T95 life time was measured using a life time measuring apparatus manufactured by Macscience Inc. at reference brightness of 5000 cd/m². The measurement results are shown in Table 4 below.

TABLE 4

| | compound | Voltage (V) | Current Density (mA/cm²) | Brightness (cd/m²) | Efficiency (cd/A) | Lifetime T (95) | CIE x | y |
|---|---|---|---|---|---|---|---|---|
| comp. Ex (1) | comp. Com1 | 5.9 | 21.7 | 5000 | 23.0 | 56.2 | 0.33 | 0.62 |
| comp. Ex (2) | comp. Com2 | 5.7 | 15.4 | 5000 | 32.5 | 79.5 | 0.33 | 0.62 |

TABLE 4-continued

|  | compound | Voltage (V) | Current Density (mA/cm²) | Brightness (cd/m²) | Efficiency (cd/A) | Lifetime T (95) | CIE x | CIE y |
|---|---|---|---|---|---|---|---|---|
| comp. Ex (3) | comp. Com3 | 5.5 | 12.7 | 5000 | 39.5 | 96.9 | 0.33 | 0.62 |
| comp. Ex (4) | comp. Com4 | 5.6 | 13.6 | 5000 | 36.7 | 91.5 | 0.33 | 0.62 |
| comp. Ex (5) | comp. Com5 | 5.6 | 14.6 | 5000 | 34.2 | 84.2 | 0.33 | 0.61 |
| comp. Ex (6) | comp. Com6 | 5.8 | 17.7 | 5000 | 28.3 | 71.2 | 0.33 | 0.62 |
| Ex. (1) | Com. (P 1-1) | 5.3 | 10.9 | 5000 | 45.7 | 121.7 | 0.33 | 0.62 |
| Ex. (2) | Com. (P 1-2) | 5.2 | 10.9 | 5000 | 46.0 | 124.7 | 0.33 | 0.62 |
| Ex. (3) | Com. (P 1-3) | 5.2 | 10.9 | 5000 | 46.0 | 124.7 | 0.33 | 0.62 |
| Ex. (4) | Com. (P 1-4) | 5.2 | 10.8 | 5000 | 46.3 | 121.8 | 0.33 | 0.61 |
| Ex. (5) | Com. (P 1-5) | 5.2 | 10.7 | 5000 | 46.7 | 130.9 | 0.33 | 0.62 |
| Ex. (6) | Com. (P 1-6) | 5.1 | 10.4 | 5000 | 47.9 | 141.1 | 0.33 | 0.61 |
| Ex. (7) | Com. (P 1-7) | 5.2 | 10.6 | 5000 | 47.1 | 131.9 | 0.33 | 0.62 |
| Ex. (8) | Com. (P 1-8) | 5.3 | 10.6 | 5000 | 47.1 | 131.9 | 0.33 | 0.61 |
| Ex. (9) | Com. (P 1-19) | 5.2 | 11.0 | 5000 | 45.5 | 115.8 | 0.33 | 0.62 |
| Ex. (10) | Com. (P 1-22) | 5.3 | 10.8 | 5000 | 46.3 | 129.7 | 0.33 | 0.62 |
| Ex. (11) | Com. (P 1-29) | 5.3 | 11.3 | 5000 | 44.4 | 118.2 | 0.33 | 0.61 |
| Ex. (12) | Com. (P 1-33) | 5.1 | 10.1 | 5000 | 49.5 | 157.1 | 0.33 | 0.61 |
| Ex. (13) | Com. (P 1-34) | 5.1 | 10.0 | 5000 | 49.9 | 158.5 | 0.33 | 0.62 |
| Ex. (14) | Com. (P 1-35) | 5.1 | 9.8 | 5000 | 50.8 | 156.4 | 0.33 | 0.62 |
| Ex. (15) | Com. (P 1-36) | 5.0 | 9.9 | 5000 | 50.5 | 158.2 | 0.33 | 0.62 |
| Ex. (16) | Com. (P 1-37) | 5.0 | 9.6 | 5000 | 51.8 | 165.6 | 0.33 | 0.61 |
| Ex. (17) | Com. (P 1-51) | 5.2 | 10.5 | 5000 | 47.6 | 146.7 | 0.33 | 0.61 |
| Ex. (18) | Com. (P 1-52) | 5.1 | 10.5 | 5000 | 47.6 | 148.8 | 0.33 | 0.62 |
| Ex. (19) | Com. (P 1-53) | 5.2 | 10.3 | 5000 | 48.4 | 153.2 | 0.33 | 0.62 |
| Ex. (20) | Com. (P 1-62) | 5.2 | 10.6 | 5000 | 47.0 | 138.9 | 0.33 | 0.62 |

From the results of the above table 4, it is confirmed that luminous efficiency and lifetime of device are remarkably improved when the compounds according to an embodiment of the present invention rather than comparative compounds 1 and 6 invention are used as phosphorescent host material of a light emitting layer.

Comparing 6-ring heterocyclic compounds comprising two five-membered rings, it can be confirmed that luminous efficiency and lifetime of device are higher when Comparative compound 2 rather than Comparative compounds 3 to 5 is used as host, wherein Comparative compound 2 is N—N type in which N is comprised as a key atom in each of the two 5-membered rings and Comparative compounds 3 to 5 have different heteroatoms such as N—S, N—O, and N—CR'R".

Generally, when molecules are stacked, strong electric interaction is shown as neighboring π-electrons increase. This is closely related to charge carrier mobility.

In case of Comparative compound 2 being 6-ring compound of N—N type, when it is stacked, molecules of it are arranged in the order of edge-to-face since it has a hetero core of N—N type having the same heteroatom. As a result, this is believed to result in low charge carrier mobility and low oxidation stability.

Like comparative compounds 3 to 5, the compound of the present invention has heterocyclic core that comprises different heteroatoms in ring compound, and thus the packing structure of the inventive compound is an antiparallel cofacial π-stacking structure. This makes the arrangement order of the molecules be face-to-face, which is due to the asymmetrically arranged heteroatoms in the compound. It is considered that the steric effect of Ar¹ bonded to the hetero atom N results in remarkably high carrier mobility and thus device exhibits a high efficiency, and the lifetime is considerably increased due to the high oxidation stability.

In addition, even though core is the same, the energy band gap varies depending on which position a specific substituent bonded to hetero atom N is introduced into. This can be confirmed by comparing comparative compounds 2 and 6 that have triazine as a specific substituent introduced into heteroatom N.

Comparative compound 2 has a wider energy band gap than Comparative compound 6, and thus Comparative compound 2 can be more proper than Comparative compound 6 as a host of the green OLED. It is considered that Comparative compound 6 into which a specific substituent is introduced is more suitable for a host of the red OLED.

The compound of the present invention has significantly higher luminescent efficiency and lifetime than the Comparative compounds 2 to 5, wherein the specific substituent introduced into the hetero atom N of the compound of the present invention is the same as that of the Comparative compound 2. This is because the compound of the present invention has the most appropriate T1 value and energy band gap so that the charge transfer from the host to the dopant can be smooth as the ring is further condensed into the core (7 or 8 rings) as well as the effects described above (high charge carrier mobility, high oxidation stability, wide energy bandgap).

[Example 21] Red OLED (A Phosphorescent Host)

Organic light emitting diodes (OLEDs) were fabricated according to a conventional method by using a compound of the present invention as luminous host material of the light emitting layer. First, an ITO layer (anode) was formed on a glass substrate, and then 2-TNATA was vacuum-deposited on the ITO layer to form a hole injection layer with a thickness of 60 nm, and then NPD was vacuum-deposited on the hole injection layer to form a hole transport layer with a thickness of 60 nm. Subsequently, a light emitting layer with a thickness of 30 nm was vacuum-deposited on the hole transport layer by using compound P 1-9 of the present invention as a host material and bis-(1-phenylisoquinoline) iridium(III)acetylacetonate (hereinafter, "(piq)₂Ir(acac)") as a dopant material in a weight ratio of 95:5. Subsequently, BAlq was vacuum-deposited with a thickness of 10 nm on the light emitting layer to form a hole blocking layer, and Alq₃ was vacuum-deposited with a thickness of 40 nm on the hole blocking layer to form an electron transport layer. Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example 22] to [Example 50] Red OLED

The OLEDs were fabricated in the same manner as described in Example 21 except that compounds of the present invention described in Table 5 instead of the compound P 1-9 of the present invention were used as the red host material of a light emitting layer.

[Comparative Example 7] and [Comparative Example 8]

The OLEDs were fabricated in the same manner as described in Example 21 except that one of the comparative compounds 1 and 6 of the present invention instead of the compound P 1-9 of the present invention were used as the red host material of a light emitting layer.

Electroluminescence (EL) characteristics were measured with a PR-650 (Photoresearch) by applying a forward bias DC voltage to the OLEDs prepared in Examples 21 to 50 of the present invention and Comparative Example 7 and Comparative Example 8. And, the T95 life time was measured using a life time measuring apparatus manufactured by Macscience Inc. at reference brightness of 2500 cd/m². The measurement results are shown in Table 5 below.

From the results of the above table 5, it is confirmed that luminous efficiency and lifetime are remarkably improved when the compounds according to an embodiment of the present invention rather than comparative compounds 1 and 6 are used as phosphorescent host material of a light emitting layer.

Thus, it can be seen that the structure having a heterocyclic core (7-membered rings or 8-membered rings) of which heteroatoms in the ring compound are different from each other serves as a main factor for improving the performance of the device in the light emitting layer of the red OLED (used as host) as well as in the light emitting layer of the green OLED (used as host). The compound of the present invention used as a host material of the light emitting layer has a high oxidation stability and a high charge carrier mobility, and thus it has a more effective charge balance. In particular, when a specific substituent such as benzoquinazoline, benzothienopyrimidine or benzofuropyrimidine among compound of the present invention is introduced into the compound, the compound becomes a proper structure to accommodate both holes and electrons and has a proper T1 value to facilitate charge transfer from the host to the dopant. As a result, it can be confirmed that the device exhibits the best luminous efficiency and lifetime.

In addition, in the case of phosphorescent host, because the correlation of the hole transfer layer and the dopant is grasped, even if a similar core is used, it will be very difficult to deduce the excellent electrical characteristics of the inventive compound showing in the phosphorescent host.

Although the exemplary embodiments of the present invention have been described for illustrative purposes, those skilled in the art will appreciate that various modifi-

TABLE 5

| | compound | Voltage (V) | Current Density (mA/cm²) | Brightness (cd/m²) | Efficiency (cd/A) | Lifetime T (95) | CIE x | CIE y |
|---|---|---|---|---|---|---|---|---|
| comp. Ex (7) | comp. Com1 | 6.6 | 35.2 | 2500 | 7.1 | 63.3 | 0.65 | 0.31 |
| comp. Ex (8) | comp. Com2 | 6.3 | 32.9 | 2500 | 7.6 | 79.6 | 0.66 | 0.32 |
| Ex. (21) | Com. (P 1-9) | 5.1 | 14.2 | 2500 | 17.7 | 178.3 | 0.66 | 0.31 |
| Ex. (22) | Com. (P 1-10) | 5.1 | 13.7 | 2500 | 18.2 | 193.2 | 0.66 | 0.31 |
| Ex. (23) | Com. (P 1-11) | 5.1 | 14.3 | 2500 | 17.5 | 183.4 | 0.66 | 0.32 |
| Ex. (24) | Com. (P 1-13) | 5.2 | 14.0 | 2500 | 17.8 | 185.7 | 0.66 | 0.31 |
| Ex. (25) | Com. (P 1-14) | 5.2 | 14.0 | 2500 | 17.8 | 186.3 | 0.66 | 0.32 |
| Ex. (26) | Com. (P 1-20) | 5.2 | 15.0 | 2500 | 16.7 | 164.9 | 0.66 | 0.32 |
| Ex. (27) | Com. (P 1-25) | 5.2 | 14.1 | 2500 | 17.7 | 173.0 | 0.66 | 0.32 |
| Ex. (28) | Com. (P 1-27) | 5.2 | 14.6 | 2500 | 17.2 | 169.2 | 0.66 | 0.31 |
| Ex. (29) | Com. (P 1-30) | 5.3 | 14.8 | 2500 | 16.9 | 164.7 | 0.66 | 0.31 |
| Ex. (30) | Com. (P 1-39) | 5.4 | 16.8 | 2500 | 14.9 | 160.9 | 0.66 | 0.31 |
| Ex. (31) | Com. (P 1-46) | 5.5 | 17.2 | 2500 | 14.5 | 159.8 | 0.66 | 0.31 |
| Ex. (32) | Com. (P 1-56) | 5.4 | 17.7 | 2500 | 14.1 | 151.9 | 0.66 | 0.31 |
| Ex. (33) | Com. (P 1-63) | 5.5 | 17.9 | 2500 | 14.0 | 153.5 | 0.66 | 0.31 |
| Ex. (34) | Com. (P 1-69) | 5.3 | 14.8 | 2500 | 16.9 | 169.3 | 0.66 | 0.31 |
| Ex. (35) | Com. (P 1-70) | 5.2 | 15.2 | 2500 | 16.5 | 167.2 | 0.66 | 0.32 |
| Ex. (36) | Com. (P 1-76) | 5.2 | 15.5 | 2500 | 16.1 | 161.5 | 0.66 | 0.32 |
| Ex. (37) | Com. (P 1-79) | 5.2 | 15.8 | 2500 | 15.8 | 160.5 | 0.66 | 0.32 |
| Ex. (38) | Com. (P 2-4) | 5.4 | 16.0 | 2500 | 15.7 | 162.8 | 0.66 | 0.32 |
| Ex. (39) | Com. (P 2-5) | 5.4 | 16.3 | 2500 | 15.3 | 155.8 | 0.66 | 0.32 |
| Ex. (40) | Com. (P 2-10) | 5.3 | 16.5 | 2500 | 15.1 | 152.4 | 0.66 | 0.31 |
| Ex. (41) | Com. (P 2-14) | 5.3 | 17.0 | 2500 | 14.7 | 149.3 | 0.66 | 0.32 |
| Ex. (42) | Com. (P 2-16) | 5.3 | 17.3 | 2500 | 14.5 | 144.1 | 0.66 | 0.32 |
| Ex. (43) | Com. (P 2-21) | 5.2 | 14.9 | 2500 | 16.8 | 176.6 | 0.66 | 0.31 |
| Ex. (44) | Com. (P 2-22) | 5.2 | 15.0 | 2500 | 16.7 | 171.0 | 0.66 | 0.31 |
| Ex. (45) | Com. (P 2-23) | 5.3 | 15.2 | 2500 | 16.5 | 169.1 | 0.66 | 0.31 |
| Ex. (46) | Com. (P 2-27) | 5.2 | 15.5 | 2500 | 16.2 | 161.0 | 0.66 | 0.32 |
| Ex. (47) | Com. (P 2-30) | 5.2 | 15.8 | 2500 | 15.8 | 164.7 | 0.66 | 0.31 |
| Ex. (48) | Com. (P 2-36) | 5.3 | 16.0 | 2500 | 15.6 | 157.0 | 0.66 | 0.31 |
| Ex. (49) | Com. (P 2-42) | 5.4 | 16.6 | 2500 | 15.0 | 146.9 | 0.66 | 0.31 |
| Ex. (50) | Com. (P 2-44) | 5.3 | 17.0 | 2500 | 14.7 | 143.9 | 0.66 | 0.32 |

The invention claimed is:

1. A compound of Formula 1:

[Formula 1]

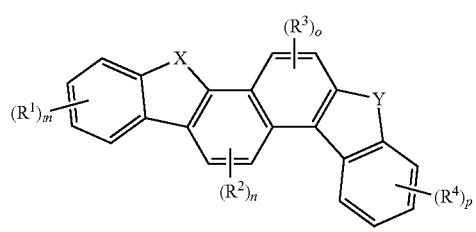

wherein:
R$^1$ to R$^4$ are each independently selected from the group consisting of deuterium, tritium, halogen, a cyano group, a nitro group, a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-O50 alkyl group, a C$_2$-C$_{20}$ alkenyl group, a C$_2$-C$_{20}$ alkynyl group, -L$^a$-N(R$^a$)(R$^b$), a C$_1$-C$_{30}$ alkoxyl group and a C$_6$-C$_{30}$ aryloxy group, wherein neighboring R$^1$ groups to neighboring R$^4$ groups are optionally linked to each other to form a ring with the proviso that either neighboring R$^2$ groups or neighboring R$^3$ groups are bonded to each other to form a benzene ring, m and p are each an integer of 0 to 4, n and o are each an integer of 0 to 2, and the plurality of R$^1$s to R$^4$s are each the same or different from each other when m and p are each an integer of 2 to 4 and n and o are each the integer of 2, one of X and Y is N(-L$^1$-Ar$^1$), and the other is S, O or C(Ar$^2$)(Ar$^3$), L$^1$ is selected from the group consisting of a single bond, a C$_6$-C$_{60}$ arylene group, a fluorenylene group, a C$_2$-C$_{60}$ heterocyclic group containing at least one heteroatom selected from the group consisting of O, N, S, Si, and P, and a fused ring formed by a C$_3$-C$_{60}$ aliphatic ring and a C$_6$-C$_{60}$ aromatic ring, Ar$^1$ is selected from the group consisting of a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, -L$^a$-N(R$^a$)(R$^b$), a C$_1$-C$_{30}$ alkoxyl group, and a C$_6$-C$_{30}$ aryloxyl group, Ar$^2$ and Ar$^3$ are each independently selected from the group consisting of a C$_6$-C$_{60}$ aryl group, a fluorenyl group, a C$_2$-C$_{60}$ heterocyclic group containing at least one heteroatom selected from the group consisting of O, N, S, Si, and P, a fused ring group of a C$_3$-C$_{60}$ aliphatic ring and a C$_6$-C$_{60}$ aromatic ring, a C$_1$-C$_{50}$ alkyl group, a C$_2$-C$_{20}$ alkenyl group, a C$_2$-C$_{20}$ alkynyl group, a C$_1$-C$_{30}$ alkoxyl group, and a C$_6$-C$_{30}$ aryloxy group, and Ar$^2$ and Ar$^3$ are optionally bonded to each other to form a spiro compound together with the C to which they are bonded, L$^a$ is each independently selected from the group consisting of a single bond, a C$_6$-C$_{60}$ arylene group, a fluorenylene group; a C$_2$-C$_{60}$ heterocyclic group containing at least one heteroatom selected from the group consisting of O, N, S, Si, and P, and a fused ring of a C$_3$-C$_{60}$ aliphatic ring and a C$_6$-C$_{60}$ aromatic ring, R$^a$ and R$^b$ are each independently selected from the group consisting of a C$_6$-C$_{60}$ aryl group, a fluorenyl group, a C$_2$-C$_{60}$ heterocyclic group containing at least one heteroatom selected from the group consisting of O, N, S, Si, and P, a C$_1$-C$_{50}$ alkyl group, a fused ring group of a C$_3$-C$_{60}$ aliphatic ring and a C$_6$-C$_{60}$ aromatic ring, and a C$_2$-C$_{20}$ alkenyl group, R$^1$ to R$^4$, R$^a$, R$^b$, L$^1$, L$^a$, Ar$^1$ to Ar$^3$ and a ring formed by neighboring groups of R$^1$s to R$^4$s are each optionally further substituted with one or more substituents selected from the group consisting of deuterium, halogen, a silane group substituted or unsubstituted with a C$_1$-C$_{20}$ alkyl group or a C$_6$-C$_{20}$ aryl group, a siloxane group, a boron group, a germanium group, a cyano group, a nitro group, a C$_1$-C$_{20}$ alkylthio group, a C$_1$-C$_{20}$ alkoxyl group, a C$_1$-C$_{20}$ alkyl group, a C$_2$-C$_{20}$ alkenyl group, a C$_2$-C$_{20}$ alkynyl group, -N(R$^c$)(R$^d$), a C$_6$-C$_{20}$ aryl group, a C$_6$-C$_{20}$ aryl group substituted with deuterium, a fluorenyl group, a C$_2$-C$_{20}$ heterocyclic group containing at least one heteroatom selected from the group consisting of O, N, S, Si, and P, a C$_3$-C$_{20}$ cycloalkyl group, a C$_7$-C$_{20}$ arylalkyl group and a C$_8$-C$_{20}$ arylalkenyl group, and R$^c$ and R$^d$ are each independently selected from the group consisting of a C$_6$-C$_{60}$ aryl group, a fluorenyl group, and a C$_2$-C$_{60}$ heterocyclic group containing at least one heteroatom selected from the group consisting of O, N, S, Si and P.

2. The compound of claim 1, represented by one of the following Formulas 2 to 4:

<Formula 2>

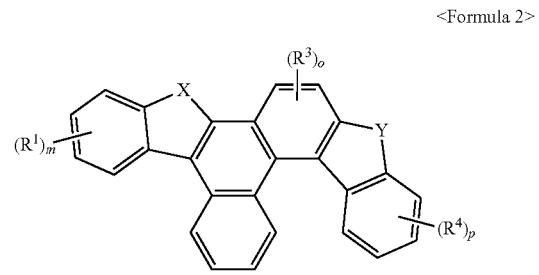

<Formula 3>

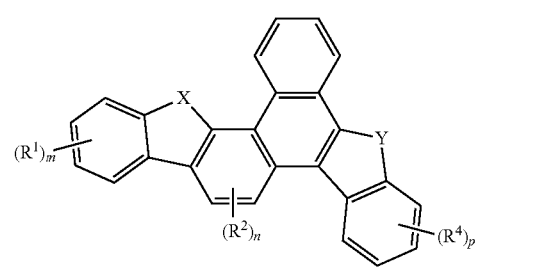

<Formula 4>
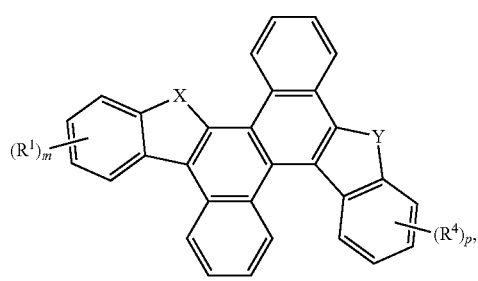
wherein X, Y, R$^1$ to R$^4$, m, n, o, and p are the same as defined in claim 1.
3. The compound of claim 1, represented by one of the following Formulas 5 to 10:
<Formula 5>
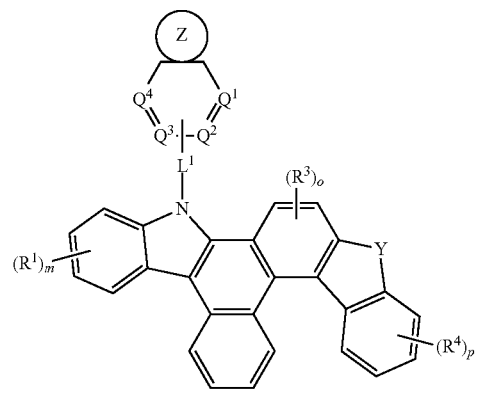
<Formula 6>
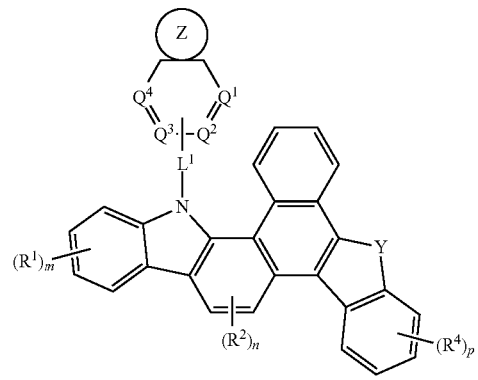
<Formula 7>
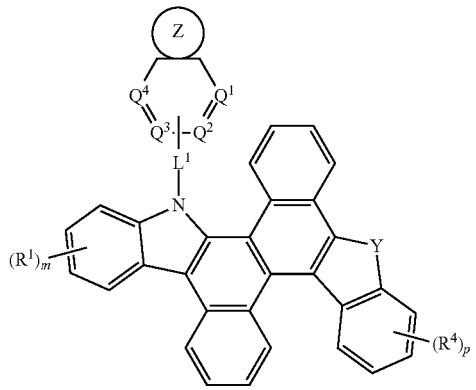
<Formula 8>
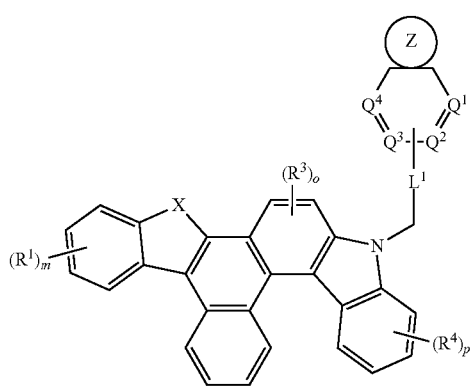
<Formula 9>
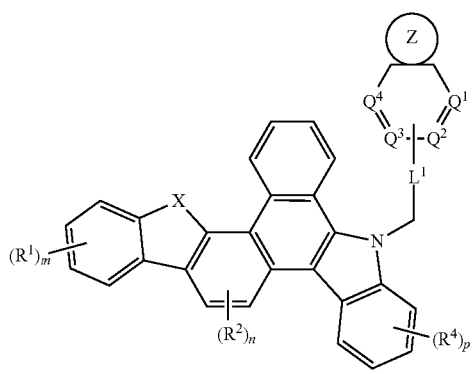
<Formula 10>
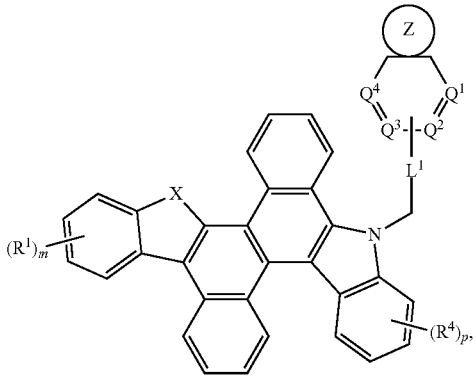

wherein X, Y, $R^1$ to $R^4$, m, n, o, and p are the same as defined in claim 1, Z ring is a $C_6$-$C_{60}$ aromatic ring or a $C_2$-$C_{60}$ heterocyclic group containing at least one heteroatom selected from the group consisting of O, N, S, Si, and P, one of $Q^1$ to $Q^4$ is carbon(C) bonded to $L^1$, and the others are N or C($R^e$), and $R^e$ is selected from the group consisting of hydrogen, deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

4. The compound of claim 3, wherein Z ring in Formulas 5 to 10 is one of the following groups:

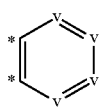
<Z-1>

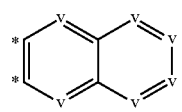
<Z-2>

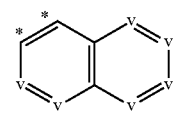
<Z-3>

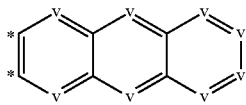
<Z-4>

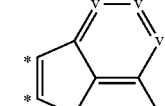
<Z-5>

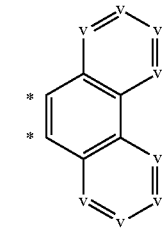
<Z-6>

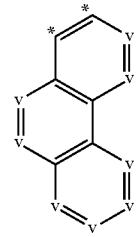
<Z-7>

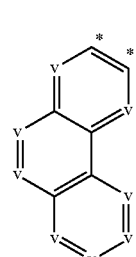
<Z-8>

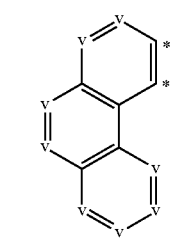
<Z-9>

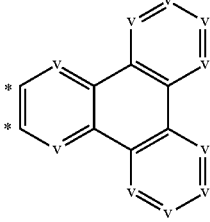
<Z-10>

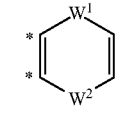
<Z-11>

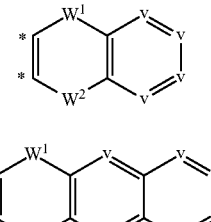
<Z-12>

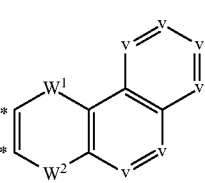
<Z-13>

<Z-14>

<Z-15>

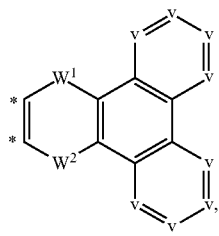

wherein

V is each independently N or C(R^e), wherein R^e is the same as defined in claim 3, W$^1$ and W$^2$ are each independently a single bond, N(-L$^1$-Ar$^1$), S, O or C(Ar$^2$)(Ar$^3$), wherein L$^1$, Ar$^1$, Ar$^2$ and Ar$^3$ are the same as defined in claim 1, and "*" indicates the position to which a ring including Q$^1$ to Q$^4$ is bonded.

5. The compound of claim 3, wherein at least one of Q$^1$ to Q$^4$ in Formulas 5 to 10 is N.

6. The compound of claim 1, represented one of the following compounds:

P 1-1

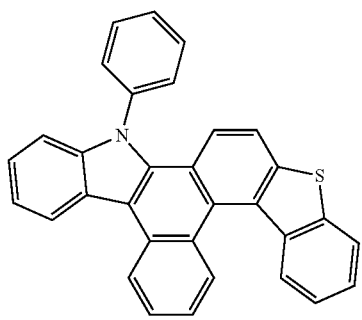

P 1-2

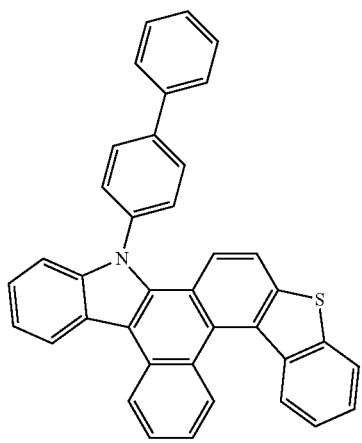

P 1-3

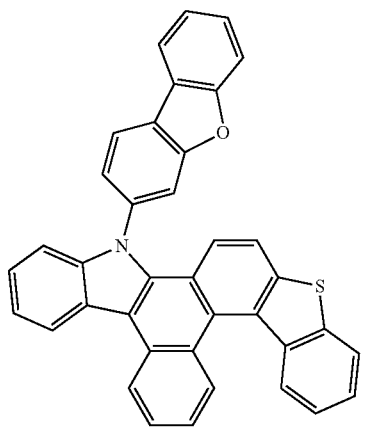

P 1-4

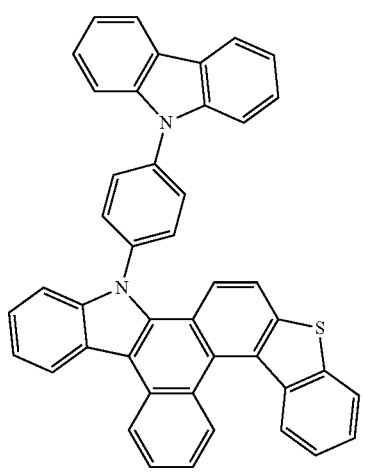

P 1-5

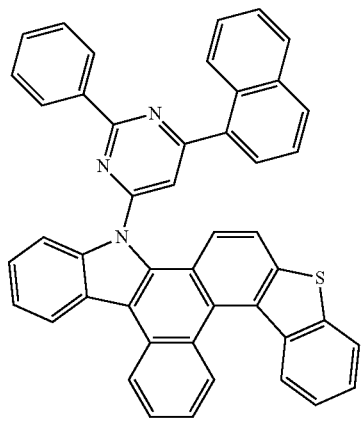

P 1-6
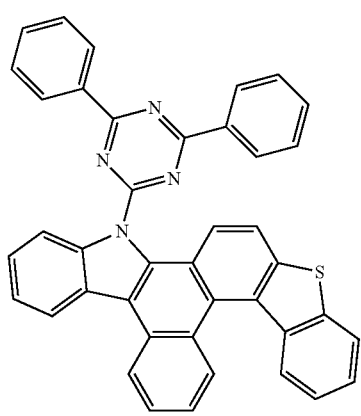
P 1-9
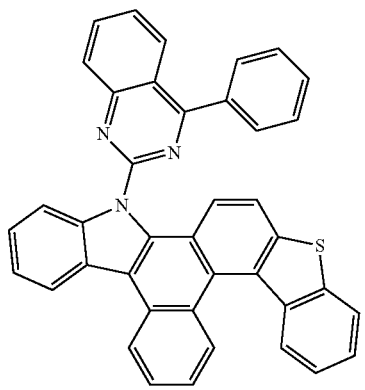
P 1-7
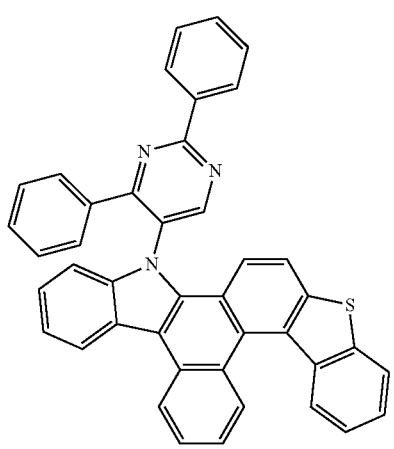
P 1-10
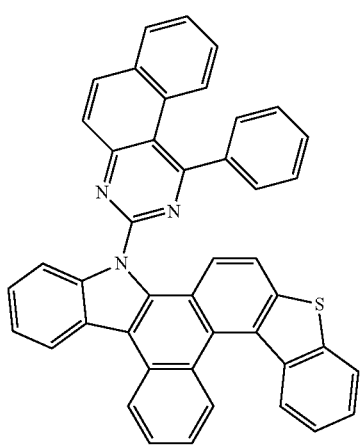
P 1-8
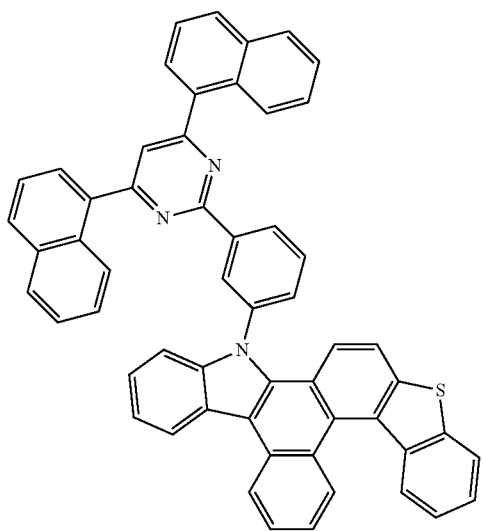
P 1-11
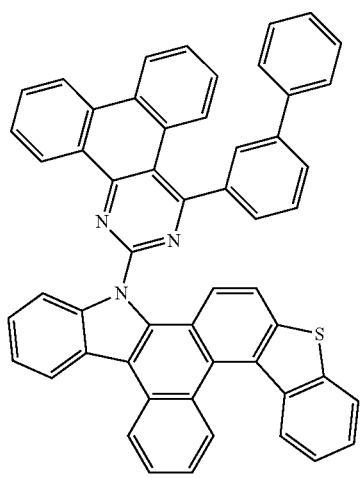

P 1-12
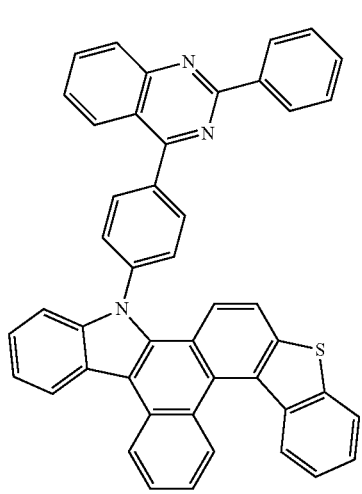
P 1-15
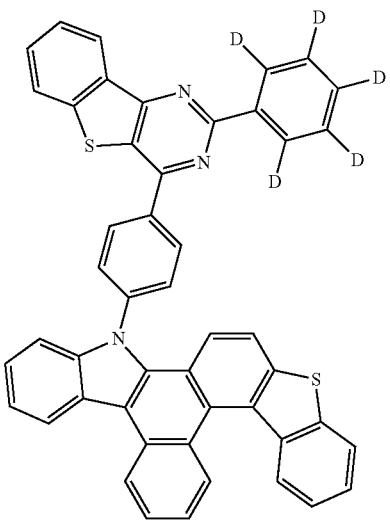
P 1-13
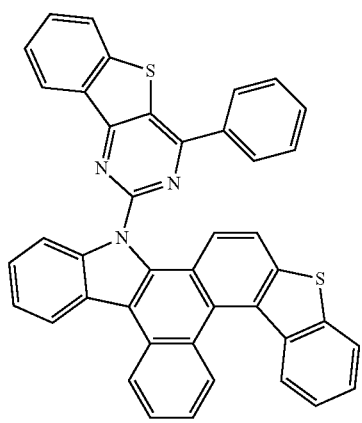
P 1-16
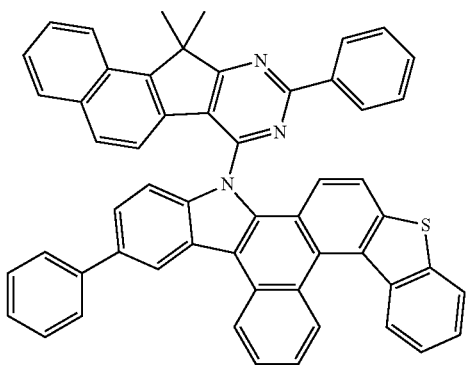
P 1-14
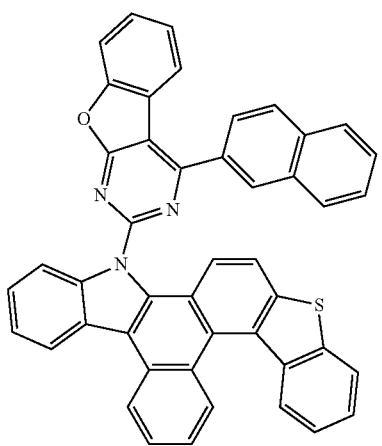
P 1-17
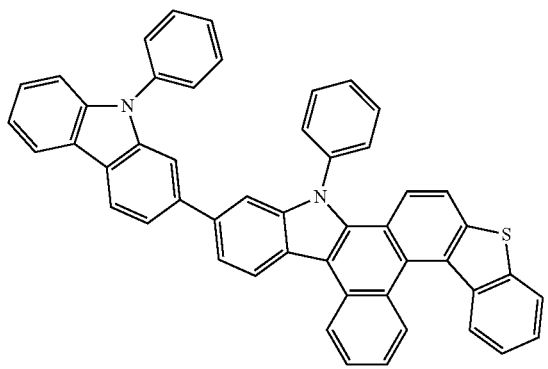

P 1-18
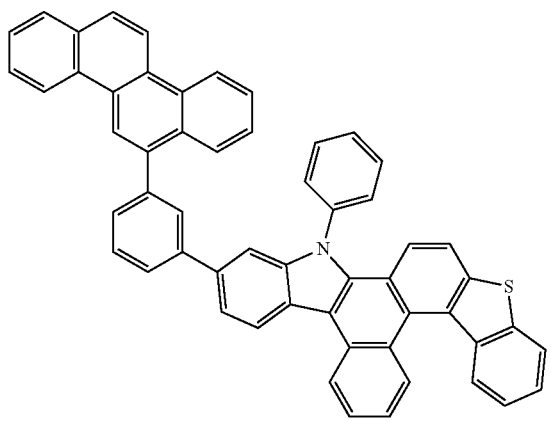
P 1-19
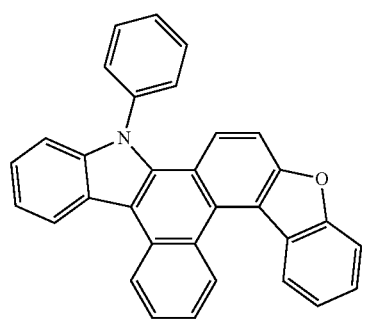
P 1-20
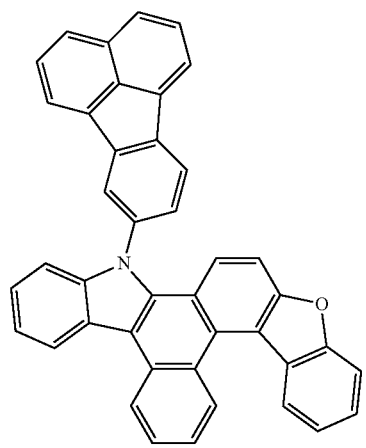
P 1-21
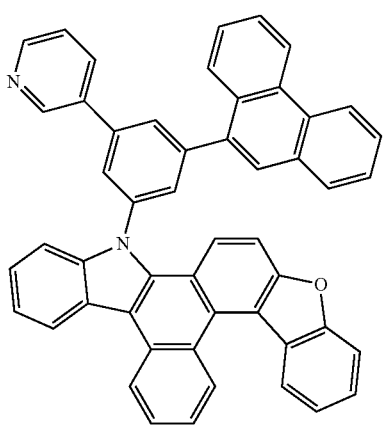
P 1-22
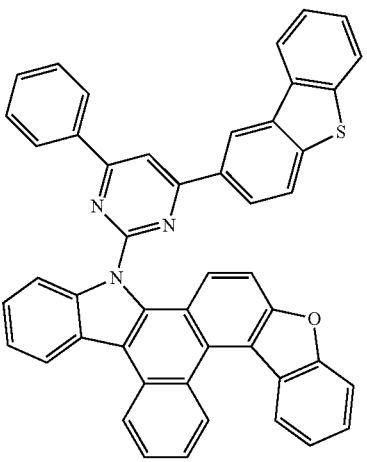
P 1-23
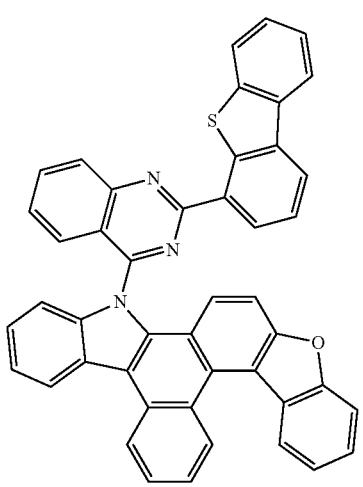
P 1-24
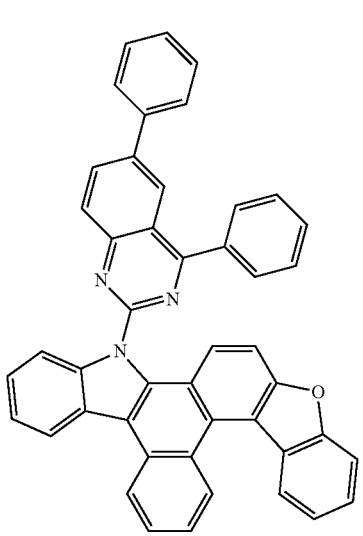

P 1-25
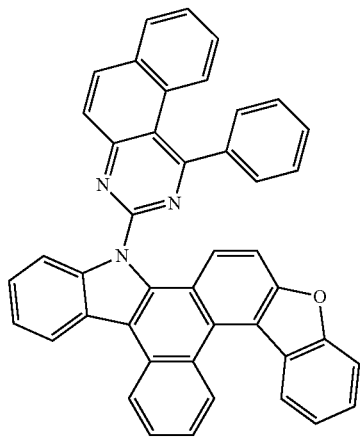
P 1-26
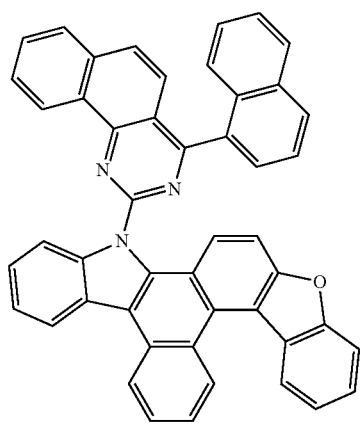
P 1-27
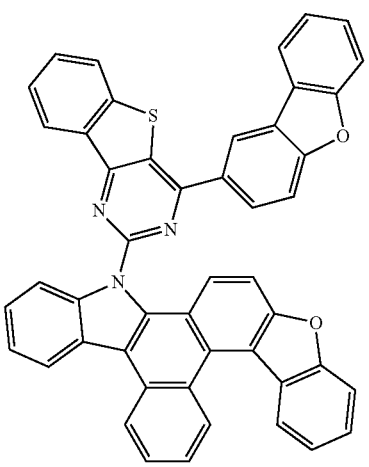
P 1-28
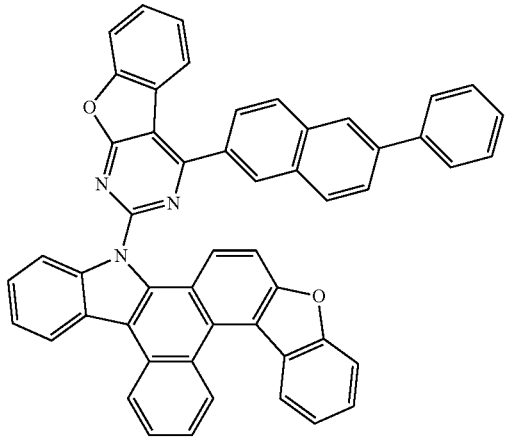
P 1-29
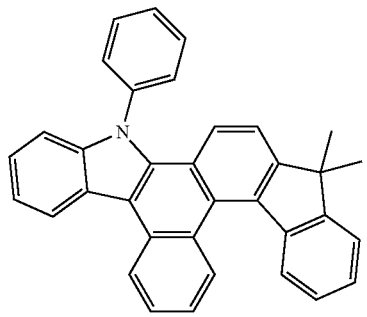
P 1-30
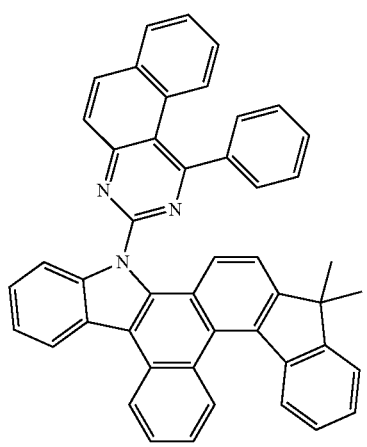

P 1-31
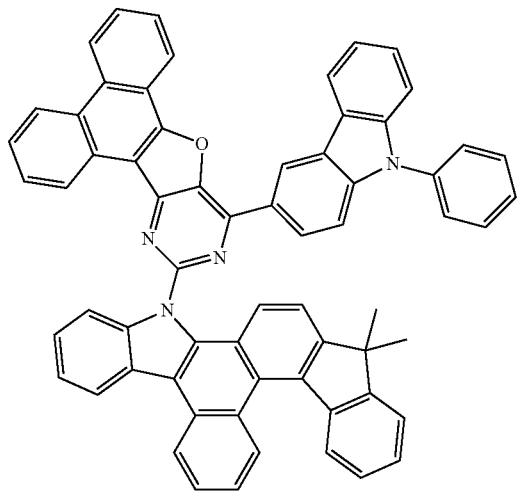
P 1-32
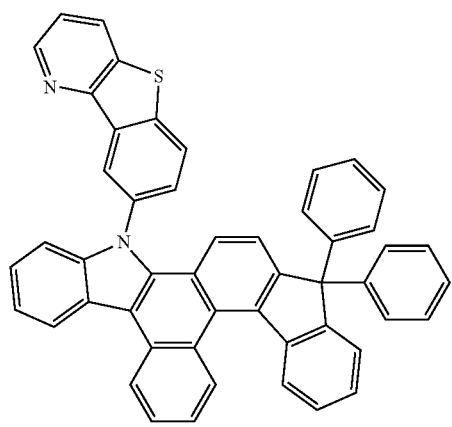
P 1-33
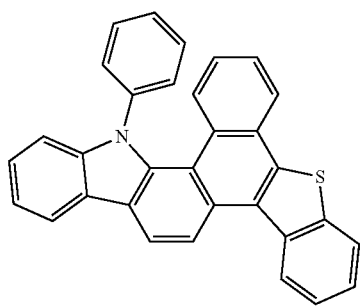
P 1-34
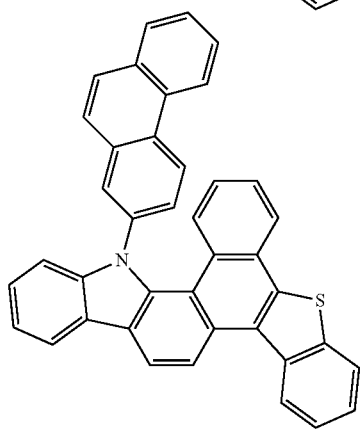
P 1-35
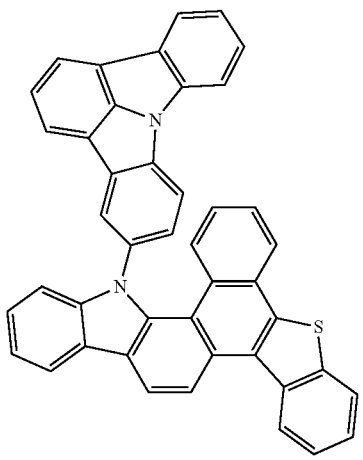
P 1-36
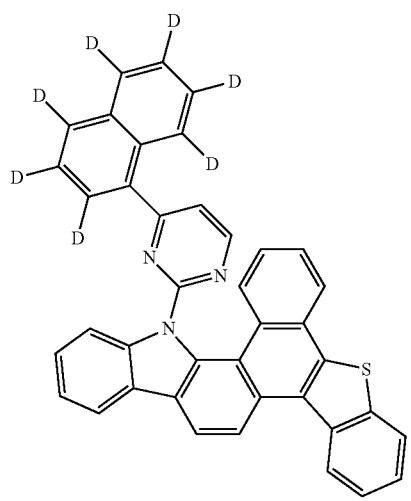
P 1-37
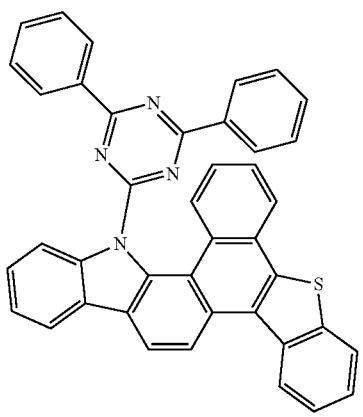

P 1-38
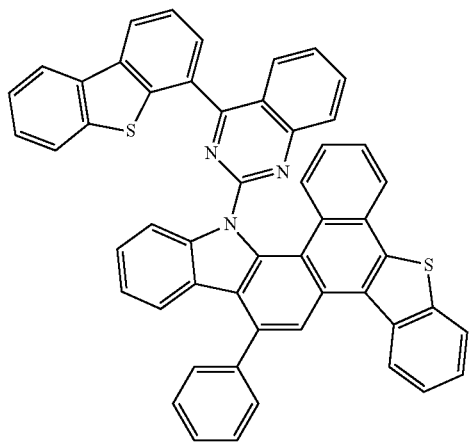
P 1-39
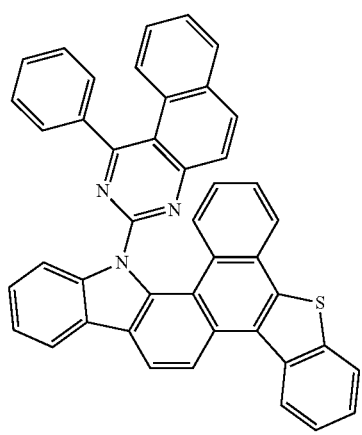
P 1-40
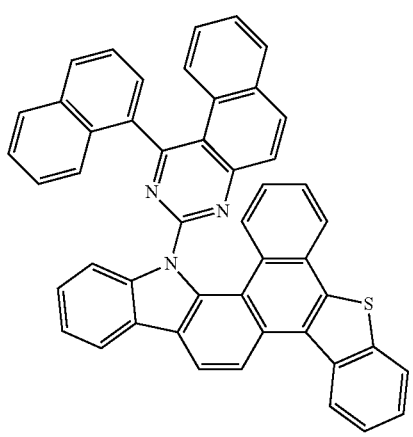
P 1-41
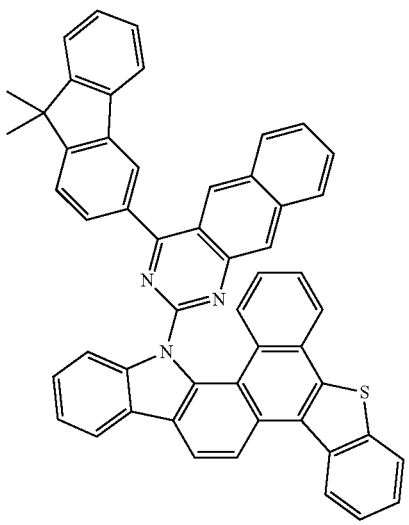
P 1-42
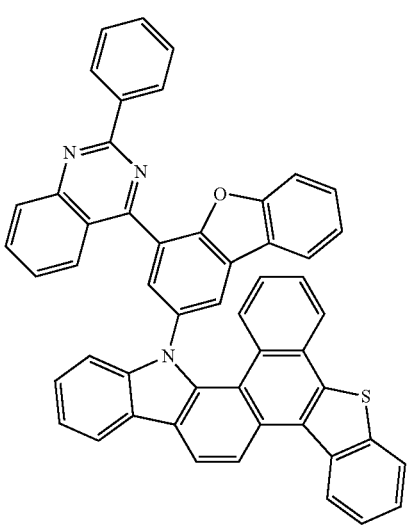
P 1-43
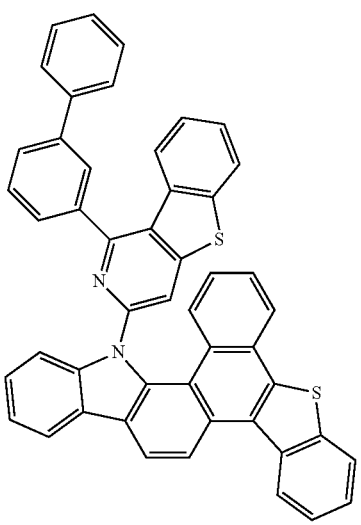

P 1-44
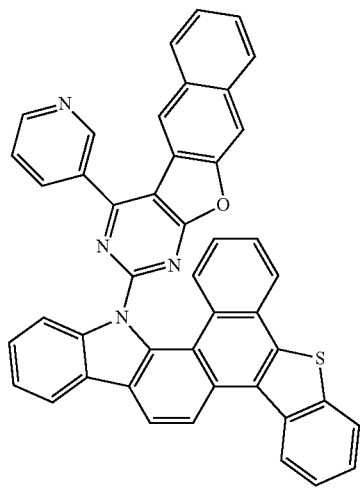
P 1-45
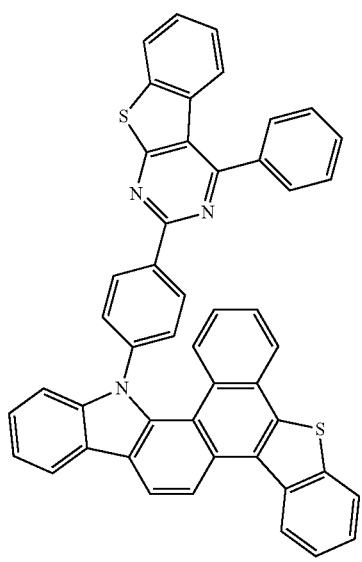
P 1-46
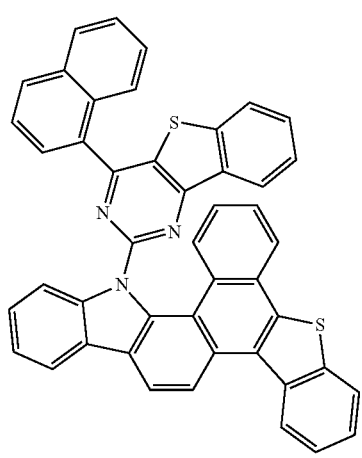
P 1-47
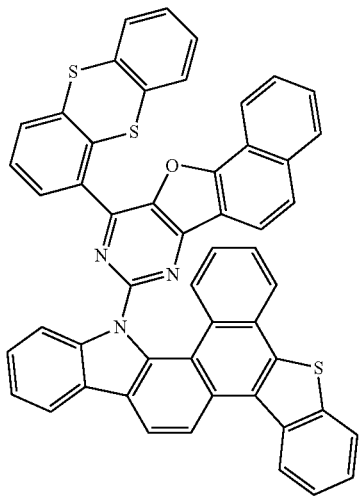
P 1-48
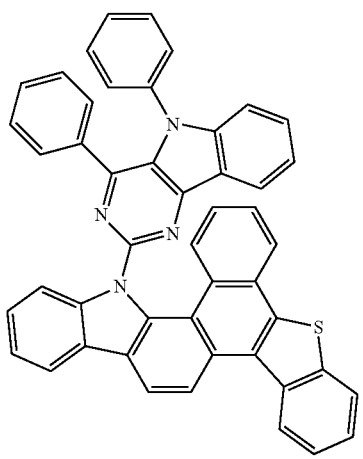
P 1-49
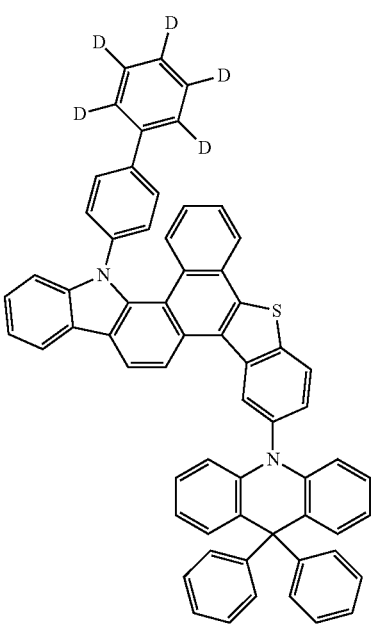

P 1-50
P 1-51
P 1-52
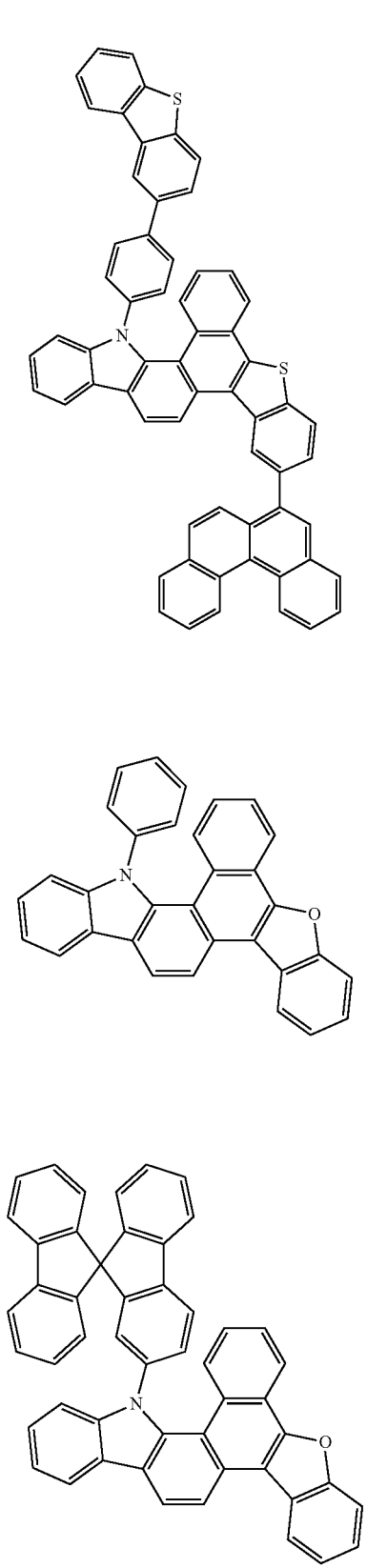
P 1-53
P 1-54
P 1-55
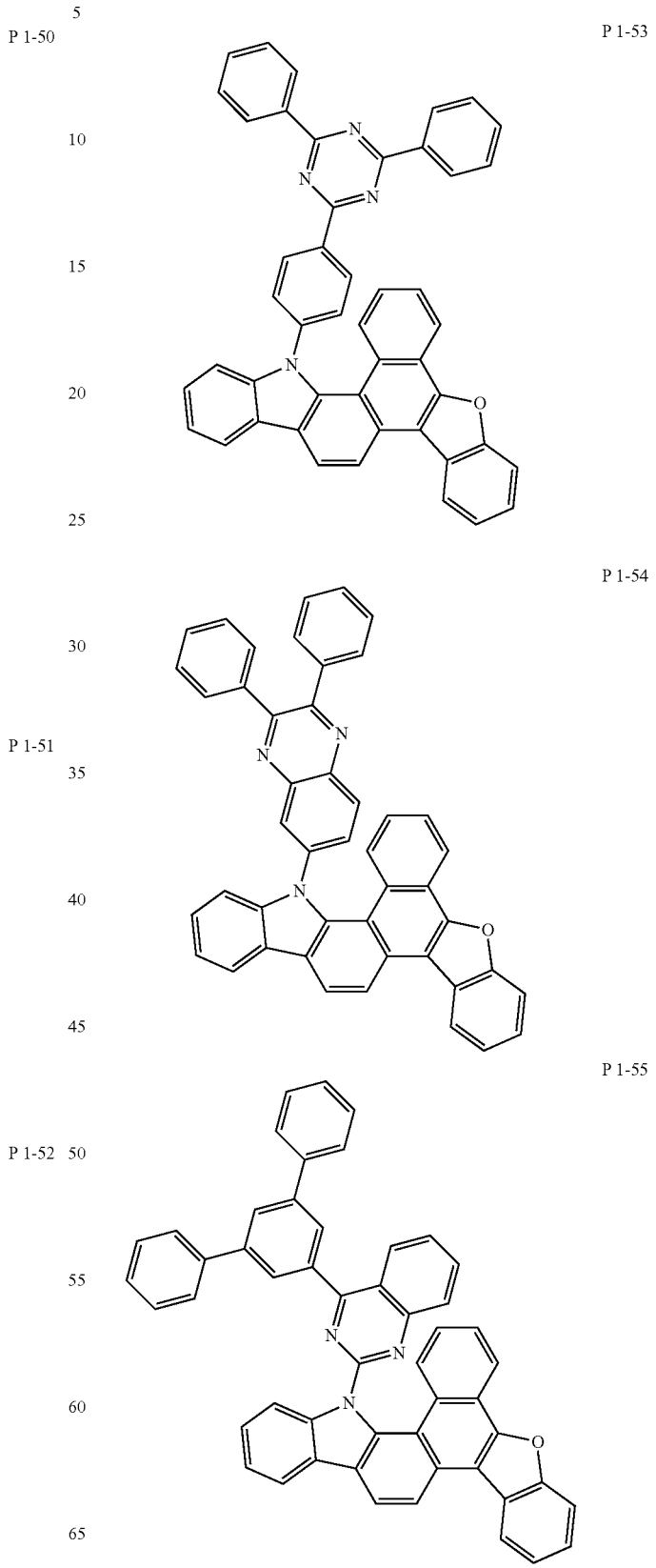

P 1-56
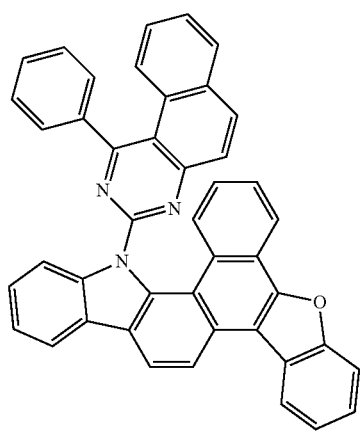
P 1-57
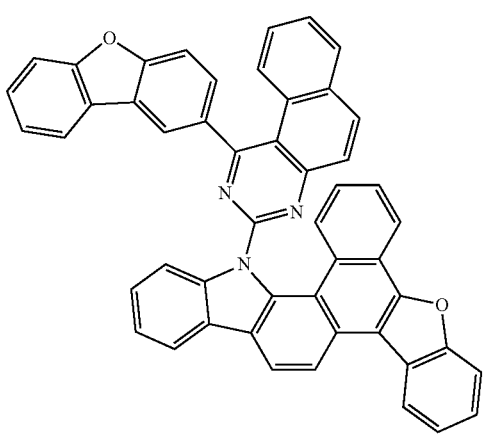
P 1-58
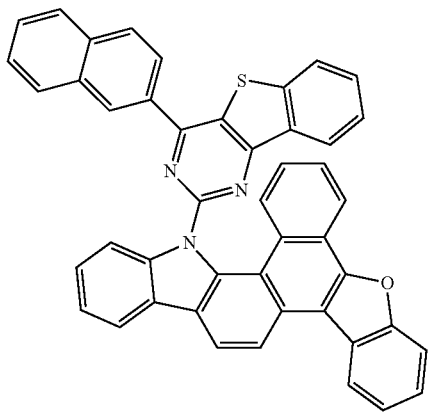
P 1-59
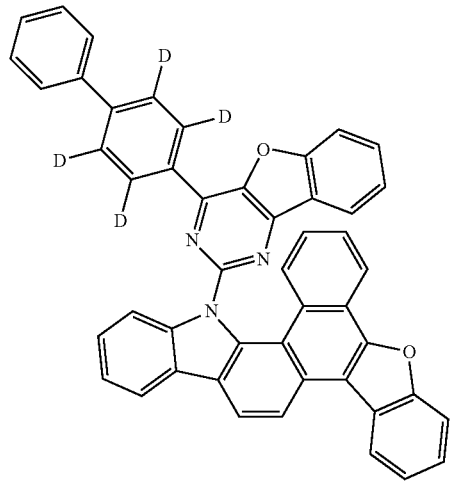
P 1-60
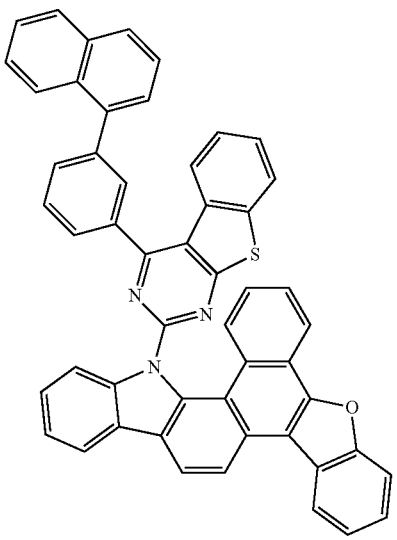
P 1-61
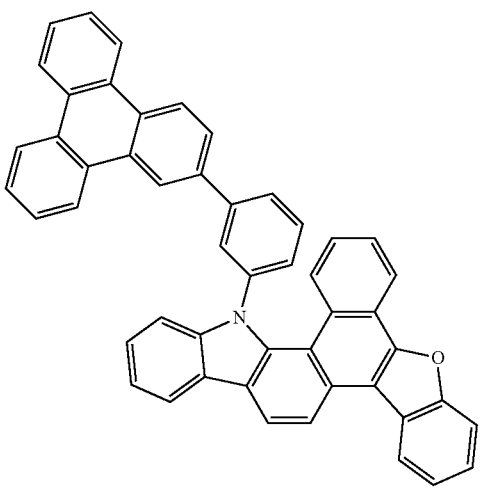

P 1-62
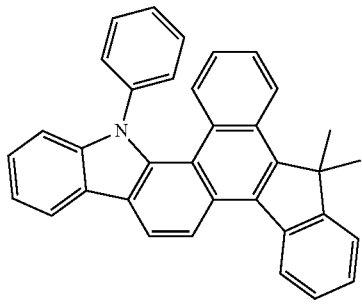
P 1-63
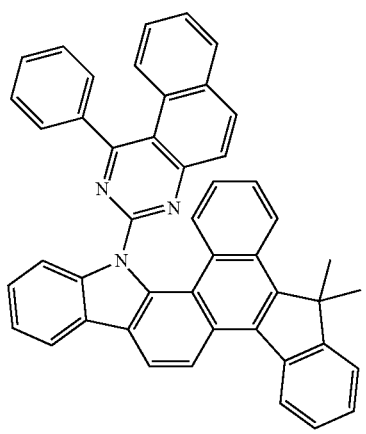
P 1-64
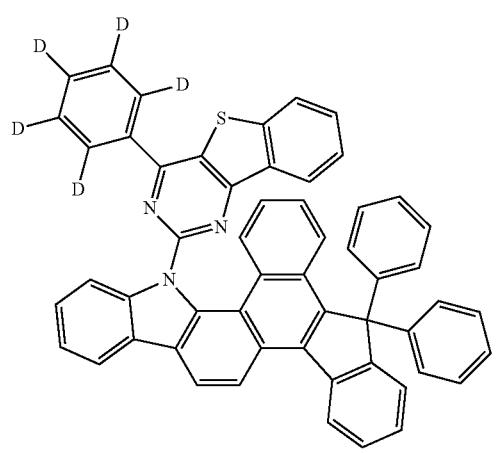
P 1-65
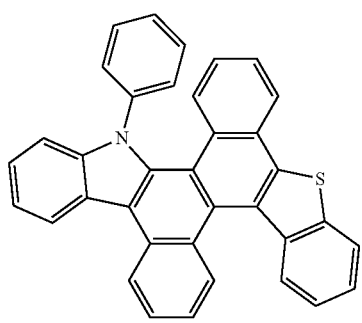
P 1-66
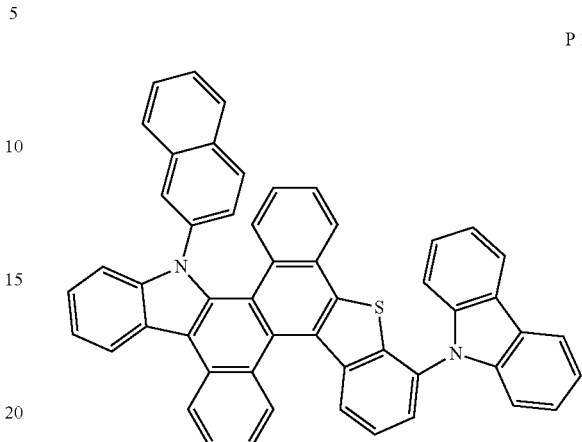
P 1-67
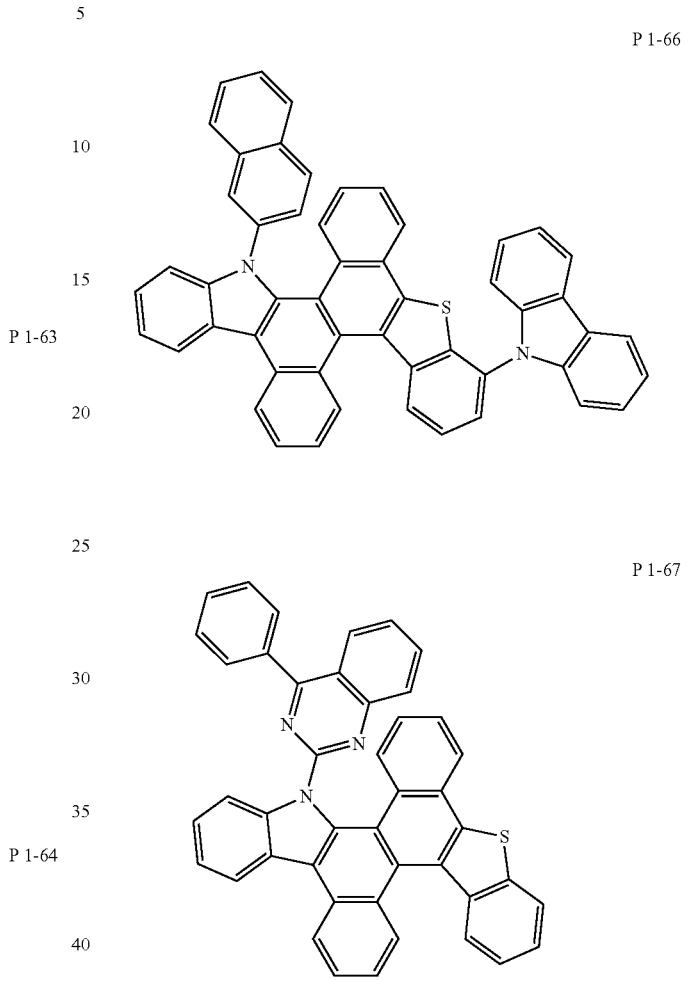
P 1-68
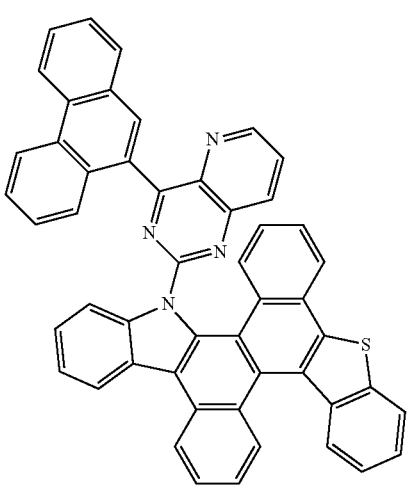

-continued
P 1-69
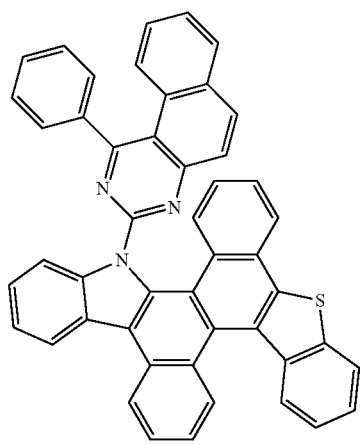
P 1-70
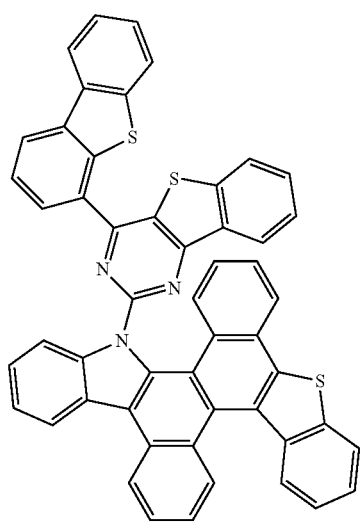
P 1-71
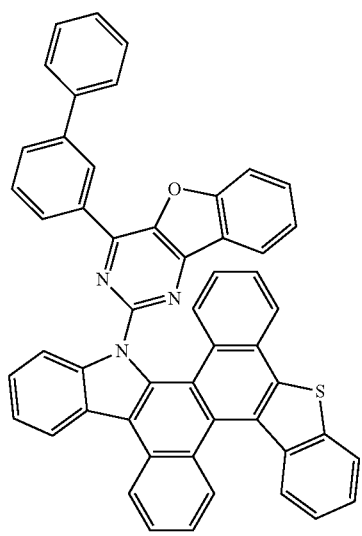
-continued
P 1-72
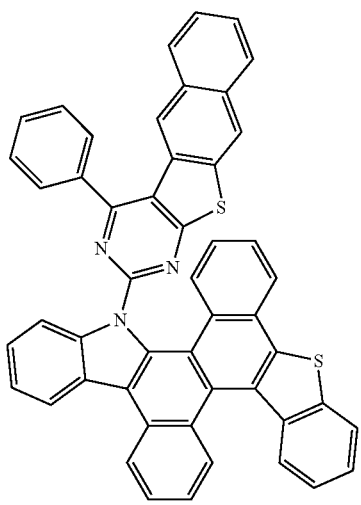
P 1-73
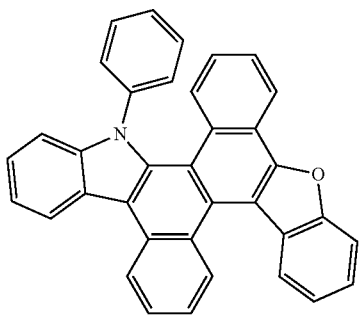
P 1-74
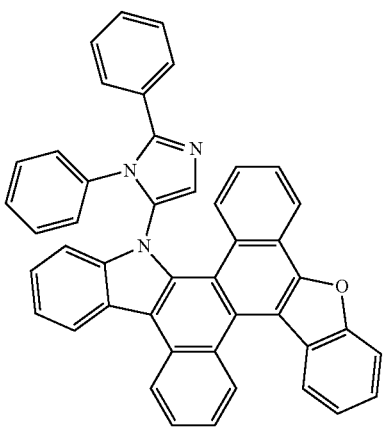

P 1-75
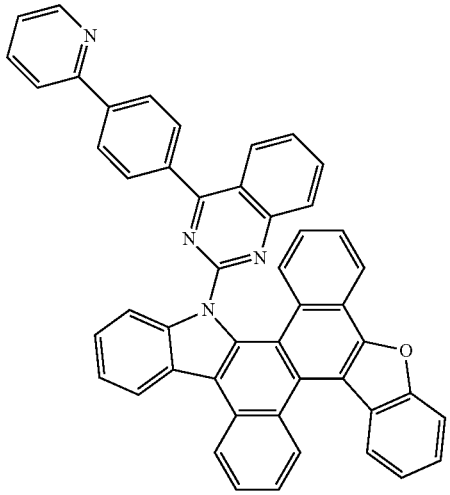
P 1-76
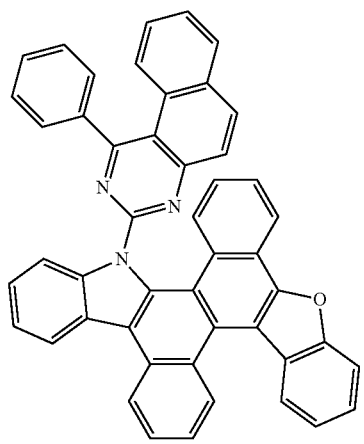
P 1-77
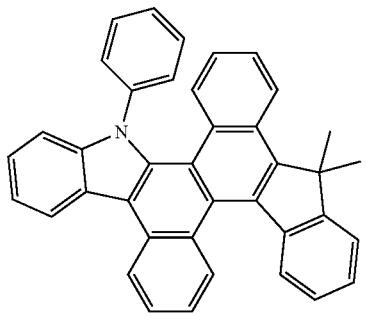
P 1-78
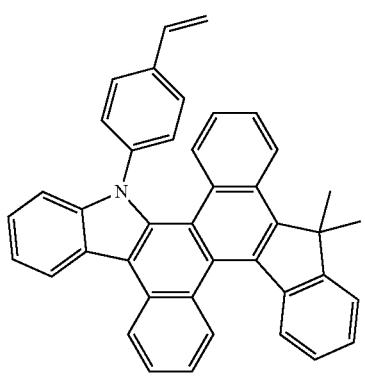
P 1-79
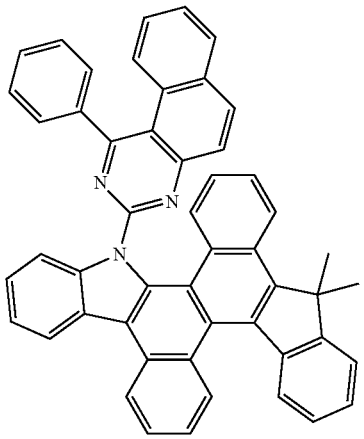
P 1-80
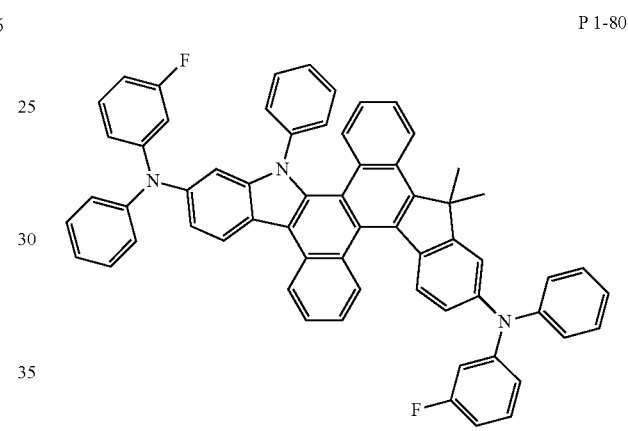
P 2-1
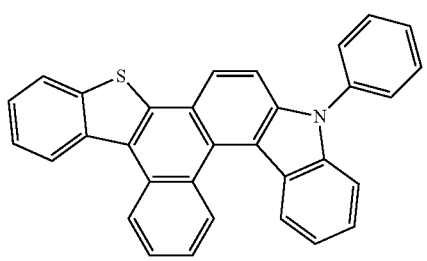
P 2-2
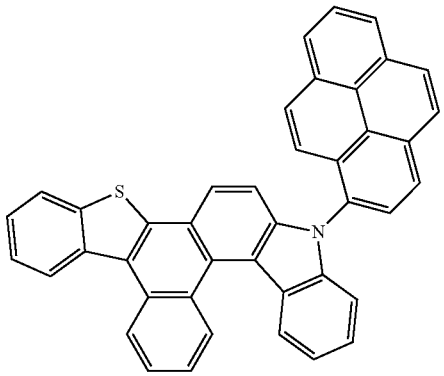

P 2-3
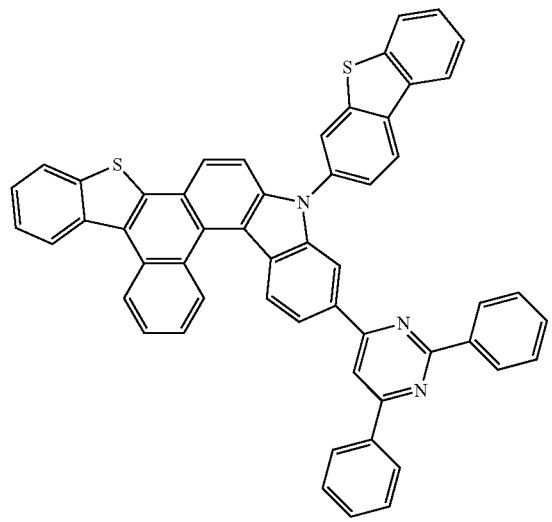
P 2-4
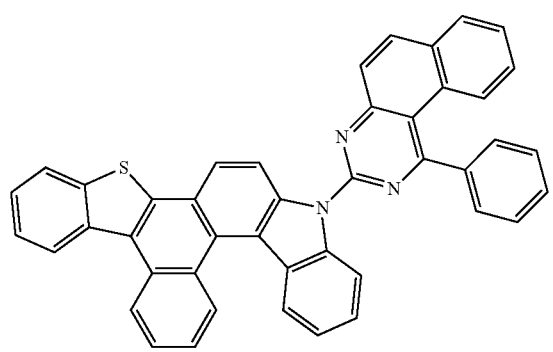
P 2-5
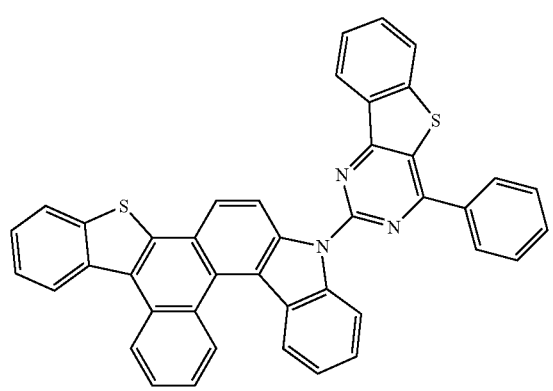
P 2-6
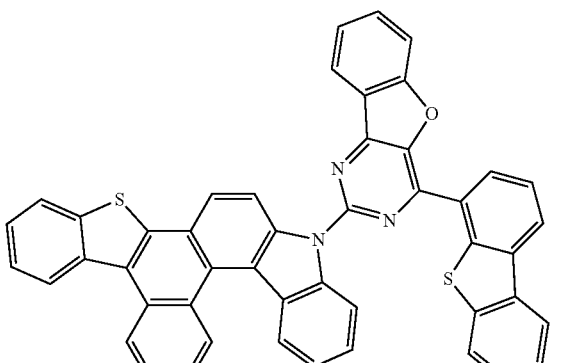
P 2-7
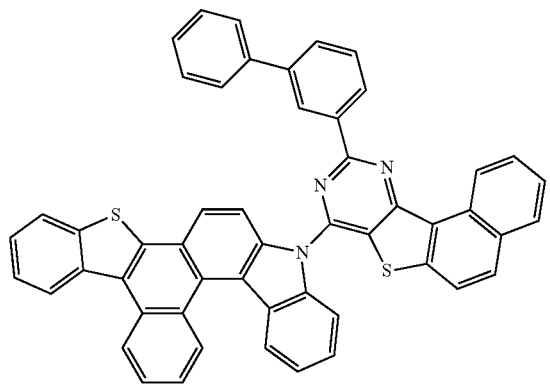
P 2-8
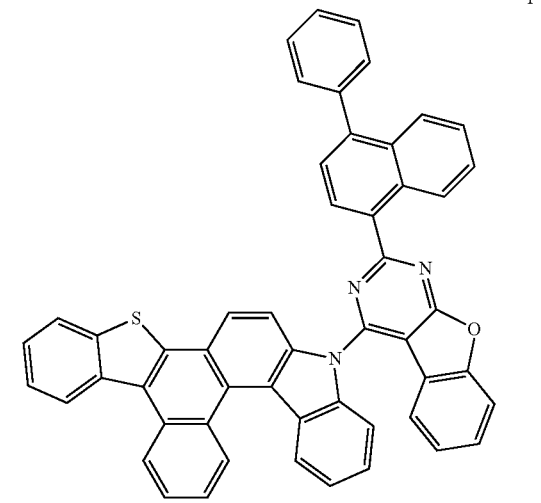
P 2-9
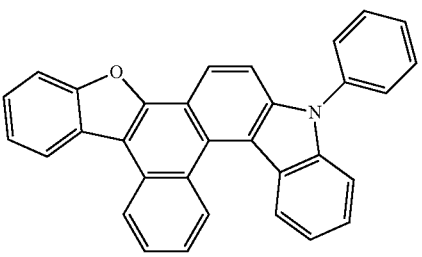

P 2-10
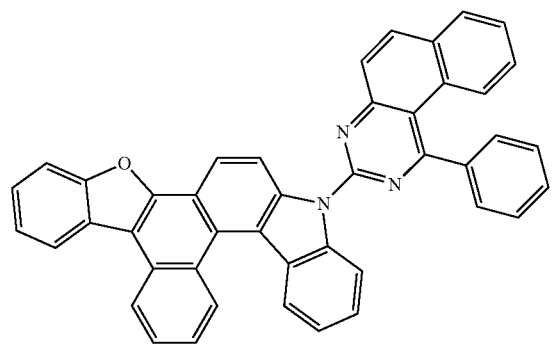
P 2-11
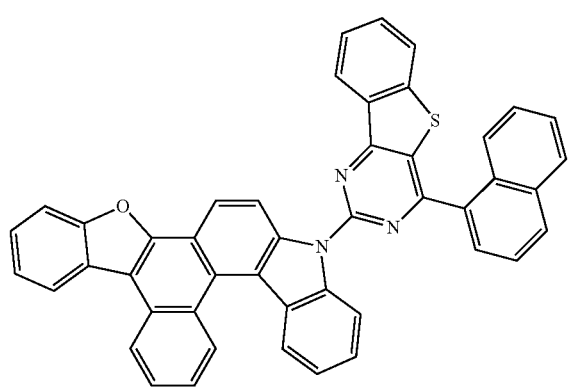
P 2-12
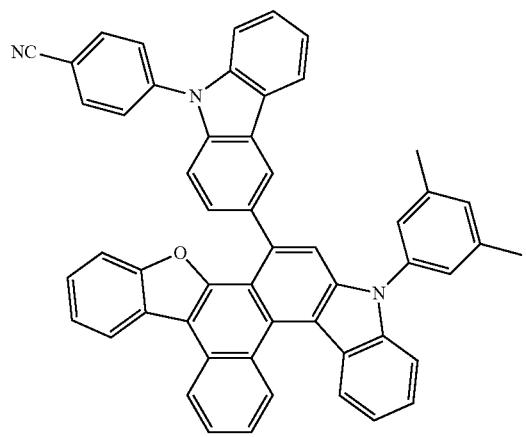
P 2-13
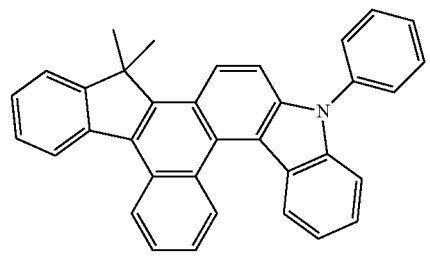
P 2-14
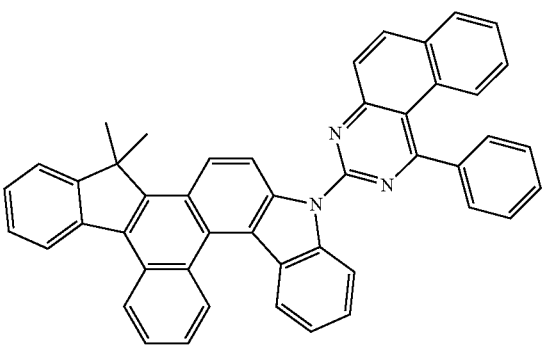
P 2-15
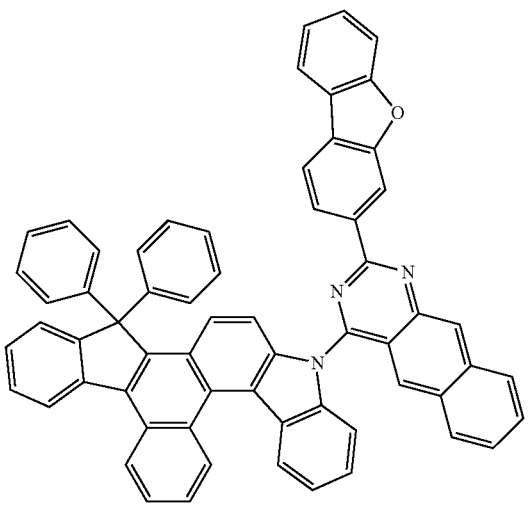
P 2-16
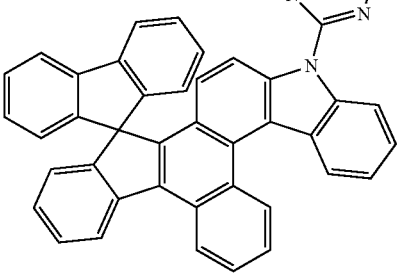
P 2-17
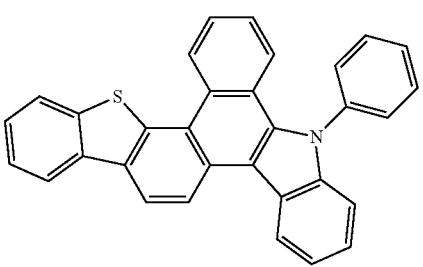

P 2-18
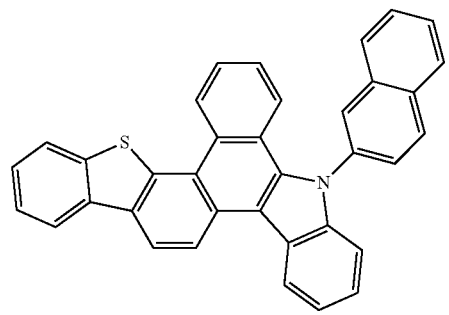
P 2-19
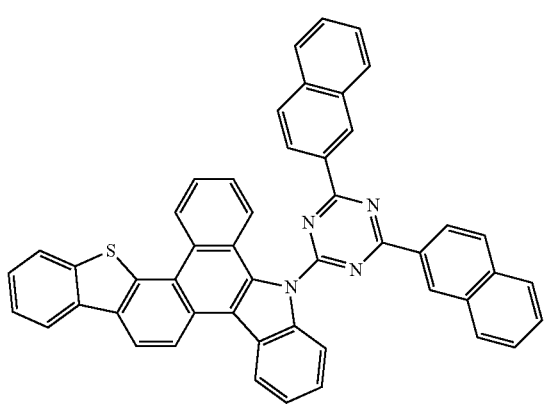
P 2-20
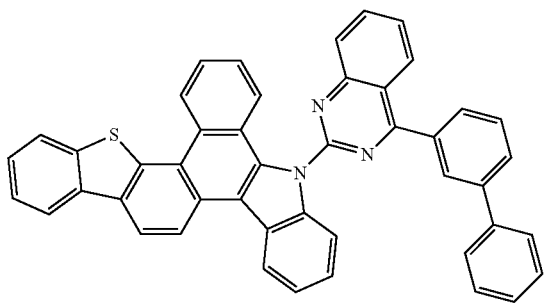
P 2-21
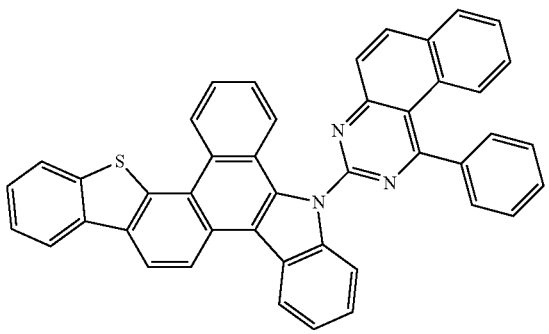
P 2-22
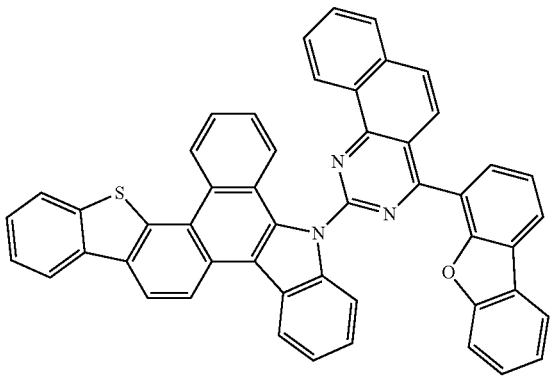
P 2-23
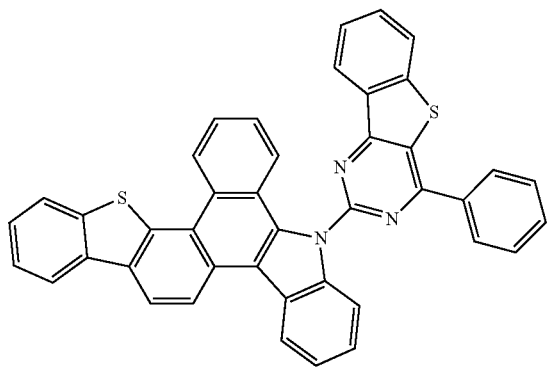
P 2-24
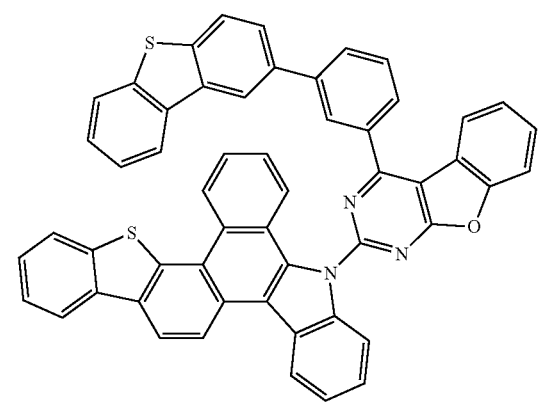
P 2-25
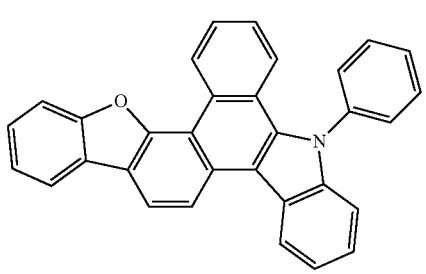

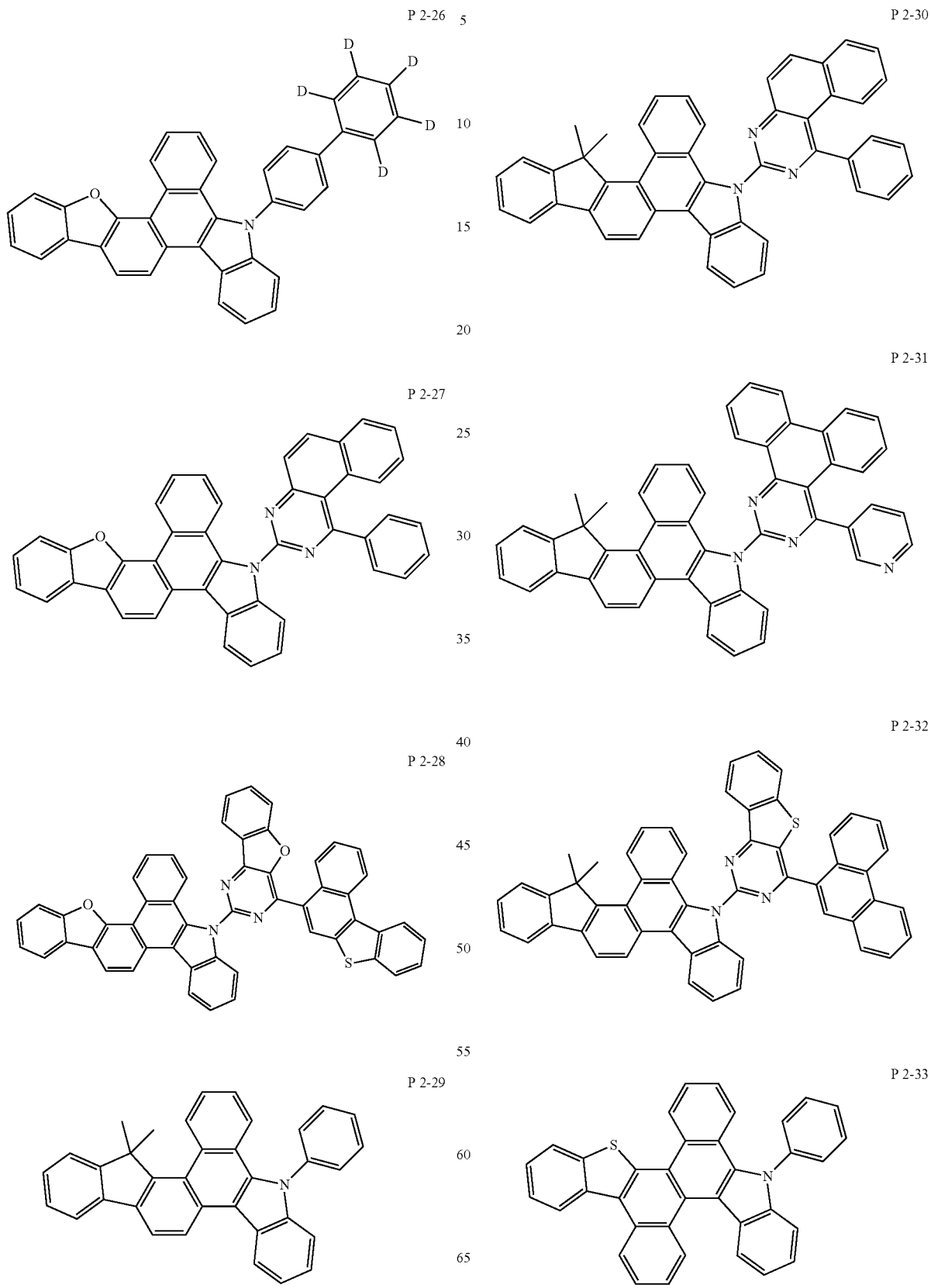

P 2-34
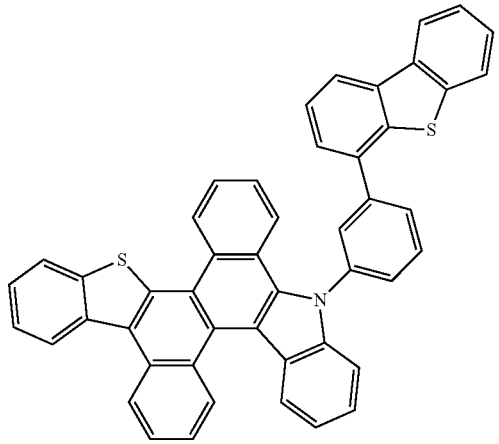
P 2-35
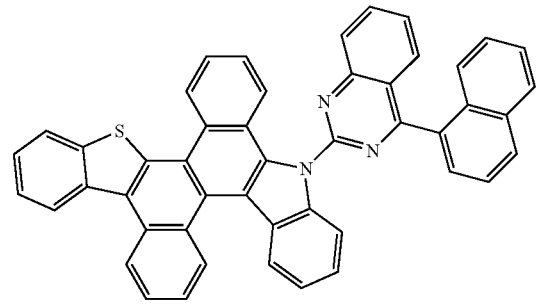
P 2-36
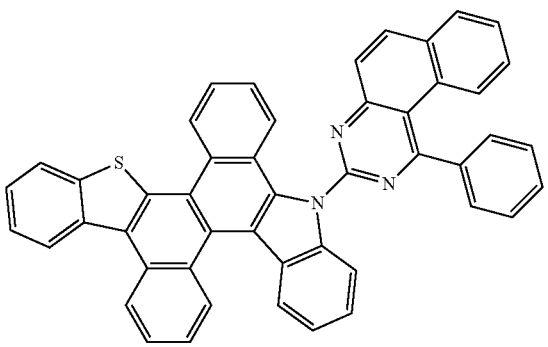
P 2-37
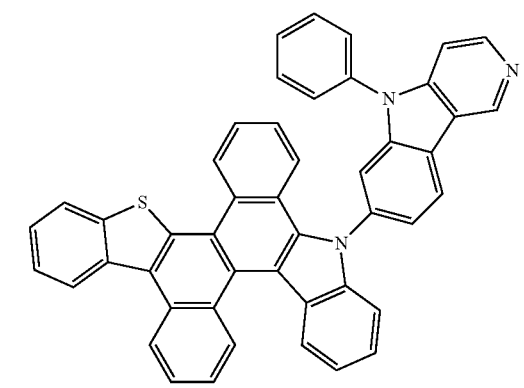
P 2-38
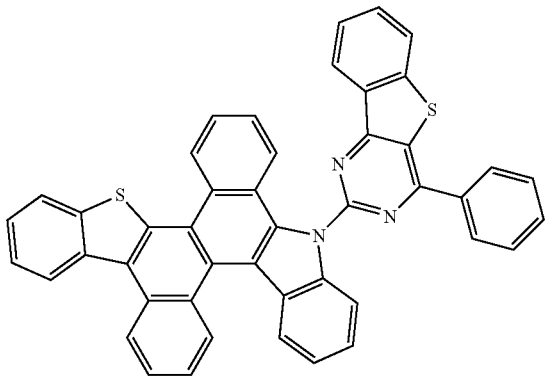
P 2-39
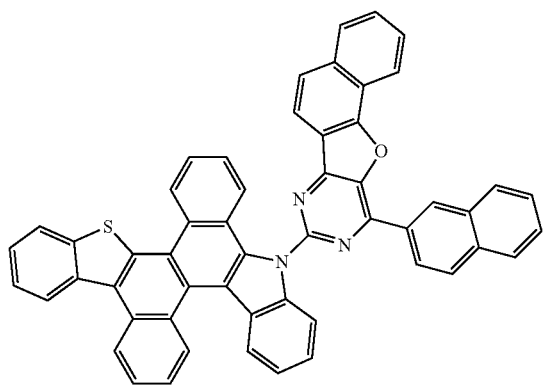
P 2-40
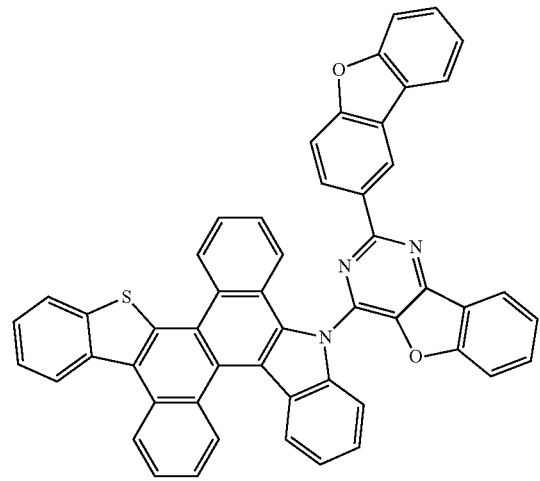
P 2-41
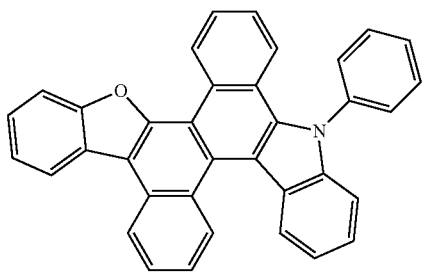

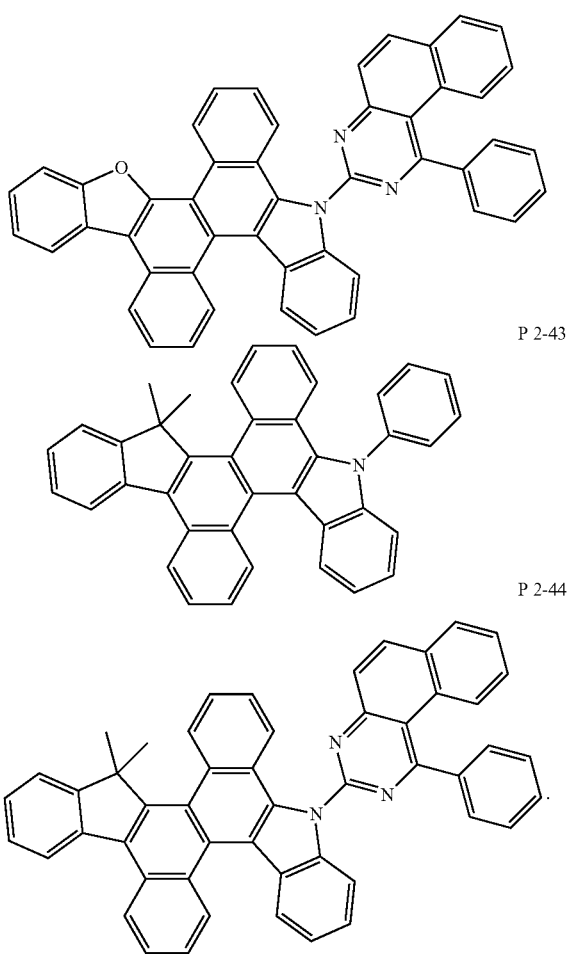

7. An organic electric element comprising a first electrode, a second electrode, and an organic material layer positioned between the first electrode and the second electrode, wherein the organic material layer comprises the compound of claim 1.

8. The organic electric element of claim 7, wherein the compound is comprised in at least one of the hole injection layer, the hole transport layer, the emission-auxiliary layer and the light emitting layer of the organic material layer, and the compound is comprised as a single compound or as a component of the mixture of two or more kinds.

9. The organic electric element of claim 8, wherein the compound is used as a phosphorescent host material of the light emitting layer.

10. The organic electric element of claim 8, wherein the compound is used as a green phosphorescent host material or a red phosphorescent host material of the light emitting layer.

11. The organic electric element of claim 7, wherein the organic material layer formed by any one of the processes of spin coating, nozzle printing, inkjet printing, slot coating, dip coating or roll-to-roll.

12. An electric device comprising a display device and a control unit for driving the display device, wherein the display device comprises the organic electric element of claim 7.

13. The electric device of claim 12, wherein the organic electric element is an organic light emitting diode, an organic solar cell, an organic photo conductor, an organic transistor, or an element for monochromatic or white illumination.

* * * * *

UNITED STATES PATENT AND TRADEMARK OFFICE
CERTIFICATE OF CORRECTION

PATENT NO. : 10,840,457 B2
APPLICATION NO. : 15/762164
DATED : November 17, 2020
INVENTOR(S) : Mun et al.

Page 1 of 1

It is certified that error appears in the above-identified patent and that said Letters Patent is hereby corrected as shown below:

In the Claims

Claim 1, Column 111, Line 35:
Please delete:
"$C_1$-050"
And replace with:
-- $C_1$-$C_{50}$ --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*